United States Patent
Hiddessen et al.

(10) Patent No.: US 9,527,049 B2
(45) Date of Patent: Dec. 27, 2016

(54) STABILIZED DROPLETS FOR CALIBRATION AND TESTING

(71) Applicant: Bio-Rad Laboratories, Inc., Hercules, CA (US)

(72) Inventors: Amy L. Hiddessen, Dublin, CA (US); Erin R. Chia, Berkeley, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 13/921,455

(22) Filed: Jun. 19, 2013

(65) Prior Publication Data

US 2014/0134623 A1   May 15, 2014

Related U.S. Application Data

(60) Provisional application No. 61/662,216, filed on Jun. 20, 2012.

(51) Int. Cl.

| | |
|---|---|
| B01F 5/00 | (2006.01) |
| B01F 9/00 | (2006.01) |
| B01F 11/00 | (2006.01) |
| C12Q 1/68 | (2006.01) |
| G01N 1/38 | (2006.01) |
| B01L 3/00 | (2006.01) |
| B01F 5/06 | (2006.01) |
| B01F 13/00 | (2006.01) |
| G01N 1/28 | (2006.01) |

(52) U.S. Cl.
CPC ........... *B01F 5/0085* (2013.01); *B01F 5/0647* (2013.01); *B01F 9/00* (2013.01); *B01F 11/00* (2013.01); *B01F 13/0062* (2013.01); *B01F 13/0072* (2013.01); *B01L 3/502784* (2013.01); *C12Q 1/6806* (2013.01); *G01N 1/38* (2013.01); *B01L 3/52* (2013.01); *B01L 2200/148* (2013.01); *B01L 2200/185* (2013.01); *B01L 2300/0867* (2013.01); *B01L 2300/1822* (2013.01); *B01L 2300/1827* (2013.01); *B01L 2300/1861* (2013.01); *G01N 2001/2893* (2013.01)

(58) Field of Classification Search
None
See application file for complete search history.

(56) References Cited

U.S. PATENT DOCUMENTS

| | | | |
|---|---|---|---|
| 5,260,002 A * | 11/1993 | Wang | 264/4.1 |
| 7,422,307 B2 | 9/2008 | Yogi et al. | |
| 2007/0045117 A1 | 3/2007 | Pamula et al. | |
| 2008/0003142 A1* | 1/2008 | Link et al. | 422/82.08 |
| 2009/0139576 A1 | 6/2009 | Crenshaw et al. | |
| 2010/0172831 A1 | 7/2010 | Mason et al. | |
| 2010/0173394 A1 | 7/2010 | Colston, Jr. et al. | |
| 2010/0285573 A1 | 11/2010 | Leck et al. | |
| 2011/0053798 A1 | 3/2011 | Hindson et al. | |
| 2011/0086780 A1 | 4/2011 | Colston, Jr. et al. | |
| 2011/0092373 A1 | 4/2011 | Colston, Jr. et al. | |
| 2011/0092376 A1 | 4/2011 | Colston, Jr. et al. | |
| 2011/0103176 A1 | 5/2011 | Van Dam et al. | |
| 2011/0145924 A1 | 6/2011 | Kolsek et al. | |
| 2011/0217711 A1 | 9/2011 | Hiddessen et al. | |
| 2011/0217712 A1 | 9/2011 | Hiddessen et al. | |
| 2011/0217736 A1 | 9/2011 | Hindson et al. | |
| 2011/0311978 A1 | 12/2011 | Makarewicz, Jr. et al. | |
| 2013/0139477 A1* | 6/2013 | Abell et al. | 53/473 |

FOREIGN PATENT DOCUMENTS

| | | |
|---|---|---|
| EP | 1574586 A2 | 9/2005 |
| GB | 2482911 A | 2/2012 |
| KR | 2011-0093293 A | 8/2011 |
| KR | 2011-0093294 A | 8/2011 |
| WO | WO 2006/027602 A1 | 3/2006 |
| WO | WO 2007/081386 A2 | 7/2007 |
| WO | 2007089541 A2 | 8/2007 |
| WO | WO 2010/036352 A1 | 4/2010 |
| WO | 2010128157 A1 | 11/2010 |

OTHER PUBLICATIONS

Brouzes, et al. Droplet microfluidic technology for single-cell high-throughput screening. Proc Natl Acad Sci U S A. Aug. 25, 2009;106(34):14195-200.

DeMello, A. J. Control and detection of chemical reactions in microfluidic systems. Nature. Jul. 27, 2006;442(7101):394-402.

International search report and written opinion dated Sep. 17, 2013 for PCT/US2013/046654.

European Patent Office, "European Search Report" in connection with related European Patent Application No. 13806568, dated May 9, 2016, 9 pages.

* cited by examiner

*Primary Examiner* — David Thomas
(74) *Attorney, Agent, or Firm* — Kolisch Hartwell, P.C.

(57) ABSTRACT

Provided herein, are droplet mixture compositions and systems and methods for forming mixtures of droplets. The system may comprise two or more droplet generation units. Each unit may include at least one first input well, a second input well, and an output well connected to the first and second input wells by channels that form a droplet generator. The combined droplet populations can be mixed, heated, and collected for multiple uses, such as for use as calibration standards for instrument testing and analysis.

12 Claims, 11 Drawing Sheets

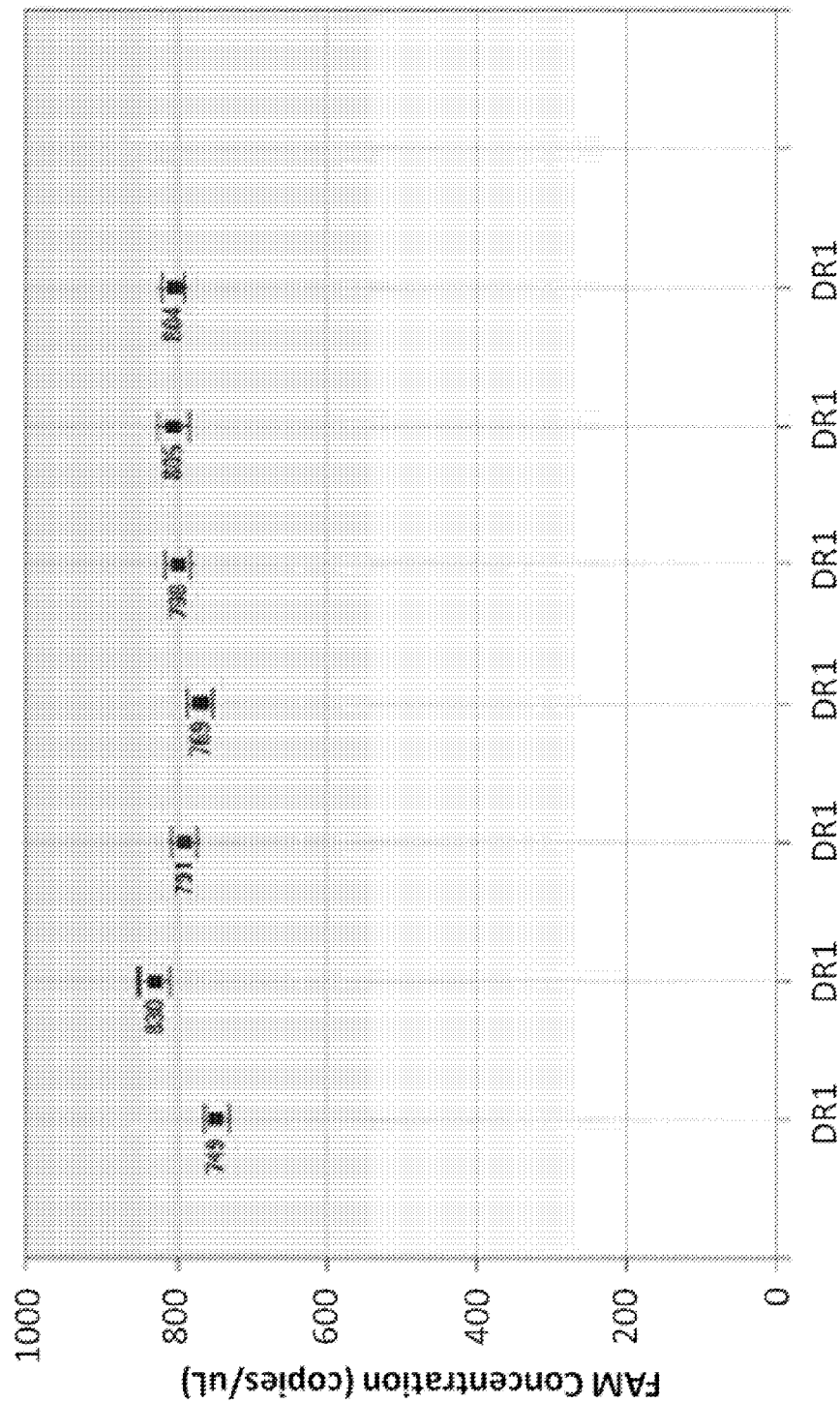

ary of the invention are set forth with
STABILIZED DROPLETS FOR CALIBRATION AND TESTING

CROSS-REFERENCE

This application claims the benefit of U.S. Patent App. No. 61/662,216, filed Jun. 20, 2012, which application is herein incorporated by reference in its entirety.

BACKGROUND

Assays are generally procedures for determining the presence, quantity, activity, and/or other properties or characteristics of components in a sample. In some cases, the samples to be assayed are complex, the components of interest within the samples—e.g., a nucleic acid, an enzyme, a virus, a bacterium—are only minor constituents of the samples, and the results of the assays are required quickly and/or for many samples.

Some current systems perform assays with the aid of droplets generated in droplet generators. Often, the droplet generators work by partitioning a sample into multiple droplets. The sample may be an aqueous sample that is contacted with a stream of oil fluid in such a way as to form a disperse phase of aqueous droplets in a continuous oil phase. In such systems, droplets with sample partitions are generated for storage in a droplet storage vessel, from which a sample can subsequently be processed (e.g., amplified in the case of PCR) and analyzed.

Due to the sensitivity of droplets to mechanical motion and accompanying shear forces, care is ordinarily taken in transporting droplets to a droplet storage vessel, or directing a droplet from the droplet generator to a processing station and subsequently a droplet reader. Improved droplet generation mechanisms would be of great benefit to biological and clinical assays that use droplet-based assays.

INCORPORATION BY REFERENCE

All publications and patent applications mentioned in this specification are herein incorporated by reference in their entireties to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 6B provides a graphical depiction of simulated 6-carboxyfluorescein (FAM) concentrations determined by counting positive and negative droplets (prepared with known FAM concentrations) and converting to FAM concentration using a Poisson equation. Fluorescence emission was detected from droplets within the same droplet population flowed through a T-junction channel arrangement followed by flow through a serpentine channel arrangement.

SUMMARY

Figure 1:
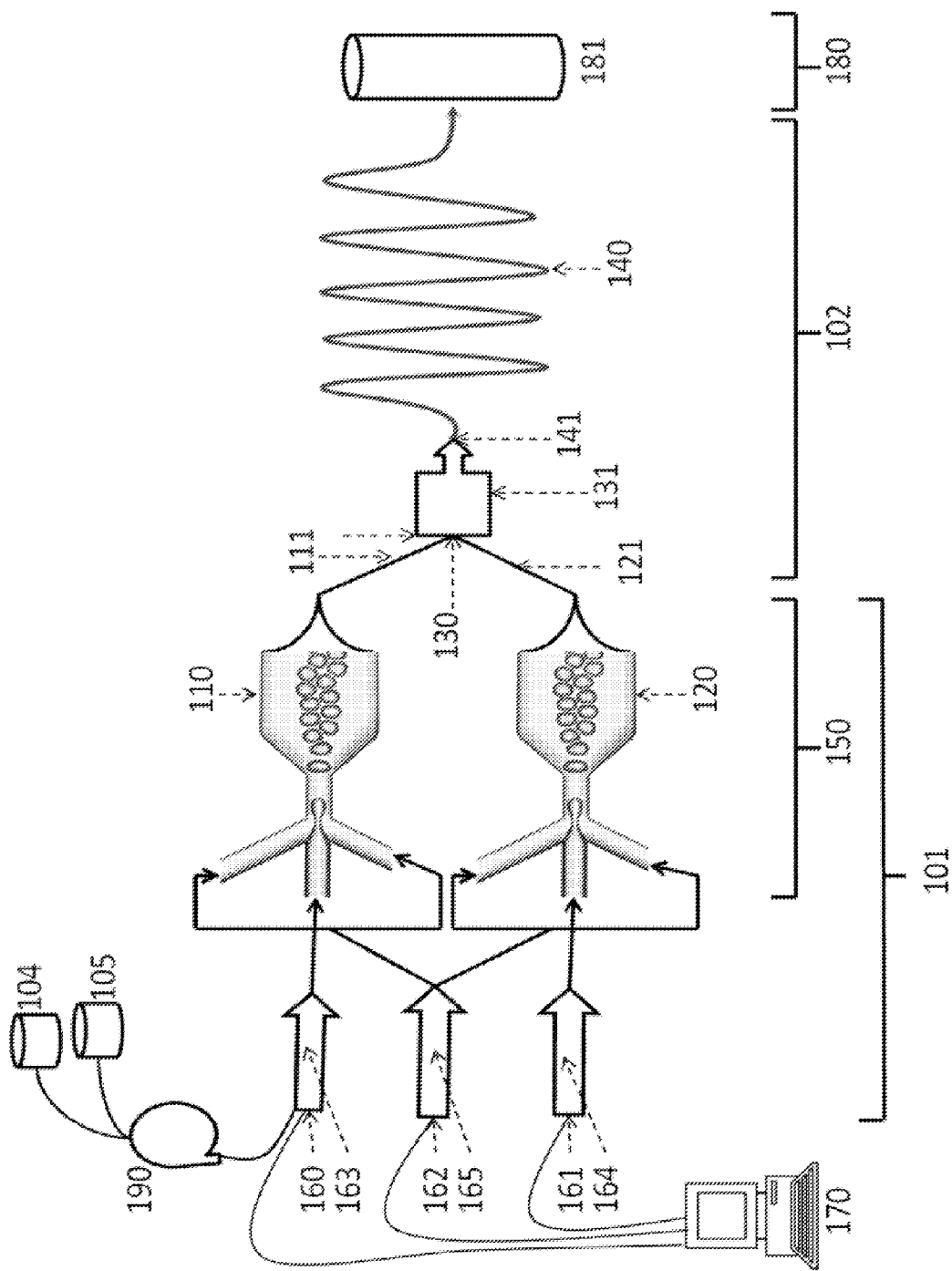
FIG. 1 is an exemplary droplet generating and mixing system.

Provided herein is a method of mixing droplets, comprising the steps of:
a. combining at least a portion of a first population of droplets with at least a portion of a second population of droplets to form a combined population of droplets; and
b. flowing the combined population of droplets through a mixing module using a pressure source to drive the flow; wherein a first droplet passes a second droplet in the mixing module, and wherein 10% or more of the droplets in the combined droplet population remain intact after flowing through the mixing module.

Also provided herein is a method of mixing droplets, comprising the steps of:
a. combining at least a portion of a first population of droplets with at least a portion of a second population of droplets to form a combined population of droplets;
b. flowing the combined population of droplets through a mixing module, wherein a first droplet passes a second droplet in the mixing module; and
c. stabilizing the first population of droplets, second population of droplets, combined population of droplets, or a combination thereof, wherein the droplets are more resistant to coalescence, shearing, breakage, and/or damage, such as damage from shearing, after stabilization than before stabilization.

Also provided herein is a method of mixing droplets, comprising the steps of:

a. combining at least a portion of a first population of droplets with at least a portion of a second population of droplets to form a combined population of droplets;

b. flowing the combined population of droplets through a mixing module; and c. stabilizing the first population of droplets, second population of droplets, combined population of droplets, or a combination thereof without causing a PCR amplification reaction, wherein the droplets are more resistant to coalescence, shearing, breakage, and/or damage, such as damage from shearing, after stabilization than before stabilization.

In some embodiments, the mixing module comprises a mixing channel. In some embodiments, the mixing channel has a nonlinear configuration. In some embodiments, the nonlinear configuration comprises at least one region of curvature. In some embodiments, the nonlinear configuration comprises at least one turn. In some embodiments, the nonlinear configuration is a serpentine configuration. In some embodiments, the mixing channel has a linear configuration. In some embodiments, the mixing channel comprises a length that affords mixing due to buoyancy mismatch between droplets and a continuous phase or a carrier fluid around the droplets. In some embodiments, the mixing channel has a cross-sectional dimension from 1 time to 1000 times the average droplet diameter.

In some embodiments, the step of combining the droplets occurs in the mixing module. In some embodiments, step (b) comprises mixing the first and second population of droplets at a junction, such as a branched junction, for example, a T-junction or a Y-junction, or through the use of "Marangoni" phenomenon. In some embodiments, electrowetting is not used to flow the droplets. In some embodiments, the droplets flow through a continuous flow device. In some embodiments, the droplets flow through a microfluidic device.

In some embodiments, the pressure source provides negative pressure. In some embodiments, the pressure source provides positive pressure.

In some embodiments, stabilizing comprises increasing the temperature of the droplets. In some embodiments, stabilizing comprises incubating at a temperature from 4° C. to 99° C. for 0.01 or more seconds. In some embodiments, the first or second population of droplets, or both, is stabilized according to step (c) before step (a). In some embodiments, the combined droplet population is stabilized according to step (c) before, during, or after step (b). In some embodiments, stabilizing comprises forming a droplet skin. In some embodiments, stabilizing comprises providing energy to the droplets. In some embodiments, the energy is thermal, electromagnetic, electrical, chemical, or mechanical energy, or any combination thereof. In some embodiments, the electromagnetic energy is gamma rays, x-rays, ultraviolet rays, visible light, infrared rays, microwaves, radio waves, or any combination thereof. In some embodiments, the thermal energy is heat, conduction, convection, or a combination thereof. In some embodiments, the energy is provided by one or more heating element(s). In some embodiments, the one or more heating element comprises a resistive heating element, thermoelectric device, heating block, lamp, light source, microwave, radiation source, water bath, or any combination thereof. In some embodiments, two or more heating elements provide energy, thereby allowing for temperature cycling. In some embodiments, the energy initiates a reaction within the droplets. In some embodiments, a reaction comprises PCR, RT-PCR, isothermal amplification, in vitro translation, or a combination thereof. In some embodiments, stabilizing prevents 10% or more of the first population of droplets, second population of droplets, combined population of droplets, or a combination thereof, from coalescing.

In some embodiments, the method further comprises partitioning a sample with a first droplet generator to produce the first population of droplets and partitioning a sample with a second droplet generator to produce the second population of droplets, wherein each partitioning step is performed before step (a). In some embodiments, at least a portion of the first population of droplets are present in a first channel, and wherein at least a portion of the second population of droplets are located within a second channel that is different from the first channel. In some embodiments, the first channel and the second channel intersect. In some embodiments, the first and second channel flow into the mixing module.

In some embodiments, the method further comprises collecting the droplet mixture.

In some embodiments, the method further comprises preparing the droplet mixture for transport, storage, or a combination thereof. In some embodiments, preparing comprises placing the droplet mixture, and optionally a volume of carrier fluid, such as oil, in a vessel. The carrier fluid can be any suitable hydrophobic fluid. In exemplary embodiments, the carrier fluid includes an oil (e.g., a fluorocarbon oil, a silicone oil, or the like) In some embodiments, the carrier fluid includes at least one surfactant. The droplets can be formed by a dispersed aqueous phase which can have any suitable density relative to the carrier fluid. For example, the aqueous phase can be less dense than the carrier fluid, such that the droplets are buoyant in the carrier fluid. In other embodiments, the aqueous phase can be more dense than the carrier fluid, such that the droplets sink in the carrier fluid. In other examples, the droplets may be dispersed throughout the carrier fluid. In some embodiments, the volume of the droplet mixture is from 11.2% to 100% of the vessel volume. In some embodiments, the volume of carrier fluid is from 0%-6% of the vessel volume. In some embodiments a head space volume is from 0% to 88.8% of the vessel volume.

In some embodiments, one or more droplets in the combined population of droplets is flowed through the mixing module at a flow rate from 1 μl/minute to 10000 μl/minute, wherein the flow rate is equal to [(droplets/time (minutes)) *(average droplet volume (up)].

In some embodiments, step (b) comprises laminar flow. In some embodiments, step (b) comprises turbulent flow. In some embodiments, the first population of droplets, second population of droplets, or combined droplet mixture has a Weber number of 1 or less. In some embodiments, the first population of droplets, second population of droplets, or combined droplet mixture has a Reynolds number of 2100 or less.

Also provided herein is a system for forming a droplet mixture, comprising: a droplet combining module comprising a first and a second population of droplets in a droplet mixture, a mixing module, and a pump, wherein a first droplet of the droplet mixture passes a second droplet of the droplet mixture when flowed through the mixing module, wherein at least one of the first and second population of droplets is formed prior to entering the combining module, and wherein 10% or more of the droplets in the droplet mixture remain intact after being flowed through the mixing module.

Also provided herein is a system for forming a droplet mixture, comprising: a droplet combining module comprising a first and a second population of droplets in a droplet mixture, a mixing module, a stabilizing module, and a pump wherein a first droplet of the droplet mixture passes a second droplet of the droplet mixture when flowed through the mixing module.

Also provided herein is a system for forming a droplet mixture, comprising: a droplet combining module comprising a first and a second population of droplets in a droplet mixture, a mixing module, a stabilizing module that is not a PCR amplification device, and a pump.

In some embodiments, the mixing module comprises a mixing channel. In some embodiments, the mixing channel has a nonlinear configuration. In some embodiments, the nonlinear configuration comprises at least one region of curvature. In some embodiments, the nonlinear configuration comprises at least one turn. In some embodiments, the nonlinear configuration is a serpentine configuration. In some embodiments, the mixing channel has a linear configuration. In some embodiments, the mixing channel comprises a length that affords mixing of droplets in the droplet mixture when flowed through the mixing channel due to buoyancy mismatch between droplets and a continuous phase or a carrier fluid around the droplets. In some embodiments, the mixing channel has a cross-sectional dimension from 1 time to 1000 times the average droplet diameter.

In some embodiments, the stabilizing module is operable to provide energy to the first population of droplets, the second population of droplets, droplet mixture, or any combination thereof. In some embodiments, the stabilizing module is operable to provide energy to the first population of droplets, the second population of droplets, or both, before formation of the droplet mixture. In some embodiments, the stabilizing module is operable to provide energy to the droplet mixture before, during or after being flowed through the mixing module. In some embodiments, the energy is thermal, electromagnetic, electrical, chemical, or mechanical energy, or any combination thereof. In some embodiments, the electromagnetic energy is gamma rays, x-rays, ultraviolet rays, visible light, infrared rays, microwaves, radio waves, or any combination thereof. In some embodiments, the thermal energy is heat, conduction, convection, or a combination thereof. In some embodiments, the stabilizing module comprises one or more heating element(s). In some embodiments, the one or more heating element comprises a resistive heating element, thermoelectric device, heating block, lamp, light source, microwave, radiation source, water bath, or any combination thereof. In some embodiments, two or more heating elements provide energy, thereby allowing for temperature cycling. In some embodiments, the energy initiates a reaction within the droplets. In some embodiments, the reaction comprises PCR, RT-PCR, isothermal amplification, in vitro translation, or a combination thereof. In some embodiments, the stabilizing module does not induce significant amplification of a signal within the droplets. In some embodiments, 50% or less of any of the droplets in the droplet mixture coalesce after being stabilized by the stabilizing module.

In some embodiments, the pump is operable to flow the droplets through the mixing module at a flow rate from 1 µl/minute to 10000 µl/minute. In some embodiments, the flow rate is equal to [(droplets/time (minutes))*(average droplet volume (µl))].

In some embodiments, the first population of droplets, second population of droplets, or droplet mixture has a Weber number of 1 or less. In some embodiments, the first population of droplets, second population of droplets, or combined droplet mixture has a Reynolds number of 2100 or less.

In some embodiments, the system further comprises a droplet generating module. In some embodiments, the droplet generating module comprises a first and a second droplet generator. In some embodiments, the first droplet generator partitions a sample into the first population of droplets and the second droplet generator partitions a sample into the second population of droplets.

In some embodiments, the first droplet generator and/or the second droplet generator comprises: a first reagent flow path in fluid communication with a sample reservoir, and a second reagent flow path in fluid communication with an oil reservoir, wherein the first reagent flow path and the second reagent flow path meet at an intersection that receives a sample from the sample reservoir and a carrier fluid from the oil reservoir and generates the one or more first droplets and/or the one or more second droplets, that are conveyed to the first droplet flow path or the second droplet flow path to the intersection.

In some embodiments, the intersection is in fluid communication with the combining module. In some embodiments, the intersection is upstream of the droplet combining module.

In some embodiments, the system further comprises a collection module operable to collect the droplet mixture after flowing through the mixing channel. In some embodiments, the collection module comprises a droplet reservoir downstream of the mixing channel.

In some embodiments, the mixing channel is in fluid communication with the droplet combining module. In some embodiments, the mixing channel is oriented along a direction that is parallel to a plane of the droplet combining module. In some embodiments, the mixing channel is oriented along a direction that is orthogonal to a plane of the droplet combining module.

Also provided herein is a composition, comprising a plurality of droplets, wherein the droplets comprise: an analyte that is detectably labeled; and an aqueous phase enclosed in a skin formed by heat-treating the droplet along a fluid flow path. In some embodiments, a frequency of off-amplitude events associated with the emission of a detectable signal from the plurality of droplets is 50% or less. In some embodiments, the skin has an area compressibility modulus from 0.01 mN/m to 10000 mN/m at a temperature of 25° C.

Also provided herein is a method, comprising the steps of:
a. partitioning a sample with a first droplet generator to produce a first droplet population;
b. partitioning a sample with a second droplet generator to produce a second droplet population;
c. combining the first droplet population and the second droplet population to produce a combination droplet population, wherein the combination droplet population is substantially uniform;
d. extracting a portion of the combined droplet population; and
e. detecting a signal from the combined droplet population, wherein the detecting step occurs at 0.5 hours or more after storing the combination droplet population.

Also provided herein is a method, comprising the steps of:
a. partitioning a sample with a first droplet generator to produce a first droplet population;
b. partitioning a sample with a second droplet generator to produce a second droplet population;

c. combining the first droplet population and the second droplet population to produce a combination droplet population, wherein the combination droplet population is substantially uniform;

d. extracting a portion of the combined droplet population; and e. detecting a signal from the combined droplet population; wherein the detecting step is performed after transport of the first droplet population, second droplet population, combination droplet population, or a combination thereof, a distance of 1 km or more.

In some embodiments, the signal degrades 50% or less after transport of the first droplet population, second droplet population, combined droplet steam, or any combination thereof, over a distance of 1 km or more. In some embodiments, wherein the signal degrades 50% or less after storage of the first droplet population, second droplet population, combined droplet steam, or any combination thereof, for 0.5 hours or more. In some embodiments, a signal can be detected in 10% or more of the total number of droplets after transport of the first droplet population, second droplet population, combined droplet steam, or any combination thereof, over a distance of 1 km or more. In some embodiments, a signal can be detected in 10% or more of the total number of droplets after storage of the first droplet population, second droplet population, combined droplet population, or any combination thereof, for 0.5 hours or more.

In some embodiments, the method further comprises stabilizing one or more droplets of the first droplet population, second droplet population, combined droplet population, or any combination thereof. In some embodiments, stabilizing comprises providing energy. In some embodiments, the energy is thermal, electromagnetic, electrical, chemical, or mechanical energy, or any combination thereof. In some embodiments, the electromagnetic energy is gamma rays, x-rays, ultraviolet rays, visible light, infrared rays, microwaves, radio waves, or any combination thereof. In some embodiments, the thermal energy is heat, conduction, convection, radiation, or a combination thereof. In some embodiments, the energy is provided by one or more heating element(s). In some embodiments, the one or more heating element comprises a resistive heating element, thermoelectric device, heating block, lamp, light source, microwave, radiation source, water bath, or any combination thereof. In some embodiments, the stabilizing does not induce significant amplification of a signal. In some embodiments, 50% or less of the droplets in the first droplet population, second droplet population, and combined droplet population coalesce after stabilizing.

In some embodiments, the method further comprises a step of mixing the combined droplet population, wherein a first droplet of the combined droplet population flows past a second droplet of the combined droplet population. In some embodiments, the mixing step is performed within a mixing module. In some embodiments, the mixing module is a mixing channel. In some embodiments, the mixing channel has a nonlinear configuration. In some embodiments, the nonlinear configuration comprises at least one region of curvature. In some embodiments, the nonlinear configuration comprises at least one turn. In some embodiments, the nonlinear configuration is a serpentine configuration. In some embodiments, the mixing channel has a linear configuration. In some embodiments, the mixing channel comprises a length that affords mixing due to buoyancy mismatch between droplets and a continuous phase or a carrier fluid around the droplets. In some embodiments, the mixing channel has a cross-sectional dimension from 1 time to 1000 times the average droplet diameter.

Also provided herein is a method of mixing droplets, comprising the steps of:

a. combining at least a portion of a first population of droplets with at least a portion of a second population of droplets to form a combined population of droplets; and b. mixing the combined population of droplets in a mixing module; wherein 10% or more of the droplets in the combined droplet population remain intact after mixing, and wherein the mixing module is moved, rotated, rocked, shook, or vibrated.

Also provided herein is a method of mixing droplets, comprising the steps of:

a. combining at least a portion of a first population of droplets with at least a portion of a second population of droplets to form a combined population of droplets; and b. mixing the combined population of droplets in a mixing module; wherein 10% or more of the droplets in the combined droplet population remain intact after mixing, and wherein the mixing module is not in fluid communication with a droplet generator used to generate said first or second population of droplets.

DETAILED DESCRIPTION

The present disclosure provides systems, including devices and methods, utilizing two or more droplet generators to produce uniform mixtures of droplets. The droplet mixtures can have many uses, such as calibration standards, instrument calibration standards, or general standards. The standards can be labeled with one or more dyes or indicators. The methods described herein can involve preparing two or more samples, such as a standard, calibration, clinical, or environmental samples, for analysis or instrument calibration; separating components of each of the samples by partitioning them into droplets or other partitions; combining the droplets from each sample to form a droplet mixture; mixing the droplet mixture; optionally heating the droplet mixture, and collecting the droplet mixture.

In general, a single droplet generator may have a limited droplet generating capacity. To generate a large numbers of droplets in a given time, such as to increase throughput, two or more droplet generators can be run in parallel. Droplet generators may produce droplets that differ in one or more characteristics, such as size and shape among others. When individual droplet generators produce droplets that differ in one or more characteristics, there may be a need to mix the output droplet populations or sub-populations of two or more droplet generators to provide a bulk droplet mix that is substantially homogeneously mixed, and/or substantially uniform. Mixing multiple droplet populations not only increases throughput, but also allows for thoroughly mixed droplet populations with various "positive" and "negative" populations for simulating concentrations of reagents, such as DNA and fluorophores, or for checking color calibration and/or compensation. Simulated concentrations can be produced using the systems and methods described herein by mixing simulated positive (high fluorescence amplitude) and negative (low fluorescence amplitude) droplets.

The systems described herein can be used to generate scalable droplet mixtures from one or more droplet populations, such as multiple populations, or sub-populations. The systems can be used for automated (user-independent) or manual droplet generation of scalable volumes of one or more populations of droplets, with options to add additional mixing and thermal control features. A population of droplets can be a plurality of droplets produced from a source, such as a droplet generator. A first population of droplets can be a first plurality of droplets produced from a first droplet generator and a second population of droplets can be a second plurality of droplets produced from a second droplet generator. In some embodiments, the first droplet generator can be different from the second droplet generator. For example, a first droplet generator can be located at a different site than a second droplet generator or a first droplet generator can be located at the same site as a second droplet generator, such as when the two populations of droplets are produced at substantially the same time or different times. In some embodiments, the first droplet generator can be the same as the second droplet generator. For example, a first population of droplets can be produced from a first droplet generator at one time and a second population of droplets can be produced from a second droplet generator at a different time, wherein the first and second droplet generators are the same. In some embodiments, the systems can be used for automated in-line mixing of scalable volumes of two or more populations or streams of droplets. Flow-induced mixing can remove variability in the mixing process and can create uniform mixtures while better preserving droplet integrity than conventional techniques such as pipetting or vortexing. In some embodiments, the systems can be used for off-line mixing of scalable volumes of two or more populations or streams of droplets, such as off-line mixing with stirred pots or rocker plates, to achieve more uniform droplet mixtures than conventional techniques. For example, mixing can be accomplished by moving, rotating, shaking, or vibrating a mixing module containing droplets. Additionally, the systems can be used to mix droplets while reducing the amount of coalescence, shearing, breakage, and/or damage that can occur using more conventional mixing techniques. Thus, the systems provided herein can provide accurate and precise solutions to generating standards of mixed droplet populations with known concentrations.

The systems may use pressure driven flow, such as positive or negative pressure, via use of pumps, such as syringe pumps. The systems may also include tubing or a mechanical tube guide, such as in the form of serpentine pattern that promotes droplet mixing, such as axial or turbulent mixing, within the tubing.

System Overview/Architecture

This section provides illustrative systems and devices for generating and mixing droplet populations or streams generated from two or more droplet generators. The features and aspects of the systems disclosed in this section may be combined with one another and/or with any suitable aspects and features of methods and apparatus shown and/or described elsewhere in the present disclosure.

Any of the systems described herein can comprise a fluidic network of channels arranged to be operable to produce a mixture of two or more droplet populations. Any of the systems described herein can comprise a fluidic network of channels arranged to produce two or more droplet populations or streams, which can be mixed to form a droplet mixture.

A channel can be an elongated passage or flow path for droplet and/or fluid travel. A channel generally includes at least one inlet, where fluid enters the channel, and at least one outlet, where fluid exits the channel. The functions of the inlet and the outlet may be interchangeable, that is, fluid may flow through a channel in only one direction or in opposing directions, generally at different times. A channel may include walls that define and enclose the passage between the inlet and the outlet. A channel may, for example, be formed by a tube (e.g., a capillary tube), in or on a planar structure (e.g., a chip), or a combination thereof, among others. A channel may or may not branch. A channel may be linear or nonlinear. Exemplary nonlinear channels include a channel extending along a planar flow path (e.g., a serpentine channel) or a channel that extends along a nonplanar flow path (e.g., a helical channel to provide a helical flow path). Any of the channels disclosed herein may be a microfluidic channel, which is a channel having a characteristic transverse dimension (e.g., the channel's average diameter) of less than about one millimeter. Any of the channels disclosed herein may have a characteristic transverse dimension (e.g., the channel's average diameter) of more than about one millimeter. Any of the channels disclosed herein may be designed to allow for active, passive, laminar, turbulent, or axial mixing of droplets within the channel. Channels also may include one or more venting mechanisms to allow droplets and/or fluid to enter/exit without the need for an open outlet. Examples of venting mechanisms include but are not limited to hydrophobic vent openings or the use of porous materials to either make up a portion of the channel or to block an outlet if present.

A fluidics network can be an assembly for manipulating droplets and/or fluid, generally by transferring droplets and/or fluid between compartments of the assembly and/or by driving flow of droplets and/or fluid along and/or through one or more flow paths defined by the assembly. A fluidics network may include any suitable structure, such as one or more channels, chambers, reservoirs, obstacles, valves, pumps, thermal control devices (e.g., heaters/coolers), sensors (e.g., for measuring temperature, pressure, flow, etc.), or any combination thereof, among others.

Any of the systems described herein can comprise a droplet generating device which can comprise one or more droplet generators, a fluidic network of channels, a mixing module, a stabilization module, a sample preparation module, a collection module, and one or more sample cartridges that connect to an instrument, to provide sample preparation, sample/droplet flow, and/or droplet mixing and heating that can be actuated and controlled by the instrument.

Referring to FIG. 1, System 100 can optionally include a droplet generating module 101 and a mixing module 102. In some embodiments the droplet generating module 101 and mixing module 102 are in fluid connection. In some embodiments the droplet generating module 101 and mixing module 102 are not in fluid connection.

System 100 can include a first droplet generator 110 and a second droplet generator 120. The first droplet generator 110 may or may not be part of a microfluidic chip 150. The second droplet generator 120 may or may not be part of a microfluidic chip. The first and second droplet generators may or may not be parts of the same microfluidic chip 150. The first and second droplet generators 110 and 120 can include a first droplet channel 111 and a second droplet channel 121, which can be arranged such that a first droplet channel 111 of the first droplet generator intersects with a second droplet channel 121 of the second droplet generator. The intersection 130 of the droplet channels 111 and 112 can be downstream of the droplet generators. The intersection 130 can be operable to receive droplets from the droplet channels 111 and 121. Droplets originating from the droplet channels 111 and 121 can flow into the intersection 130 and can result in the formation of a combined droplet population.

In some embodiments, system 100 can comprise more than two droplet generators, each comprising one or more channels. For example, a system can comprise 3, 4, 5, 6, 7, 8, 9, 10, or more droplet generators, each with one or more droplet channels. In some embodiments, the one or more channels of the two or more droplet generators intersect with the other one or more channels of the two or more droplet generators. For example, one or more channels of a first droplet generator can intersect with one or more channels of a second droplet generator.

In some embodiments, a mixing module 102 can include a droplet combining module 131 and a mixing channel 140. In some embodiments, a mixing module 102 can include a mixing channel 140 and not include a droplet combining module 131. A mixing channel 140 can be situated downstream of the intersection 130.

Figure 4:
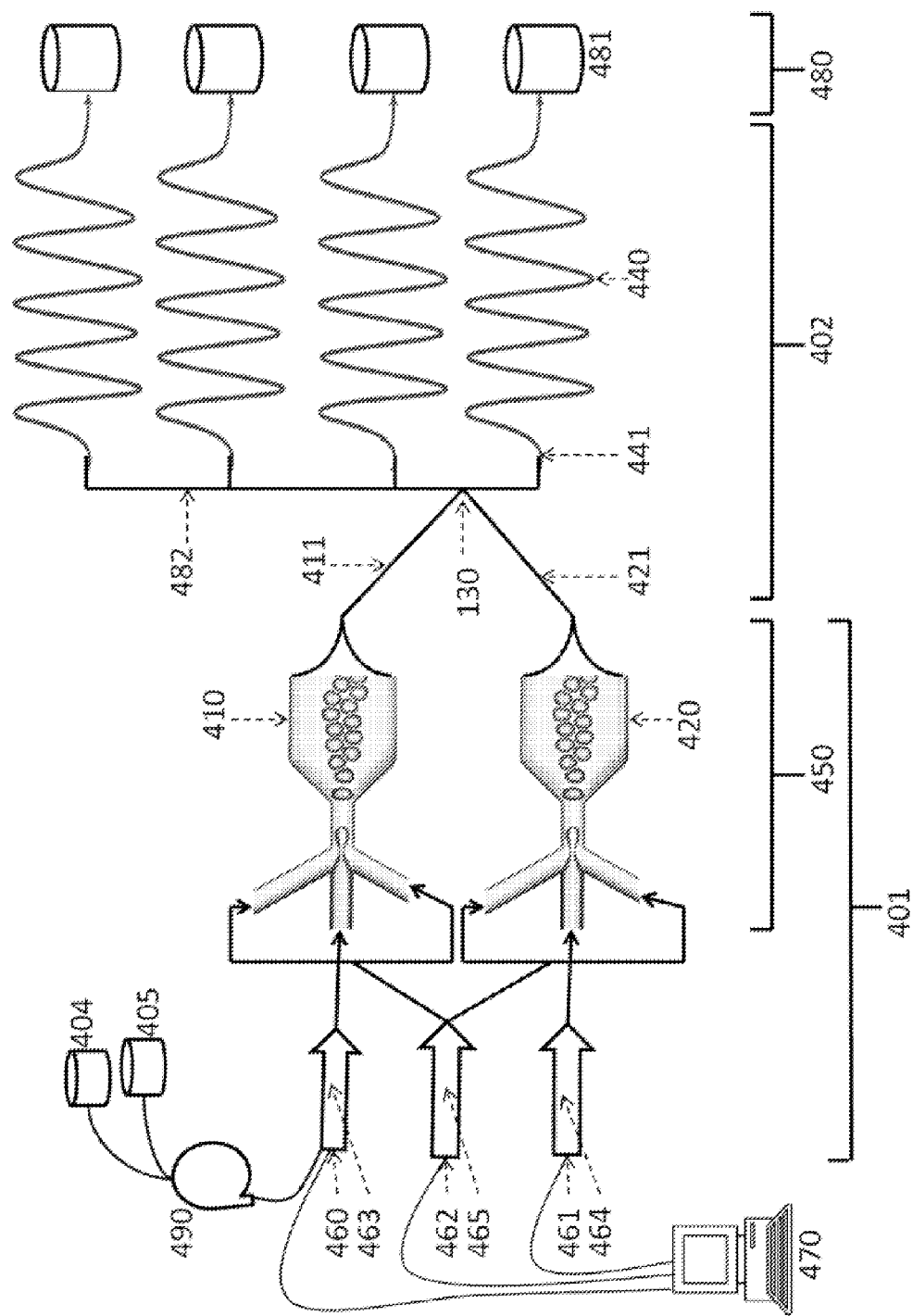
FIG. 4 is an exemplary droplet generating and mixing system.

In some embodiments, a system can comprise one or more mixing channels. For example, a system can comprise 2, 3, 4, 5, 6, 7, 8, 9, 10, or more mixing channels as shown in FIG. 4.

In some embodiments, a mixing module 102 can include a droplet combining module 131 downstream of the intersection 130 of the first and second droplet channels 111 and 121. The droplet combining module 131 can be upstream of the mixing channel 140. In some embodiments, a droplet combining module 131 can be the intersection 130 of the first and second droplet channels 111 and 121. A droplet combining module may combine two or more droplet populations or streams. If there are three or more droplet populations or streams, they may be combined with a single droplet combining module, or they may be combined with a plurality of droplet combining modules. In some embodiments, for any of the systems described herein, a droplet combining module 131 can be in fluid communication with a mixing module 102. In some embodiments, for any of the systems described herein, a droplet combining module 131 may not be in fluid communication with a mixing module 102. This can allow for droplet populations to be combined off-line, such as before flowing the combined droplet populations through a mixing module 102.

System 100 can include a first pump 160, a second pump 161, and a third pump 162 for advancing droplets through system 100 for droplet formation, flow, mixing, or any combination thereof. As shown in FIG. 1, a first pump 160 can be operable to advance a first solution 163, such as a first dye or assay mixture, through system 100 for droplet formation, flow, mixing, or any combination thereof. As shown in FIG. 1, a second pump 161 can be operable to advance a second solution 164, such as a second dye or assay mixture, through system 100 for droplet formation, flow, mixing, or any combination thereof. As shown in FIG. 1, a third pump 162 can be operable to advance an immiscible solution 165, such as oil, through system 100 for droplet formation, flow, mixing, or any combination thereof.

In some embodiments, a first 163 and/or second solution 164, and/or an immiscible solution 165, can be each controlled by one or more of the same or different pump. In some embodiments, any of the reservoirs containing a first 163 and/or second solution 164, and/or an immiscible solution 165, can be shared or in fluid communication with two or more droplet generators. For example, a reservoir containing an immiscible solution 165, can be shared or in fluid communication with two or more droplet generators. In some embodiments, any of the reservoirs containing a first 163 and/or second solution 164, and/or an immiscible solution 165 may not be shared or in fluid communication with two or more droplet generators. For example, a first solution 163 can be in fluid communication with a first droplet generator and not a second droplet generator and a second solution 164 can be in fluid communication with the second droplet generator and not the first droplet generator. As another example, a first solution 163 and an immiscible solution 165 can both be in fluid communication with a first droplet generator, wherein the first solution 163 is not in fluid communication with a second droplet generator; and a second solution 164 and the immiscible solution 165 can both be in can be in fluid communication with the second droplet generator, wherein the second solution 164 is not in fluid communication with the first droplet generator.

Any of the pumps can be controlled by a computer 170 or can be controlled manually. In one embodiment, computer 170 can be a general-purpose computer including a memory, or other suitable computer-readable medium, for storing program instructions for operating pumps 160, 161, and 162. Alternatively, computer 170 can include a disk drive, compact disc drive, or other suitable component for reading instructions contained on a computer-readable medium for operating pump 160. Computer 170 can include instructions for receiving, analyzing, and displaying information for controlling the pumps 160, 161, and 162. Computer 170 can also include a display, mouse, keyboard, printer, or other suitable components known to those of skill in the art for receiving and displaying information to an operator. In some cases, pressure driven flow, such as positive or negative pressure, (e.g., via use of pumps, such as syringe pumps), is used to guide droplets through tubing or a mechanical tube guide. In some embodiments, the tubing has a serpentine pattern.

Figure 3:
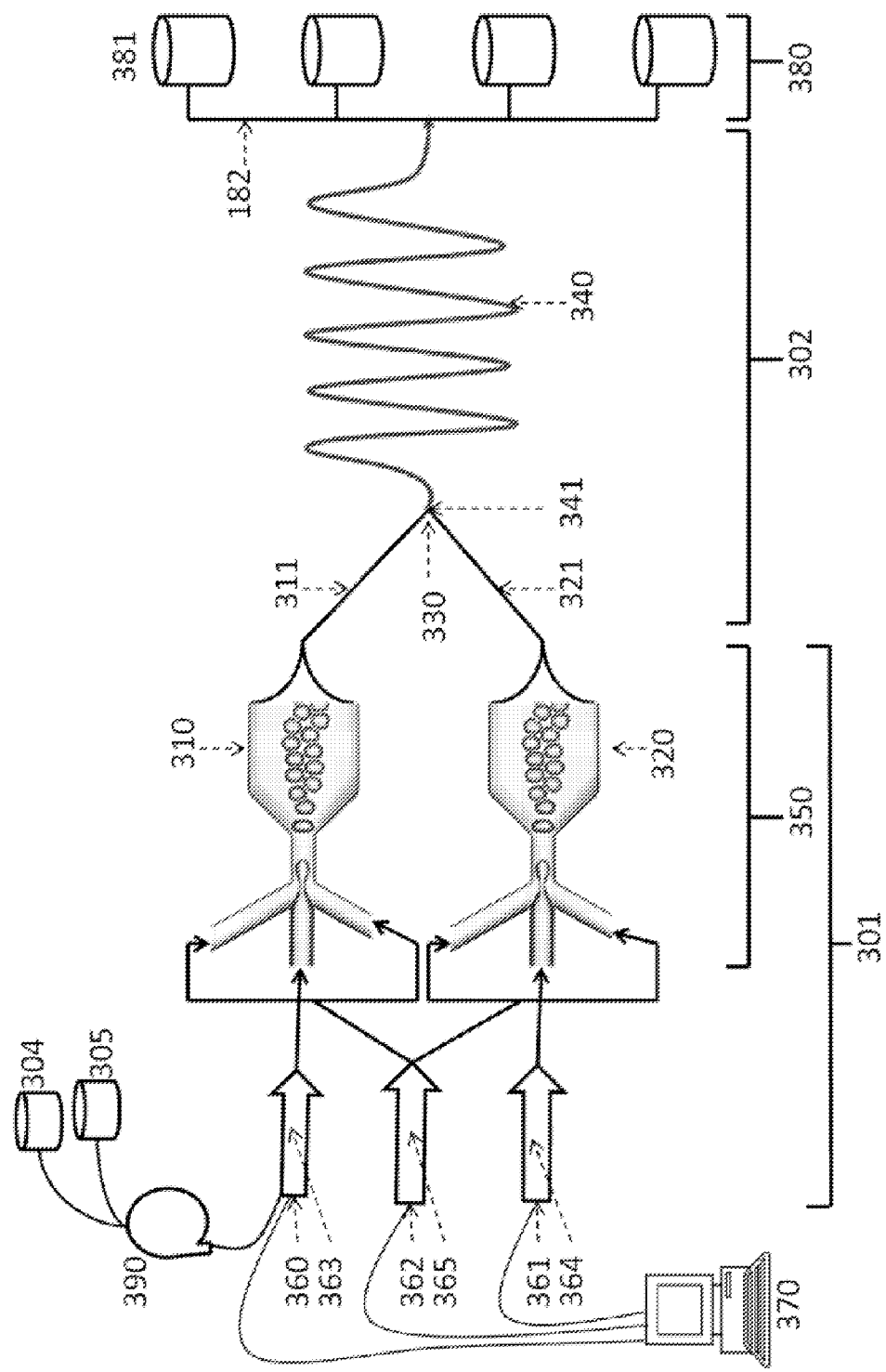
FIG. 3 is an exemplary droplet generating and mixing system.

System 100 can include a collection module 180. A collection module 180 can be located downstream of mixing channel 140 and can comprise one or more collection vessels 181. In some embodiments, a manifold or other multiport/splitter device 182 can be implemented prior to collection to distribute droplets into various volumes or collection vessels as shown in FIG. 3.

System 100 can include one or more sample mixers 190 and a two or more droplet generators 110 and 120. Sample mixer 190 may receive a sample 104 and at least one reagent 105 and combine them to form an assay mixture. The sample mixer may be an automated device, or mixing can be performed manually by a user, such as by bulk mixing, before loading two or more assay mixtures into the pumps 160, 161, and 162 for droplet generators 110 and 120. Droplet generators 110 and 120 can receive the assay mixtures from the mixer 190 and generate two or more emulsions of droplets in an immiscible carrier fluid, such as oil that is introduced into the droplet generators, at the same time as the assay mixture. Droplet generators 110 and 120 can receive the assay mixtures from the same mixer 190 or from different mixers. Formation of droplets may be driven by pressure, pumping, or a combination thereof. In some examples, the droplet generator can function as a mixer by generating droplets from confluent streams of sample and reagent. System 100 may have any suitable number of droplet generators. The droplet generators in any of the systems described herein may be used to generate any suitable number of separate, distinct emulsions from one sample or a plurality of samples, and from one reagent or a plurality of reagents, such as reagents for different species of nucleic acid target, multiple dye types that vary spectrally, and/or one or more dyes of various concentrations.

Figure 2:
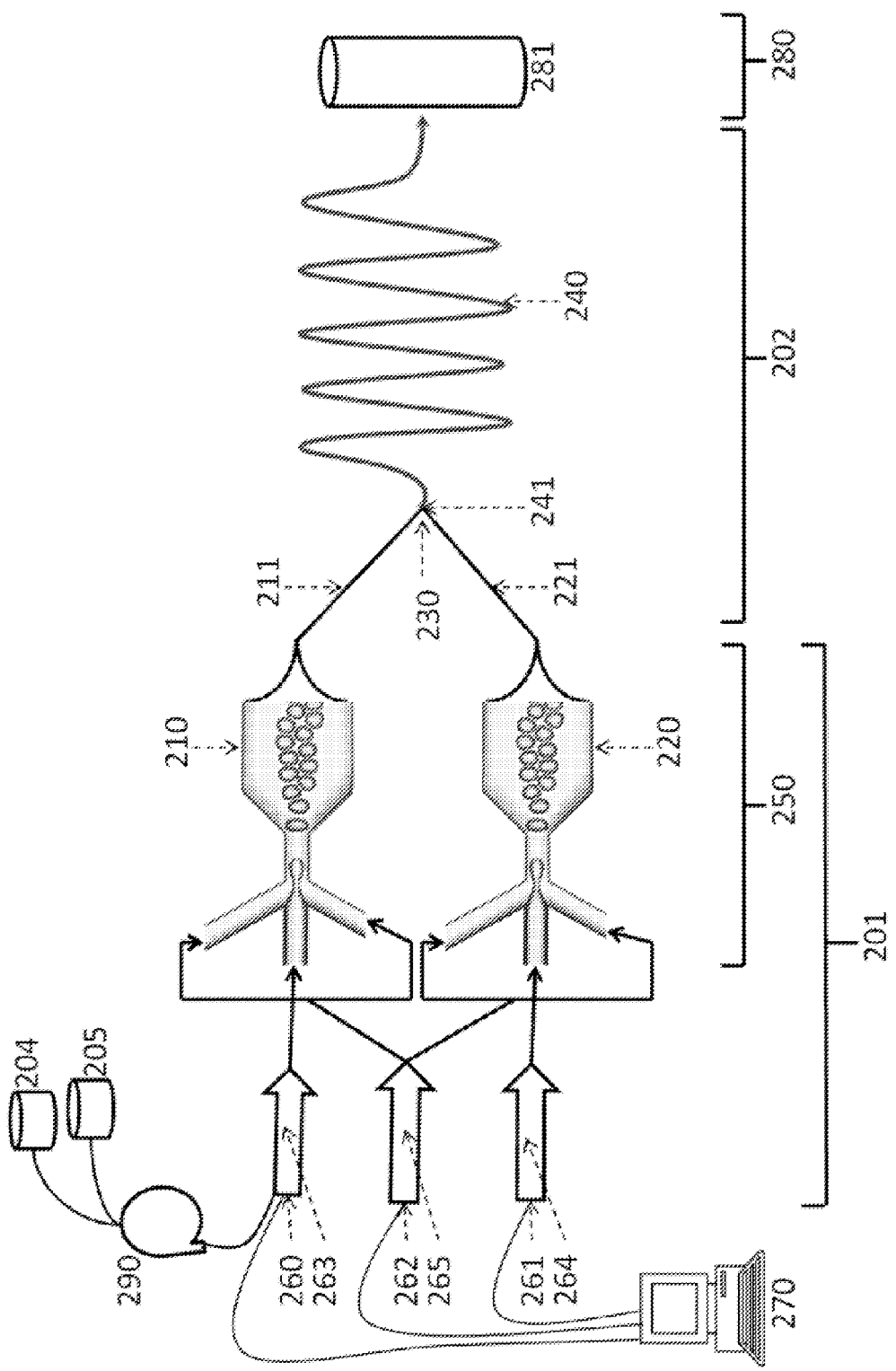
FIG. 2 is an exemplary droplet generating and mixing system.

Another exemplary microfluidic system 200 for producing mixtures of droplets is depicted in FIG. 2. System 200 can optionally include a droplet generating module 201 and a mixing module 202. In some embodiments the droplet generating module 201 and mixing module 202 are in fluid connection. In some embodiments the droplet generating module 201 and mixing module 202 are not in fluid connection.

System 200 can include a first droplet generator 210 and a second droplet generator 220. The first droplet generator 210 may or may not be part of a microfluidic chip 250. The second droplet generator 220 may or may not be part of a microfluidic chip. The first and second droplet generators may or may not be parts of the same microfluidic chip 250. The first and second droplet generators 210 and 220 can include a first droplet channel 211 and a second droplet channel 221, which can be arranged such that a first droplet channel 211 of the first droplet generator intersects with a second droplet channel 221 of the second droplet generator. The intersection 230 of the droplet channels 211 and 221 can be downstream of the droplet generators. The intersection 230 can be operable to receive droplets from the droplet channels 211 and 221. Droplets originating from the droplet channels 211 and 221 can flow into the intersection 230 and can result in the formation of a mixture of droplets.

In some embodiments, system 200 can comprise more than two droplet generators, each comprising one or more channels. For example, a system can comprise 3, 4, 5, 6, 7, 8, 9, 20, or more droplet generators, each with one or more droplet channels. In some embodiments, the one or more channels of the two or more droplet generators intersect with the other one or more channels of the two or more droplet generators. For example, one or more channels of a first droplet generator intersect with one or more channels of a second droplet generator.

System 200 can include a mixing module 202, which includes a mixing channel 240, and in some embodiments, does not include a droplet combining module (131 as shown in FIG. 1). A mixing channel 240 can be situated downstream of the intersection 230. A mixing channel 240 can meet at intersection 230 at one end of the mixing channel 241.

In some embodiments, a system 200 can comprise one or more mixing channels 240, each situated downstream of the intersection 230. For example, a system can comprise 2, 3, 4, 5, 6, 7, 8, 9, 10, or more mixing channels each situated downstream of intersection 230 as shown in FIG. 4.

System 200 can include a first pump 260, a second pump 261, and a third pump 262 for advancing droplets through system 200 for droplet formation, flow, mixing, or any combination thereof. As shown in FIG. 2, a first pump 260 can be operable to advance a first solution 263, such as a first assay mixture, through system 200 for droplet formation, flow, mixing, or any combination thereof. As shown in FIG. 2, a second pump 261 can be operable to advance a second solution 264, such as a second assay mixture, through system 200 for droplet formation, flow, mixing, or any combination thereof. As shown in FIG. 2, a third pump 262 can be operable to advance an immiscible solution 265, such as oil, through system 200 for droplet formation, flow, mixing, or any combination thereof.

In some embodiments, a first 263 and/or second solution 264, and/or an immiscible solution 265, can be each controlled by one or more of the same or different pump. In some embodiments, any of the reservoirs containing a first 263 and/or second solution 264, and/or an immiscible solution 265, can be shared or in fluid communication with two or more droplet generators. For example, a reservoir containing an immiscible solution 265, can be shared or in fluid communication with two or more droplet generators. In some embodiments, any of the reservoirs containing a first 263 and/or second solution 264, and/or an immiscible solution 265 may not be shared or in fluid communication with two or more droplet generators. For example, a first solution 263 can be in fluid communication with a first droplet generator and not a second droplet generator and a second solution 264 can be in fluid communication with the second droplet generator and not the first droplet generator. As another example, a first solution 263 and an immiscible solution 265 can both be in fluid communication with a first droplet generator, wherein the first solution 263 is not in fluid communication with a second droplet generator; and a second solution 264 and the immiscible solution 265 can both be in can be in fluid communication with the second droplet generator, wherein the second solution 264 is not in fluid communication with the first droplet generator.

Any of the pumps can be controlled by a computer 270 or can be controlled manually. In one embodiment, computer 270 can be a general-purpose computer including a memory, or other suitable computer-readable medium, for storing program instructions for operating pumps 260, 261, and 262. Alternatively, computer 270 can include a disk drive, compact disc drive, or other suitable component for reading instructions contained on a computer-readable medium for operating pumps 260, 261, and 262. Computer 270 can include instructions for receiving, analyzing, and displaying information for controlling the pumps 260, 261, and 262. Computer 270 can also include a display, mouse, keyboard, printer, or other suitable component known to those of skill in the art for receiving and displaying information to an operator. One embodiment uses pressure driven flow, such as positive or negative vacuum pressure, via use of pumps, such as syringe pumps, and tubing or a mechanical tube guide to make a serpentine pattern that causes droplets to mix within the tubing under pressure-driven flow.

System 200 can include a collection module 280. A collection module 280 can be located downstream of mixing channel 240 and can comprise one or more collection vessels 281. In some embodiments, a manifold or other multiport/splitter devices can be implemented prior to collection to distribute droplets into various volumes or collection vessels as shown in FIG. 3.

In some embodiments, a mixing module 202 does not include a droplet combining module (131 as shown in FIG. 1) downstream of the intersection 230 of the first and second droplet channels 211 and 221. The droplet combining module (131 as shown in FIG. 1) can be upstream of the mixing channel 240. In some embodiments, a droplet combining module (131 as shown in FIG. 1) can be the intersection 230 of the first and second droplet channels 211 and 221. In some embodiments, for any of the systems described herein, a droplet combining module 131 can be in fluid communication with a mixing module 202. In some embodiments, for any of the systems described herein, a droplet combining module 131 may not be in fluid communication with a mixing module 202. This can allow for droplet populations to be combined off-line, such as before flowing the combined droplet populations through a mixing module 202.

System 200 may include one or more mixers 290 and a two or more droplet generators 210 and 220. Mixer 290 may receive a sample 204 and at least one reagent 205 and combine them to form an assay mixture. The mixer may be an automated device, or mixing can be performed manually by a user, such as by bulk mixing, before loading two or more assay mixtures into the pumps 260 and 261 for droplet generators 210 and 220. Droplet generators 210 and 220 can receive the assay mixtures from the mixer 290 and generate two or more emulsions of droplets in an immiscible carrier fluid, such as oil that is introduced into the droplet generators, at the same time as the assay mixture. Formation of droplets may be driven by pressure, pumping, or a combination thereof. In some examples, the droplet generator can function as a mixer by generating droplets from confluent streams of sample and reagent. System 200 may have any suitable number of droplet generators. The droplet generators may be used to generate any suitable number of separate, distinct emulsions from one sample or a plurality of samples, and from one reagent or a plurality of reagents, such as reagents for different species of nucleic acid target.

Another exemplary microfluidic system 300 for producing mixtures of droplets is depicted in FIG. 3. System 300 can include a droplet generating device 301 and a mixing device 302. In some embodiments the droplet generating device 301 and mixing device 302 are in fluid connection. In some embodiments the droplet generating device 301 and mixing device 302 are not in fluid connection. In many respects, system 300 is similar to the systems depicted in FIGS. 1 and/or 2; and the features described for those systems can generally equally apply to this system.

In some embodiments, a mixing module 302 does not include a droplet combining module (131 as shown in FIG. 1) downstream of the intersection 330 of the first and second droplet channels 311 and 321. The droplet combining module (131 as shown in FIG. 1) can be upstream of the mixing channel 340. In some embodiments, a droplet combining module (131 as shown in FIG. 1) can be the intersection 330 of the first and second droplet channels 311 and 321. In some embodiments, for any of the systems described herein, a droplet combining module 131 can be in fluid communication with a mixing module 302. In some embodiments, for any of the systems described herein, a droplet combining module 131 may not be in fluid communication with a mixing module 302. This can allow for droplet populations to be combined off-line, such as before flowing the combined droplet populations through a mixing module 302.

System 300 can include a droplet mixture collection module 380. A droplet mixture collection module 380 can be located downstream of mixing channel 340 and can comprise one or more collection vessels 381. System 300 can include a manifold 382 or other multiport/splitter devices that can be implemented prior to collection of droplet mixtures to distribute droplets into various volumes or collection vessels.

In some embodiments, a first 363 and/or second solution 364, and/or an immiscible solution 365, can be each controlled by one or more of the same or different pump. In some embodiments, any of the reservoirs containing a first 363 and/or second solution 364, and/or an immiscible solution 365, can be shared or in fluid communication with two or more droplet generators. For example, a reservoir containing an immiscible solution 365, can be shared or in fluid communication with two or more droplet generators. In some embodiments, any of the reservoirs containing a first 363 and/or second solution 364, and/or an immiscible solution 365 may not be shared or in fluid communication with two or more droplet generators. For example, a first solution 363 can be in fluid communication with a first droplet generator and not a second droplet generator and a second solution 364 can be in fluid communication with the second droplet generator and not the first droplet generator. As another example, a first solution 363 and an immiscible solution 365 can both be in fluid communication with a first droplet generator, wherein the first solution 363 is not in fluid communication with a second droplet generator; and a second solution 364 and the immiscible solution 365 can both be in can be in fluid communication with the second droplet generator, wherein the second solution 364 is not in fluid communication with the first droplet generator.

Another exemplary microfluidic system 400 for producing mixtures of droplets is depicted in FIG. 4. System 400 can include a droplet generating device 401 and a mixing device 402. In some embodiments the droplet generating device 401 and mixing device 402 are in fluid connection. In some embodiments the droplet generating device 401 and mixing device 402 are not in fluid connection. In many respects, system 400 is similar to the systems depicted in FIGS. 1 and/or 2; and the features described for those systems can generally equally apply to this system.

In some embodiments, a mixing device 402 can include a droplet combining module (as shown in FIG. 1) and more than one mixing channels 440. For example, a system can comprise 2, 3, 4, 5, 6, 7, 8, 9, 10, or more mixing channels each situated downstream of intersection 440. In some embodiments, a mixing device 402 can include more than one mixing channels 440 and not include a droplet combining module (131 as shown in FIG. 1). Mixing channels 440 can be situated downstream of the intersection 130. In such embodiments, a manifold 482 or other multiport/splitter devices can be implemented upstream of the mixing channels 440 and downstream of intersection 130 prior to collection to mix droplets in multiple mixing channels 440 as shown in FIG. 4 and be operable to split a droplet mixture into the multiple mixing channels 440. Manifold 482 can meet at intersection 130 at one end of each mixing channel 441.

In some embodiments, a mixing module 402 can include a droplet combining module (131 as shown in FIG. 1) downstream of the intersection 130 of the first and second droplet channels 411 and 421 and upstream of manifold 482. The droplet combining module (as shown in FIG. 1) can be upstream of the mixing channels 440. In some embodiments, a droplet combining module (as shown in FIG. 1) can be the intersection 440 of the first and second droplet channels 411 and 421. In some embodiments, for any of the systems described herein, a droplet combining module 131 can be in fluid communication with a mixing module 402. In some embodiments, for any of the systems described herein, a droplet combining module 131 may not be in fluid communication with a mixing module 402. This can allow for droplet populations to be combined off-line, such as before flowing the combined droplet populations through a mixing module 402.

System 400 may include one or more mixers 490 and a two or more droplet generators 410 and 420. Mixer 490 may receive a sample 404 and at least one reagent 405 and combine them to form an assay mixture. The mixer may be an automated device, or mixing can be performed manually by a user, such as by bulk mixing, before loading two or more assay mixtures into the pumps 460, 461, and 462 for droplet generators 410 and 420. Droplet generators 410 and 420 can receive the assay mixtures from the mixer 490 and generate two or more emulsions of droplets in an immiscible carrier fluid, such as oil that is introduced into the droplet generators, at the same time as the assay mixture. Formation of droplets may be driven by pressure, pumping, or a combination thereof. In some examples, the droplet generator can function as a mixer by generating droplets from confluent streams of sample and reagent. System 400 may have any suitable number of droplet generators. The droplet generators may be used to generate any suitable number of separate, distinct emulsions from one sample or a plurality of samples, and from one reagent or a plurality of reagents, such as reagents for different species of nucleic acid target.

In some embodiments, a first 463 and/or second solution 464, and/or an immiscible solution 465, can be each controlled by one or more of the same or different pump. In some embodiments, any of the reservoirs containing a first 463 and/or second solution 464, and/or an immiscible solution 465, can be shared or in fluid communication with two or more droplet generators. For example, a reservoir containing an immiscible solution 465, can be shared or in fluid communication with two or more droplet generators. In some embodiments, any of the reservoirs containing a first 463 and/or second solution 464, and/or an immiscible solution 465 may not be shared or in fluid communication with two or more droplet generators. For example, a first solution 463 can be in fluid communication with a first droplet generator and not a second droplet generator and a second solution 464 can be in fluid communication with the second droplet generator and not the first droplet generator. As another example, a first solution 463 and an immiscible solution 465 can both be in fluid communication with a first droplet generator, wherein the first solution 463 is not in fluid communication with a second droplet generator; and a second solution 464 and the immiscible solution 465 can both be in can be in fluid communication with the second droplet generator, wherein the second solution 464 is not in fluid communication with the first droplet generator.

Any of the systems described herein can include at least one packing feature to increase the concentration of droplets. The packing feature may increase the volume fraction of an emulsion occupied by droplets, which can, for example, be desirable to decrease the amount of energy spent on heating a carrier fluid, to increase the rate at which droplets in a droplet mixture are deposited into a collection vessel, and/or to increase the number of droplets in a droplet mixture that can be mixed by a mixing module or stabilized simultaneously by a stabilization module or a heating element. A suitable concentration of droplets ("packing density") can be achieved during droplet generation or the packing density can be increased after droplet generation. An increase in packing density can be achieved by removing carrier fluid from an emulsion, while the emulsion is static, such as during storage, or flowing, and/or by selective intake of droplets from a stored emulsion, among others. Droplets can be concentrated locally in a stored emulsion by centrifugation, gravity coupled with a density difference between the droplets and the carrier fluid, electrokinetic concentration of droplets, magnetic concentration of droplets, or any combination thereof. The packing density can be increased during flow by using one or more side vent lines of smaller diameter (or one or more membranes) that selectively permit lateral flow and removal of carrier fluid. Alternatively, or in addition, the packing density can be increased during fluid flow by utilizing droplet inertia.

Work Flow Steps

Figure 5:
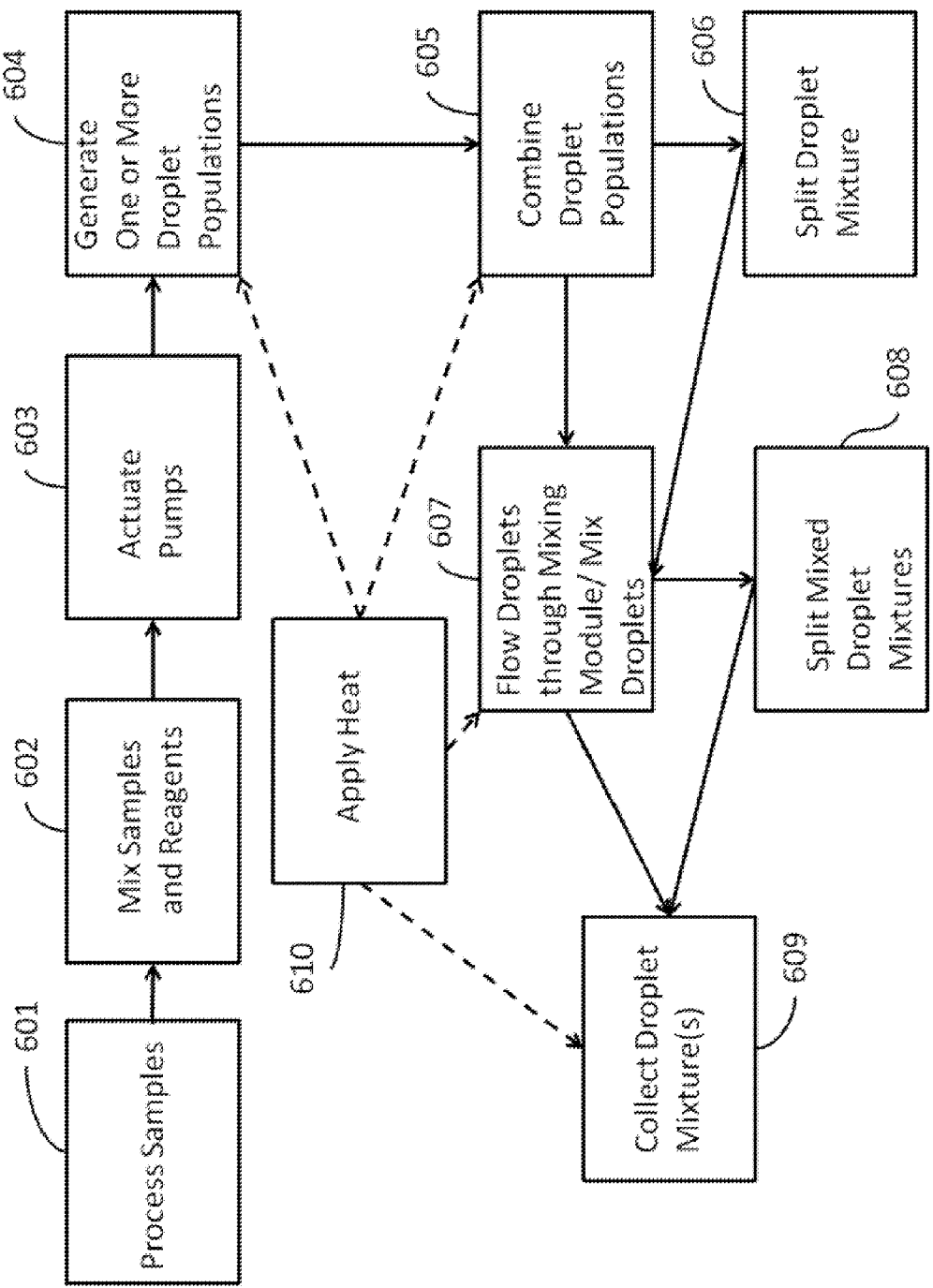
FIG. 5 is a schematic view of an exemplary sequence of processes performed by the systems described herein.

A schematic of a typical sequence of processes performed by the systems described herein is depicted in FIG. 5. Any of the steps depicted in FIG. 5 can be optional as appropriate. One or more samples or analytes, such as fluorescent dyes, can be processed 601 (e.g., by lysis, etc.) and mixed with reagents 602 useful for performing downstream analyses or tests, such as PCR reagents. The pumps of the system can be operated 603, either manually or by a computer, leading to flow of each of the sample/reagent mixtures through the system toward separate droplet generators. A pump operable to control the flow of an immiscible fluid, such as oil, can also be operated 603, either manually or by a computer, leading to flow of the immiscible fluid toward two or more droplet generators. Droplets can then be formed 604 from each sample/reagent mixture and the immiscible fluid in the droplet generators resulting in multiple droplet populations being generated. Each droplet population then flows from each respective droplet generator through separate channels, which can intersect at a downstream position. The droplet populations can be combined 605 inline, such as at the position of intersection of the separate channels, or offline, resulting in a droplet mixture. For example, the droplet populations can be collected from the droplet generators and then combined offline. The combined droplet mixture can then be mixed as the combined droplet mixture flows through a mixing module 607, such as a mixing channel, or can be collected and/or mixed off-line. Optionally, the combined droplet mixture can be split into one or more flow paths into multiple mixing channels 606 or split into one or more flow paths for collection in multiple vessels. After flowing through the one or more mixing channels, the mixed droplet mixture can then be collected 609, for example as the droplet mixture flows out of the one or more mixing channels. Optionally, after flowing through the one or more mixing channels, the mixed droplet mixture can be split 606 into one or more flow paths 608 as the droplet mixture flows out of the one or more mixing channels and the split droplet mixtures can be collected 609 in collection vessels. Energy can optionally be applied 610 to droplets at any point during the process to form a droplet skin (described herein) which can make the droplets more stable, more resistant to coalescence, more resistant to breakage, more resistant to shearing, more resistant to damage, or any combination thereof.

Droplets

One aspect of the invention is the ability to produce a large amount of droplets from a single population or two or more populations that are highly uniform. Such droplets have a variety of uses including, but not limited to: droplets for instrument qualification; droplets for field testing; bi-disperse, tri-disperse, and multi-disperse droplets; and droplets for biological applications.

The systems and methods disclosed here may be used to produce droplets that are suitable as performance standards or as calibration standards for droplet detection instruments. Using the systems and methods disclosed here, droplet samples may be produced in large quantities that are uniform, storable, stable and/or transportable. Large batches of such droplets may be aliquoted to produce many replicate samples. Droplets produced by the systems and methods disclosed here may be analyzed to determine their properties. The properties may be determined by analyzing the properties of one or more samples of the batch. Such properties may include the number of droplets, the fluorescence amplitude (mean, variance), droplet sizes (mean, variance), droplet quality (the number of damaged droplets, off-size droplets, etc.) as well as combinations of such properties, and the like. These qualities may be recorded on a certificate associated with the samples of the batch. The characterization may be done using known methods and those described herein.

The characterization may be done using a "gold standard" droplet detection instrument. Large uniform batches of droplets also enable characterizing droplets using a "gold standard" method. Performance of an instrument can be assessed by comparing its performance for a sub-batch of droplets to the performance of a "gold standard" using a sub-batch of droplets from the same parent batch. Performance differences can be attributed to the difference in instruments because the droplets come from the same parent batch.

Samples of the batch produced as described here may be stored for later use as is enabled by the stability of these droplets. Samples as described here may be used as performance standards. A sample of droplets may be analyzed using a test droplet detection instrument. The test droplet detection instrument may be the same as the "gold standard" droplet detection instrument or may be a different instrument. The droplet characteristics determined by the test droplet instrument may be compared to the droplet characteristics that were certified for the batch. A comparison of the certified and measured droplet properties may be used in the diagnosis of a problem with a test droplet detection instrument. A comparison of the certified and measured droplet properties may be used to verify the performance of a test instrument.

The droplets may be used to demonstrate the characteristics of a droplet based assay system. Preparation of assay samples for use in a droplet based assay system may require considerable care and expertise. In some cases it is desirable to mix droplets having different properties. To demonstrate the capabilities of a system, it may be preferable to simulate an assay rather than prepare actual assay samples. Droplets produced by the systems and methods described here may be used to simulate an assay. For example, a mixture of droplets with a high fluorescence and droplets with low fluorescence could be used to simulate an assay with a mixture of positive and negative droplets.

Droplets that are highly uniform can be used for instrument qualification and/or calibration, such as spectral or optical calibration, and can be subjected to downstream processing and analysis steps. For example, a batch of droplets can be used to qualify or calibrate a newly assembled or manufactured instrument to validate it conforms to specifications. Instrument qualification may require a large enough batch of droplets that the batch can be divided into two or more sub-batches. Each sub-batch can be used to qualify an instrument. For example, if an instrument is not functioning properly, a sub-batch of droplets can be used to characterize instrument performance before and after a repair action. Since the droplet sub-batches come from the same parent batch, performance differences before versus after the repair action can be attributed to the repair action versus an unintended change in droplet properties. Droplet mixtures can be subjected to a suitable reaction, such as thermal cycling to induce PCR amplification, so that target nucleic acids within the droplets, if any, are amplified to form additional copies. As another example, detection can be performed on droplet mixtures and can involve detecting signal(s) from the droplets indicative of whether or not there was amplification. Data analysis can be performed on droplet mixtures. For example, data analysis can involve estimating a concentration of the target nucleic acid or dye in the sample based on the percentage of droplets in which amplification occurred or intensity of fluorescent signal detected. Data analysis can also involve calibration and qualification of instruments using droplet mixtures with known concentrations of analytes or dyes, such as fluorescent molecules. To demonstrate the capabilities of a system, it may be preferable to simulate an assay rather than prepare actual assay samples. Droplets produced by the systems and methods described here may be used to simulate one or more assays, or multiple assays simultaneously. For example, a mixture of droplets with a high fluorescence and droplets with low fluorescence could be used to simulate an assay with a mixture of positive and negative droplets. For example, mixtures of droplets with a high fluorescence and droplets with low fluorescence in multiple channels could be used to simulate multiple assays simultaneously.

In some embodiments, droplets that are stable to coalescence, shearing, breakage, damage and/or other degradation mechanisms can be deployed for field testing.

Also provided herein are mixtures of two or more components. In some embodiments, each component is a substantially mono-disperse droplet population. The resulting mixtures can be substantially mono-disperse, such as when two nominally identical sub-populations are mixed together. In some embodiments, the two or more nominally identical sub-populations may differ slightly, such as due to an unintentional change in droplet size. In some embodiments, the components may be intentionally different, for example, a mixture of positive (high fluorescence) and negative (low fluorescence) droplets or mixtures of droplets with different sizes and/or shapes. In such embodiments, mixing is required to produce a uniform mixed batch of droplets. A uniform mixed batch of droplets is defined as a population such that, sub-batches drawn from the parent batch are substantially identical.

A droplet can be a small volume of liquid, typically with a spherical shape, encapsulated by an immiscible fluid, such as a continuous phase of an emulsion. The volume of a droplet, or the average volume of droplets in an emulsion, can, for example, be less than about one microliter, between about one microliter and one nanoliter, between about one microliter and one picoliter, less than about one nanoliter, between about one nanoliter and one picoliter, less than about one picoliter, or between about one picoliter and one femtoliter. A droplet, or droplets of an emulsion or droplet mixture, can have a diameter or an average diameter of less than about 1000, 100, or 10 micrometers, or of about 1000 to 10 micrometers. A droplet can be spherical or nonspherical. A droplet can be a simple droplet or a compound droplet (or multiple emulsion), that is, a droplet in which at least one droplet encapsulates or envelopes at least one other droplet.

A partition can be a separated portion of a bulk volume. The partition can be a sample partition generated from a sample, such as a prepared sample, that forms the bulk volume. Partitions generated from a bulk volume can be substantially uniform in size or can have distinct sizes (e.g., sets of partitions of two or more discrete, uniform sizes). Exemplary partitions are droplets. Partitions can also vary continuously in size with a predetermined size distribution or with a random size distribution.

The system can be utilized to generate droplets and droplet mixtures that can be used as calibration standards for perform a test, such as digital PCR (polymerase chain reaction) analysis. A test can be a procedure(s) and/or reaction(s) used to characterize a sample, and any signal(s), value(s), data, and/or result(s) obtained from the procedure(s) and/or reaction(s). A test also can be described as an assay. Exemplary droplet based assays are biochemical assays using aqueous assay mixtures. More particularly, the droplet-based assays can be enzyme assays and/or binding assays, among others. The enzyme assays can, for example, determine whether individual droplets contain a copy of a substrate molecule (e.g., a nucleic acid target) for an enzyme and/or a copy of an enzyme molecule. Based on these assay results, a concentration and/or copy number of the substrate and/or the enzyme in a sample can be estimated.

A reaction can be a chemical reaction, a binding interaction, a phenotypic change, or a combination thereof, which generally provides a detectable signal (e.g., a chemiluminescent signal, such as a fluorescent signal) indicating occurrence and/or an extent of occurrence of the reaction. In some cases, an exemplary reaction is an enzyme reaction that involves an enzyme-catalyzed conversion of a substrate to a product.

Any suitable enzyme reactions can be performed in the droplet-based assays disclosed herein. For example, the reactions can be catalyzed by a kinase, nuclease, nucleotide cyclase, nucleotide ligase, nucleotide phosphodiesterase, DNA polymerase (e.g., Taq polymerase), RNA polymerase, hot-start polymerase, prenyl transferase, pyrophospatase, reporter enzyme (e.g., alkaline phosphatase, beta-galactosidase, chloramphenicol acetyl transferse, glucuronidase, horse radish peroxidase, luciferase, etc.), reverse transcriptase, topoisomerase, etc.

Sample preparation can involve collecting a sample, such as a standard, calibration, clinical or environmental sample, treating the sample to release associated nucleic acids, and forming a reaction mixture involving the nucleic acids, such as for amplification of a target nucleic acid. In some embodiments, droplet generation can involve encapsulating fluorescent molecules, calibration standards, or the nucleic acids in droplets, for example, with about one copy of each target nucleic acid per droplet, where the droplets are suspended in an immiscible carrier fluid, such as oil, to form an emulsion.

An emulsion can be a composition comprising liquid droplets disposed in an immiscible carrier fluid, which also is liquid. The carrier fluid, also termed a background fluid, forms a continuous phase. The droplets (e.g., aqueous droplets) are formed by at least one droplet fluid, also termed a foreground fluid, which is a liquid and which forms a droplet phase (which can be termed a dispersed phase or discontinuous phase). The droplet phase is immiscible with the continuous phase, which means that the droplet phase and the continuous phase (carrier fluid) do not mix to attain homogeneity. The droplets are isolated from one another by the continuous phase and encapsulated, enclosed and/or surrounded by the continuous phase.

The aqueous phase can be substantially and/or predominantly water, but can incorporate a variety of additional components. The components can be soluble or miscible in water, such as one or more salts, buffering agents, reagents, samples of interest, analytes of interest, or whatever additional components can be necessary for a desired reaction that can be intended to occur within a formed droplet or capsule. All such additional components can be selected to be compatible with the desired reaction or intended assay. Additionally, the aqueous phase can include one or more skin-forming components. In some cases, the components can include droplets disposed in the aqueous phase, such as one more simple or compound droplets. For example, the aqueous phase can contain one or more oil droplets, which in turn can contain one or more aqueous droplets. Accordingly, the skin can encapsulate aqueous droplets that fuse with one another within the skin, during and/or after skin formation.

The droplets of an emulsion can have any uniform or non-uniform distribution in the continuous phase. If non-uniform, the concentration of the droplets can vary to provide one or more regions of higher droplet density and one or more regions of lower droplet density in the continuous phase. For example, droplets can sink or float in the continuous phase, can be clustered in one or more packets along a channel, can be focused toward the center or perimeter of a flow stream, or the like.

A packet can be a set of droplets or other isolated partitions disposed in the same continuous volume or volume region of a continuous phase. A packet thus can, for example, constitute all of the droplets of an emulsion or can constitute a segregated fraction of such droplets at a position along a channel. Typically, a packet refers to a collection of droplets that when analyzed in partial or total give a statistically relevant sampling to quantitatively make a prediction regarding a property of the entire starting sample from which the initial packet of droplets was made. The packet of droplets also indicates a spatial proximity between the first and the last droplets of the packet in a channel.

As an analogy with information technology, each droplet serves as a byte of information that can contain sequence specific information from a target analyte within a starting sample. A packet of droplets is then the sum of all these bytes of information that together provide statistically relevant information on the analyte of interest from the starting sample. As with a binary computer, a packet of droplets is analogous to the contiguous sequence of bits that comprises the smallest unit of binary data on which meaningful computations can be applied. A packet of droplets can be encoded temporally and/or spatially relative to other packets that are also disposed in a continuous phase (such as in a flow stream), and/or with the addition of other encoded information (optical, magnetic, etc.) that uniquely identifies the packet relative to other packets.

Any of the emulsions disclosed herein can be monodisperse, that is, composed of droplets of at least generally uniform size, or can be polydisperse, that is, composed of droplets of various sizes. If monodisperse, the droplets of the emulsion can, for example, vary in volume by a standard deviation that is less than about plus or minus 100%, 50%, 20%, 10%, 5%, 2%, or 1% of the average droplet volume. Droplets generated from an orifice can be monodisperse or polydisperse.

In some situations, a droplet flows through a fluid flow path as an emulsion, which may be characterized by having fluids or liquids in separate phases. For example, the phases may be an oil phase and an aqueous phase. In some cases, one or more of the phases may be a fluorous phase or may be any liquid compound or mixture of liquid compounds that is immiscible with water and that includes carbon, in some cases high carbon content. In some examples, oil also may have a high content of hydrogen, fluorine, silicon, oxygen, or any combination thereof, among others. For example, any of the emulsions disclosed herein may be water-in-oil (W/O) emulsion, e.g., aqueous droplets in a continuous oil phase. Conversely, any of the emulsions disclosed herein may be oil-in-water (O/W) emulsions. This disclosure also provides multiple emulsions. For example, aqueous droplets may be enveloped by a layer of oil and flow within an aqueous continuous phase. The oil may, for example, be or include at least one of hydrocarbon oil, silicone oil, mineral oil, fluorocarbon oil, vegetable oil, or a combination thereof, among others. Any other suitable components may be present in any of the emulsion phases, such as at least one surfactant, reagent, sample (e.g., partitions thereof), other additive, label, particles, or any combination thereof.

Often, emulsions become unstable when heated (e.g., to temperatures above 60° C.) when they are in a packed state (e.g., each droplet is near a neighboring droplet), because heat generally lowers interfacial tensions, which can lead to droplet coalescence. Thus, often packed emulsions do not maintain their integrity during high-temperature reactions, such as PCR, unless emulsion droplets are kept out of contact with one another or additives (e.g., other oil bases, surfactants, etc.) are used to modify the stability conditions (e.g., interfacial tension, viscosity, steric hindrance, etc.). For example, the droplets can be arranged in single file and spaced from one another along a channel to permit thermal cycling in order to perform PCR. However, following this approach using a standard emulsion does not permit a high density of droplets, thereby substantially limiting throughput in droplet-based assays.

Any emulsion disclosed herein can be a heat-stable emulsion. In some embodiments, a heat-stable emulsion is any emulsion that resists coalescence and/or breakage when heated to at least 50° C. A heat-stable emulsion can be a PCR-stable emulsion, which is an emulsion that resists coalescence and/or breakage throughout the thermal cycling of PCR (e.g., to permit performance of digital PCR). Accordingly, a PCR-stable emulsion can be resistant to coalescence and/or breakage when heated to at least 80° C., 90° C., or 96° C. for example, 81° C., 82° C., 83° C., 84° C., 85° C., 86° C., 87° C., 88° C., 89° C., 90° C., 91° C., 92° C., 93° C., 94° C., 95° C., 96° C., 97° C., 98° C., 99° C., or 100° C., among others. Due to heat stability, a PCR-stable emulsion, in contrast to a standard emulsion, enables PCR assays to be performed in droplets that remain substantially monodisperse throughout thermal cycling. Accordingly, digital PCR assays with PCR-stable emulsions can be substantially more quantitative than with standard emulsions. An emulsion can be formulated as PCR stable by, for example, proper selection of carrier fluid and surfactants, among others. An exemplary oil formulation to generate PCR-stable emulsions for flow-through assays is as follows: (1) Dow Corning 5225C Formulation Aid (10% active ingredient in decamethylcyclopentasiloxane) 20% w/w, 2% w/w final concentration active ingredient, (2) Dow Corning 749 Fluid (50% active ingredient in decamethylcyclopentasiloxane) 5% w/w, 2.5% w/w active ingredient, and (3) Poly(dimethylsiloxane) Dow Corning 200® fluid, viscosity 5.0 cSt (25° C.) 75% w/w. An exemplary oil formulation to generate PCR-stable emulsions for batch assays is as follows: (1) Dow Corning 5225C Formulation Aid (10% active ingredient in decamethylcyclopentasiloxane) 20% w/w, 2% w/w final concentration active ingredient, (2) Dow Corning 749 Fluid (50% active ingredient in decamethylcyclopentasiloxane) 60% w/w, 30% w/w active ingredient, and (3) Poly(dimethylsiloxane) Dow Corning 200® fluid, viscosity 5.0 cSt (25° C.) 20% w/w.

A surfactant can be a surface-active agent capable of reducing the surface tension of a liquid in which it is dissolved, and/or the interfacial tension with another phase. A surfactant, which also or alternatively can be described as a detergent and/or a wetting agent, incorporates both a hydrophilic portion and a hydrophobic portion, which collectively confer a dual hydrophilic-lipophilic character on the surfactant. A surfactant can be characterized according to a Hydrophile-Lipophile Balance (HLB) value, which is a measure of the surfactant's hydrophilicity compared to its lipophilicity. HLB values range from 0-60 and define the relative affinity of a surfactant for water and oil. Nonionic surfactants generally have HLB values ranging from 0-20 and ionic surfactants can have HLB values of up to 60. Hydrophilic surfactants have HLB values greater than about 10 and a greater affinity for water than oil. Lipophilic surfactants have HLB values less than about 10 and a greater affinity for oil than water. The emulsions disclosed herein and/or any phase thereof, can include at least one hydrophilic surfactant, at least one lipophilic surfactant, or a combination thereof. Alternatively, or in addition, the emulsions disclosed herein and/or any phase thereof, can include at least one nonionic (and/or ionic) detergent. Furthermore, an emulsion disclosed herein or any phase thereof can include a surfactant comprising, for example, polyethyleneglycol, polypropyleneglycol, or Tween 20.

In some embodiments, droplet generation can involve encapsulating dyes, such as fluorescent molecules, in droplets, for example, with a known concentration of dyes, where the droplets are suspended in an immiscible carrier fluid, such as oil, to form an emulsion. Exemplary fluorescent dyes that can used with the present system include a fluorescein derivative, such as carboxyfluorescein (FAM), and a PULSAR 650 dye (a derivative of Ru(bpy)3). FAM has a relatively small Stokes shift, while Pulsar® 650 dye has a very large Stokes shift. Both FAM and PULSAR 650 dye can be excited with light of approximately 460-480 nm. FAM emits light with a maximum of about 520 nm (and not substantially at 650 nm), while PULSAR 650 dye emits light with a maximum of about 650 nm (and not substantially at 520 nm). Carboxyfluorescein can be paired in a probe with, for example, BLACK HOLE Quencher™ 1 dye, and PULSAR 650 dye can be paired in a probe with, for example, BLACK HOLE Quencher™ 2 dye. For example, fluorescent dyes that can be used include, but are not limited to, DAPI, 5-FAM, 6-FAM, 5(6)-FAM, 5-ROX, 6-ROX, 5,6-ROX, 5-TAMRA, 6-TAMRA, 5(6)-TAMRA SYBR, TET, JOE, VIC, HEX, R6G, Cy3, NED, Cy3.5, Texas Red, Cy5, and Cy5.5.

Sample Preparation/Cartridge

This section describes exemplary system components for sample preparation, including cartridges for sample lysis and droplet generation.

It can be desirable to separate an enzymatic amplification system, such as a PCR-based DNA amplification system, into disposable and nondisposable components, for example, by creating a disposable cartridge or other disposable vessel for preparing and/or presenting samples to a nondisposable PCR instrument or other reader. Such a separation could facilitate rapid and low-cost DNA testing and analysis. The disposable cartridge may be designed as a single-use cartridge, to avoid the possibility of cross contamination between samples. Although the terms "cartridge" or "disposable cartridge" are used to reference the disposable portion of the DNA amplification system, the disposable portion generally may take various forms, and need not be rectangular or symmetric in any particular manner or dimension.

A suitable disposable cartridge can be configured to receive one or more samples and to prepare (or at least partially prepare) the one or more samples for analysis prior to PCR thermocycling and amplification. The cartridge may include an interface configured to pass the prepared samples to a nondisposable portion of a system for subsequent PCR amplification and analysis steps. In some cases, the interface between the cartridge and the system can be configured to transfer various fluids, such as oil and/or aqueous fluid, from the instrument to the cartridge, to "prime" or partially prime the cartridge for sample preparation. In other cases, the cartridge may be partially or entirely pre-primed with fluids, so that fluid transfer from the instrument is not necessary.

One or more disposable cartridges according to the present disclosure can be configured to generate one or more droplet populations or packets of droplet populations, each containing a mixture of sample and reagent, which then may be combined to form a droplet mixture, mixed and optionally collected in a collection vessel. The droplet mixture can then be transported from the collection vessel to an instrument, such as for rapid serial injection into a continuous flow thermal cycler or fluorescent detection instrument. The cartridge or other disposable vessel then may be removed from the system and discarded. The cartridge may be configured to prepare droplets relatively quickly, as measured by sample throughput and volume produced from the cartridge to the collection vessel. For example, a cartridge according to the present disclosure may be configured to perform sample preparation in a time of less than 5 minutes per sample, to achieve throughput of at least 10 samples per hour. The cartridge also may be constructed from and function in conjunction with non-hazardous materials, to minimize environmental impact.

The major functions that the disposable cartridge is configured to perform are purification, lysis, reagent mixing, and sample isolation into droplets. Alternatively, one or more steps, such as sample collection and extraction, can be performed prior to transferring target-containing material into the cartridge, while other steps are performed within the cartridge. Similarly, one or more steps, such as droplet generation, may be performed after transferring target-containing material out of the cartridge.

In one embodiment, droplet populations can be flowed from the cartridge to a downstream portion of the system. As noted above, the droplets can be contained within an emulsion, such as an oil-based emulsion, in which case transferring the droplets will include transferring portions or the entirety of the emulsion. When more than one sample/reagent mixture has been created, the droplet populations containing each type of mixture can be combined in a continuous or semi-continuous manner, so that a droplet mixture is formed. Continuous or semicontinuous droplet mixture formation can allow relatively rapid screening for multiple target DNA segments and creation of standards, such as a dye or a spectral standard, for high throughput instrument calibration.

Samples

A sample for use in the systems and methods described herein to produce droplets and droplet mixtures for testing or use as calibrations standards can be a compound, composition, and/or mixture of interest, from any suitable source(s). A sample is the general subject of interest for a test that analyzes an aspect of the sample, such as an aspect related to at least one analyte that can be present in the sample. Samples can be the same or different colors, such as one or more different fluorescent molecules at one or more concentrations. Samples can be analyzed in their natural state, as collected, and/or in an altered state, for example, following storage, preservation, extraction, lysis, dilution, concentration, purification, filtration, mixing with one or more reagents, pre-amplification (e.g., to achieve target enrichment by performing limited cycles (e.g., <15) of PCR on sample prior to PCR), removal of amplicon (e.g., treatment with uracil-d-glycosylase (UDG) prior to PCR to eliminate any carry-over contamination by a previously generated amplicon (i.e., the amplicon is digestable with UDG because it is generated with dUTP instead of dTTP)), partitioning, or any combination thereof, among others. Clinical samples can include nasopharyngeal wash, blood, plasma, cell-free plasma, buffy coat, saliva, urine, stool, sputum, mucous, wound swab, tissue biopsy, milk, a fluid aspirate, a swab (e.g., a nasopharyngeal swab), and/or tissue, among others. Environmental samples can include water, soil, aerosol, and/or air, among others. Research samples can include cultured cells, primary cells, bacteria, spores, viruses, small organisms, any of the clinical samples listed above, or the like. Additional samples can include foodstuffs, weapons components, biodefense samples to be tested for bio-threat agents, suspected contaminants, and so on.

Samples can be collected for diagnostic purposes (e.g., the quantitative measurement of a clinical analyte such as an infectious agent) or for monitoring purposes (e.g., to determine that an environmental analyte of interest such as a bio-threat agent has exceeded a predetermined threshold).

An analyte can be a component(s) or potential component (s) of a sample that is analyzed in a test. An analyte is a specific subject of interest in a test where the sample is the general subject of interest. An analyte can, for example, be a nucleic acid, protein, peptide, enzyme, cell, bacteria, spore, virus, organelle, macromolecular assembly, drug candidate, lipid, carbohydrate, metabolite, fluorescent molecule, or any combination thereof, among others. An analyte can be tested for its presence, activity, and/or other characteristic in a sample and/or in partitions thereof. The presence of an analyte can relate to an absolute or relative number, concentration, binary assessment (e.g., present or absent), or the like, of the analyte in a sample or in one or more partitions thereof. In some examples, a sample can be partitioned such that a copy of the analyte is not present in all of the partitions, such as being present in the partitions at an average concentration of about 0.0001 to 10,000, 0.001 to 1000, 0.01 to 100, 0.1 to 10, or one copy per partition. In some cases, the analyte is present, on average, at a concentration of less than 1, less than 2, less than 3, less than 4, less than 5, less than 6, less than 7, less than 8, less than 9, or less than 10 copies per partition (e.g., droplet).

A sample can be collected for analysis by a researcher, medical practitioner, a law enforcement agent, a scientist, or some other person with reason to collect a sample for nucleic acid analysis or to create a calibration standard. The sample can, for example, be collected using a sample collector, such as a swab, a sample card, a specimen drawing needle, a pipette, a syringe, and/or by any other suitable method. Furthermore, pre-collected samples can be stored in wells such as a single well or an array of wells in a plate, can be dried and/or frozen, can be put into an aerosol form, or can take the form of a culture or tissue sample prepared on a slide. Such pre-collected samples then can be obtained and prepared for droplet-based processing in a disposable cartridge. The collected sample can include one or more cells, bacteria, viruses, or other material potentially or actually containing a target sequence of nucleotides suitable for PCR amplification.

A collected sample can be extracted from a sample collector. This can be accomplished, for example, by transferring the sample from the sample collector using a pipette, a syringe, or the like, or by soaking and/or rinsing a sample collector in one or more suitable solutions, such as a digestive buffer solution, a lysis buffer solution, or an appropriate binder-containing solution, among others. Extraction can occur within a chamber of the disposable portion of the system, in which case the sample will be transferred to the cartridge prior to extraction. Alternatively, extraction can occur outside of the cartridge, and the resulting sample or sample-containing solution can then be transferred to the cartridge. In either case, the cartridge can be configured to perform various additional sample preparation steps, as described herein.

An extracted sample, which can be disposed in a sample chamber within a cartridge, can be purified and lysed. These steps can be performed at different times, simultaneously, or approximately simultaneously. Furthermore, purification can be performed either before or after lysing, and in some instances two or more separate purification steps can be performed, one before lysing and one after lysing. Purification can include some form of filtering to remove unwanted components from the sample while leaving the desired target components relatively unaffected, and lysing can include disruption of the sample constituents, such as by breaking the cellular membranes, to expose target DNA, and can involve some form of physical blending or stirring of the sample-containing mixture. For example, lysing can proceed through bulk mixing such as agitation, magnetic stirring, and/or aspiration, or through microfluidic mixing of various types such as forcing the sample through a tortuous path, electromagnetic bombardment, sonication, and/or convection. The fluid containing the contents of the lysed sample may be referred to as a lysate.

Depending on whether a particular purification step is performed before or after lysing, the method of purification may vary. For example, purification prior to lysing may be configured to capture relatively large target-containing material, such as bacteria or other cells. Purification at this stage can, for example, include filtering the sample-containing solution through an aperture-based filter with a characteristic aperture size smaller than the characteristic size of the target containing cells, to retain the cells or other target material within the sample chamber while removing other, smaller waste material. Purification after lysing can be configured to capture relatively small target material, such as DNA or partial nucleic acid sequences. Post-lysing purification can include filtration through a smaller filter, and/or affinity capture of DNA or other target material, to retain target material within the sample while removing other, larger waste material. In some cases, such as when purification steps are performed both before and after lysing, two or more different types of filters, including aperture-based filters and/or affinity-based filters, can be used.

A partially processed sample, such as a lysate, can be concentrated. This step can be accomplished by separating excess fluid in the lysate from the target DNA or DNA-containing material, for example, by filtering, ethanol precipitation, butanol extraction, or affinity capture, among others. The result of the concentration step can be a greater density of target material per unit volume of fluid. Concentration of the sample at this stage can result in a detectable amplified target after relatively fewer PCR amplification cycles than would be necessary without concentration.

A PCR reagent mixture can include appropriate enzymes and DNA primers and can be mixed with a sample. These reagent constituents are selected to facilitate DNA amplification of a particular target in conjunction with cyclical temperature changes (i.e., thermocycling). The reagent mixture can be combined with the sample in fluid form, or it can be lyophilized (freeze-dried) and converted into a powder, a pellet, or any other convenient form. To form a lyophilized reagent, suitable stabilizing and/or sedimenting agents can be combined with the PCR enzymes and DNA primers.

One or more reagents can be mixed with the sample to form either a single sample/reagent mixture containing multiple reagents, or multiple mixtures each containing a single reagent. A single mixture containing multiple reagents can, for example, allow screening for multiple targets simultaneously or calibration of multiple components of an instrument, whereas multiple mixtures each containing a single reagent can be configured for PCR amplification of several different DNA targets, or (when two or more of the mixtures contain the same reagent) to provide experimental control, for instance, by allowing multiple PCR amplification and/or detection techniques to be applied to the same sample/reagent mixture. When multiple sample/reagent mixtures are used, the different mixtures can be separately prepared and/or separately tracked through the system.

Two more populations of droplets containing the samples and the reagents can be generated, typically in aqueous form within an oil-based emulsion. The generated droplet populations can contain a mixture of sample and reagent, either activated or not activated (i.e., either requiring or not requiring an additional activation step before PCR amplification begins), or the droplet populations can each contain sample and reagent that can be separated from each other, for example, by a thin membrane, such as an oil membrane. Common modes of droplet generation include flow focusing, jetting, and shearing. Using these techniques, stable droplet populations can be created at throughputs of 10-1000 Hz with tunable volumes ranging from 15 picoliters (pL) to 5 nanoliters (nL).

Alternatively, or in addition, droplets containing various sample/reagent mixtures can be "tagged" in some manner, such as with a bar code or some other detectable component, in which case different types of droplets can in some instances be transferred to the downstream portion of the system to form a mixture, mixed, collected and then detected individually.

Droplet Generators

Any droplet generator known in the art can be used with the current invention. Other types of droplet generators that can be used in the system described herein include, but are not limited to, thermal bubble, thermal buckling, electrostatic, inertial actuated, acoustic wave, monodisperse, polydisperse, micro fluidic, piezoelectric, flow-focus droplet generators, and those described in U.S. application Ser. Nos. 12/586,626, 12/962,511, 12/963,523, 12/962,502, 13/039, 233, 129/62,507, 12/862,542, 13/072,673. Droplets can be generated as described in U.S. application Ser. Nos. 12/976, 827 and 12/976,816.

The accuracy and reproducibility of droplet-based assays can rely on droplets having a uniform, stable size as described in U.S. application Ser. No. 12/976,816. (U.S. Pub. No. 2011/0217711, Hiddessen et. al.). However, maintaining the integrity of droplets can present a challenge. Manipulation and processing of droplets can cause the droplets to break, coalesce, or both, which can change an emulsion with a uniform size of droplets (a monodisperse emulsion) to one with a wide range of droplets (a polydisperse emulsion). For example, emulsions can become unstable as the packing density of droplets is increased, because droplet proximity enables coalescence. This instability can limit the ability to store droplets for extended periods of time, such as when shipping droplets to consumers. Also, the tendency of droplets to coalesce at a high packing density can restrict the options for batch processing of droplets in a bulk phase.

The tendency of droplets both to coalesce and break can be exacerbated by higher temperatures and particularly the repetitive cycles of heating and cooling that are utilized for PCR amplification of a nucleic acid target in droplets. In addition, fluidic and mechanical manipulation can damage droplets. Droplets can be undesirably induced to coalesce by an electric field ("electro-coalescence"), which can be created by a static charge on a surface. Accordingly, droplets may be undesirably induced to coalesce during fluidic or mechanical manipulation, such as in a flow channel, or during aspiration into or dispensing from a pipet tip, or vigorous mixing, among others. Furthermore, emulsion droplets can be susceptible to breakage when subjected to shear forces, such as when flowing in a channel and/or when there is a sudden change in direction of flow. For quantitative assays, droplet aggregation, coalescence, and breakage can all introduce large errors to make the assays inaccurate and unreliable.

Droplet generators also have limited throughput. Thus, it is an object of the current invention to increase throughput by combining droplets, droplet populations, or droplet streams produced from two or more droplet generators into one or more combined droplet mixtures.

In practice, each droplet generator can have one or more slightly different physical dimensions. As a result, droplet generators may make droplets that differ in one or more characteristics, such as droplet size, diameter, shape, integrity, turbidity, concentration of analytes, particle size distribution, electrical charge, interfacial properties, composition, thickness, rheology, charge, attractive and repulsive interactions, physical state, viscosity, and others. Droplet generators may make droplet populations or streams that differ in one or more characteristics such as homogeneity, dispersity, droplet concentration, distribution, level of aggregation. Thus, if the droplets from two or more droplet generators are combined without mixing, the combined droplet mixture may not be uniform (samples drawn from the combined droplet mixture may differ from each other). Thus, it is an object of the current invention to provide substantially homogeneously mixed, and/or substantially uniform droplet mixtures by mixing two or more populations or streams of droplets produced from two or more different generators. The invention provides a means to mix the two or more sub-populations of droplets to provide a uniform sample.

Combined droplet mixtures of two or more populations of droplets should be thoroughly mixed in order for the droplets of the populations to be dispersed within the droplet mixture uniformly. However, mixing may cause undesired droplet coalescence, shearing, and/or droplet damage. For example, standard mixing techniques such as stirring, vortexing, triturating, etc., may damage the droplets. Thus, it is an object of the current invention to provide uniform droplet mixtures without substantial undesired properties, such as aggregation, coalescence, shearing, and/or damage.

In some embodiments, the two or more droplet generators of the system disclosed herein can each comprise a droplet outlet portion which can include an emulsion outlet channel and upper and lower channel walls defining an oil channel and a sample-containing portion configured to be selectively assembled with the droplet outlet portion and including a sample reservoir and a fluid outlet aperture configured to emit droplets of sample-containing fluid from the sample reservoir. In some embodiments, a system can comprise more than two droplet generators, each comprising one or more channels. For example, a system can comprise 3, 4, 5, 6, 7, 8, 9, 10, or more droplet generators, each with one or more droplet channels. In some embodiments, the one or more channels of the two or more droplet generators intersect with each other.

When the droplet outlet portion and the sample-containing portion of each droplet generator are assembled together, a substantially fluid-tight seal can be formed between the droplet outlet portion and the sample-containing portion. Sample emitted by the fluid outlet apertures of each droplet generator can intersect oil traveling in the oil channel to produce emulsions of water-in-oil droplets. Each of the emulsions can pass into an emulsion outlet channel of each droplet generator. The emulsion outlet channels can intersect at a downstream region and the emulsions can be combined to form a droplet mixture at the intersection of the emulsion outlet channels.

In some embodiments, the system can include fluid reservoirs configured to hold background emulsion fluids having a first density and a foreground emulsion fluids having a second density. The system can further include two or more droplet generators each including elongate tips configured to be at least partially inserted into the fluid reservoirs and having at least one side aperture and a distal aperture. The distal aperture can be configured to be in contact with background fluids held by the reservoirs and the side aperture can be configured to be in contact with foreground fluids held by the reservoirs when the reservoirs contain background and foreground fluids and the elongate tips are inserted into the reservoir. The droplet generators can be configured such that foreground fluids flowing into the side apertures intersects with streams of background fluids that enters the tips through the distal apertures, to form emulsions of foreground fluid droplets in background fluids.

In some embodiments, the droplet mixture generating systems described herein can include two or more emulsion generators, which can include inner fluid chambers configured to contain sample-containing fluids and have distal apertures configured to allow passage of the sample containing fluids out of the inner fluid chambers and outer fluid chambers configured to contain background fluids. The outer fluid chambers can surround at least portions of the inner fluid chambers and can have distal apertures configured to allow passage of the emulsions out of the outer fluid chambers. Background fluid channels can be formed between external boundaries of the inner fluid chambers and internal boundaries of the outer fluid chambers, and configured to transfer background fluids radially inward toward the distal apertures of the outer fluid chambers. The inner and outer fluid chambers can be positioned so that oil flowing radially inward through the background fluid channels can intersect with sample-containing fluids passing out of the inner fluid chambers through the distal apertures of the inner fluid chambers, to generate emulsions of sample-containing droplets within the background fluids which can pass through the distal apertures of the outer fluid chambers. The droplet mixture generating systems described herein can include emulsion outlets downstream, and in fluid connection with the emulsion generators, and configured to receive the emulsions generated by each of the emulsion generators.

One non-limiting example of a type of droplet generator that can be used to create droplets using the system described herein can be any cross-type droplet generator. The term "cross-type droplet generator" indicates that a background emulsion fluid (typically oil) travels inward from two substantially opposite directions to intersect a foreground emulsion fluid (typically an aqueous fluid) traveling at right angles to the direction of travel of the background fluid, to form an emulsion that moves along the original direction of travel of the foreground fluid. Thus, the directions of travel of the incoming background fluid, the incoming foreground fluid, and the outgoing emulsion form a cross. Accordingly, droplet generators can include two complementary sections of hollow fluidic tubing separated by a small distance.

Tubing sections can be constructed from a single continuous hollow tube that has been cut and separated, in which case the tubing sections will have substantially equal outer and inner diameters. Alternatively, tubing sections can be constructed separately and then disposed appropriately within the droplet generator, in which case the tubing sections can have substantially different outer and/or inner diameters. Tubing sections can be disposed at least partially within an oil channel. An oil channel can be a portion of a fluid reservoir configured to supply fluids, including oil and/or sample-containing aqueous fluid, to each droplet generator. An oil channel can take various forms, such as a cylindrical channel formed within a tube, a rectangular channel formed between substantially planar channel walls, or simply a fluid flow path within a surrounding reservoir of fluid, among others. Tubing sections can be formed integrally with an oil channel, or the tubing sections can be inserted into one or more apertures of the oil channel in a substantially fluid tight manner.

Tubing sections can includes a hollow inner portion forming an incoming fluid channel, and tubing sections can includes a hollow inner portion forming an outgoing fluid channel. Incoming fluid channels can be configured to transport sample-containing fluid from a fluid source such as a surrounding fluid reservoir or a reagent chamber into oil channel, and can be pressurized relative to the oil channel to facilitate that transfer. To generate sample containing droplet populations, oil in an oil channel and sample-containing fluid in an incoming fluid channel each can be pressurized relative to an outgoing fluid channel, tending to draw both oil and sample-containing fluid toward an inlet aperture of the outgoing fluid channel As the sample containing fluid exits an outlet aperture of an incoming fluid channel, aqueous droplets of sample-containing fluid can be formed in an oil background, resulting in a water-in-oil emulsion of droplets entering the outgoing fluid channel.

One of tubing sections can be fixed within a surrounding fluid reservoir, whereas the other tubing section can be removable from the surrounding reservoir. In such cases, one tubing section can be fixed in place, whereas another tubing section can be removable, and can be configured to be selectively placed into position at a known, desired distance from the one tubing section. For example, a tubing section can represent the tip of a syringe, pipette, or the like, which can be inserted into a reservoir containing an oil channel and used to create and store sample-containing droplets by applying suction to draw an emulsion of sample-containing droplets into an inlet aperture of an outgoing fluid channel In some embodiments, a droplet generator can be constructed from a single section of fluidic tubing, through which two perpendicular and intersecting fluid channels can be formed. A droplet generator can be temporarily or permanently disposed within a fluid reservoir configured to hold fluids used to form an emulsion of sample-containing droplets, such as a background oil and a foreground sample-containing aqueous solution. A distal aperture of a fluid channel can be configured to receive and transport the sample-containing solution, and intermediate apertures of a fluid channel can be configured to receive and transport the background oil.

At an intersection region of a droplet generator, a sample-containing fluid traveling through a channel can intersect with oil traveling through a channel, and a water-in-oil emulsion of sample-containing droplets can be generated. This emulsion generated from one droplet generator then continues to travel through a channel along the original direction of travel of the sample containing fluid and can intersect with another channel through which another emulsion generated from a second droplet generator continues to travel through another downstream channel.

Droplet Mixture Generation

Using the systems described herein, droplet mixtures with known concentrations of reagents and samples, such as fluorescent calibration standards, contained within the droplets can be produced by mixing positive (high fluorescence amplitude) and negative (low fluorescence amplitude) drops or droplet populations in a uniform manner over time and can be used to simulate concentrations that would be measured. Droplet mixtures can contain droplet populations that can contain different or similar concentrations of dyes, can be used for different or similar assays, and can be of different or similar sizes.

Droplets can be generated from a sample. In some embodiments, droplets can be generated from a solution comprising calibration standards, such as fluorescent dyes at a known concentration, for example negative, low, medium, positive, or high concentrations. In some embodiments, droplet generation can be performed after the sample has been modified by mixing it with one or more reagents to form a bulk assay mixture. Droplet generation can divide the bulk assay mixture into a plurality of partitioned assay mixtures, such as sample partitions, that are isolated from one another in respective droplets by an intervening, immiscible carrier fluid. Droplets may be generated from a sample serially, such as from one orifice or a droplet generator (i.e., emulsion generator). Alternatively, droplets may be generated in parallel from a sample, such as from two or more orifices, two or more droplet generators in fluid communication with, or supplied by, the same sample, or a combination thereof. As another example, droplets may be generated in parallel from a perforated plate defining an array of orifices. In some embodiments, droplets may be generated in bulk, such as by agitation or sonication, among others. In some examples, a plurality of emulsions may be generated, either serially or in parallel, from a plurality of samples.

A droplet mixture can be generated from two or more droplet populations generated from one or more samples, such as from one sample with high simulated concentration of reagents and/or one sample with a low simulated concentration of reagents. For example, a droplet mixture can be generated from 2, 3, 4, 5, 6, 7, 8, 9, 10, or more droplet populations generated from one or more samples. For example, a droplet mixture can be generated from 2, 3, 4, 5, 6, 7, 8, 9, 10, or more droplet populations generated from 1, 2, 3, 4, 5, 6, 7, 8, 9, 10, or more samples. A droplet mixture can be generated from two or more droplet populations generated from one or more samples which have been modified by mixing two or more droplet populations with reagents to form bulk assay mixtures each comprising a droplet population generated from a different droplet generator. Droplet mixture generation can comprise combining two or more droplet populations, each comprising a partitioned assay mixture that are isolated from one another in respective droplets by an intervening, immiscible carrier fluid. Droplet mixtures, can be generated from two or more droplet populations serially, such as from one orifice and/or one droplet generator. In some embodiments, droplet mixtures can be generated in parallel from two or more droplet populations, such as from two or more orifices and/or two or more droplet generators in fluid communication with or supplied by two or more samples or droplet populations. As another example, droplet mixtures can be generated in parallel from a perforated plate defining an array of orifices. In some examples, the droplet mixtures can be generated in bulk, such as by rocking, agitation or sonication, among others. In some examples, a plurality of emulsions may be generated, either serially or in parallel, from a plurality of samples.

In one embodiment, a single aqueous composition feeds 2 or more droplet generators run in parallel two produce two populations of droplets. These populations are mixed to provide a parent batch. In one embodiment, two or more aqueous compositions feed 2 or more droplet generators run in parallel two produce two sub-populations of droplets. These populations can be combined and mixed to provide a parent batch.

The parent batch may be optionally collected in one or more collection modules. The embodiment may optionally include a stabilization module, such as an energy transfer module or heating module.

A droplet mixture can be generated by partitioning a sample with a first droplet generator to produce a first droplet stream; partitioning a sample with a second droplet generator to produce a second droplet stream; and combining the first droplet stream and the second droplet stream to produce a combined droplet stream. In some embodiments, a combined droplet stream can be substantially uniform or homogenous. In some embodiments, a combined droplet stream can be substantially non-uniform or heterogeneous. Partitioning two or more samples with two or more droplet generators can occur at the same or different locations. For example, partitioning a sample with a first droplet generator can occur at one location, and partitioning a sample with a second droplet generator can occur at the same or a different location located any number of kilometers away. For example, partitioning a sample with a first droplet generator can occur at one location, and partitioning a sample with a second droplet generator can occur at a different location located 0.5, 1, 2, 3, 4, 5, 6, 7, 8, 9, 10, 20, 30, 40, 50, 60, 70, 80, 90, 100, 110, 120, 130, 140, 150, 160, 170, 200, 300, 400, 500, 600, 700, 800, 900, 1000, 2000, 3000, 4000, 5000, or more kilometers away.

Partitioning two or more samples with two or more droplet generators can occur at the same or different time. For example, partitioning a sample with a first droplet generator can occur at one time, and partitioning a sample with a second droplet generator can occur at the same or a different time. For example, partitioning a sample with a first droplet generator can occur at one time, and partitioning a sample with a second droplet generator can occur 1, 5, 10, 20, 30, 40, 50, or 60 minutes, or 2, 3, 4, 5, 6, 7, 8, 9, 10, 11, 12, 13, 14, 15, 16, 17, 18, 19, 20, 21, 22, 23, or 24 hours or 2, 3, 4, 5, 6, 7, 8, 9, 10, or more days, or 1, 2, 3, 4, 5, 6, 7, 8, 9, 10, 11, 12 or more months before or after partitioning the sample with the first droplet generator.

A portion of a combined droplet stream or droplet mixture can be extracted and a signal can be detected. Detection of a signal from a combined droplet stream or droplet mixture can be performed at least about 1, 5, 10, 20, 30, 40, 50, or 60 minutes, or 2, 3, 4, 5, 6, 7, 8, 9, 10, 11, 12, 13, 14, 15, 16, 17, 18, 19, 20, 21, 22, 23, or 24 hours or 2, 3, 4, 5, 6, 7, 8, 9, 10, or more days, or 1, 2, 3, 4, 5, 6, 7, 8, 9, 10, 11, 12 or more months after one of the steps of partitioning a sample from a first or second droplet generator. Detection of a signal from a combined droplet stream or droplet mixture can be performed at a location that is at least about 0.5, 1, 2, 3, 4, 5, 6, 7, 8, 9, 10, 20, 30, 40, 50, 60, 70, 80, 90, 100, 110, 120, 130, 140, 150, 160, 170, 200, 300, 400, 500, 600, 700, 800, 900, 1000, 2000, 3000, 4000, 5000, or more kilometers away from the location of generation of a first droplet stream, second droplet stream, or both.

The signal detected from a droplet mixture, or partition thereof, produced by any of the methods described herein, can degrade less than about 1%, 2%, 3%, 4%, 5%, 10%, 20%, 30%, 40%, or 50%, after transport, storage, or manipulation. For example, the signal detected from a droplet mixture, or partition thereof, produced by any of the methods described herein, can degrade less than about 1%, 2%, 3%, 4%, 5%, 10%, 20%, 30%, 40%, or 50%, after transport of a first and/or second droplet population or stream, or droplet mixture thereof, over a distance of 0.5, 1, 2, 3, 4, 5, 6, 7, 8, 9, 10, 20, 30, 40, 50, 60, 70, 80, 90, 100, 110, 120, 130, 140, 150, 160, 170, 200, 300, 400, 500, 600, 700, 800, 900, 1000, 2000, 3000, 4000, 5000, or more kilometers. For example, the signal detected from a droplet mixture, or partition thereof, produced by any of the methods described herein, can degrade less than about 1%, 2%, 3%, 4%, 5%, 10%, 20%, 30%, 40%, or 50%, after storage of a first and/or second droplet population or stream, or droplet mixture thereof, for 1, 2, 3, 4, 5, 6, 7, 8, 9, 10, 11, 12, 13, 14, 15, 16, 17, 18, 19, 20, 21, 22, 23, or 24 hours or 2, 3, 4, 5, 6, 7, 8, 9, 10, or more days, or 1, 2, 3, 4, 5, 6, 7, 8, 9, 10, 11, 12 or more months.

Pumps

The flow of each sample used for generation of a population of droplets using a droplet generator and/or the flow of droplets through a microfluidic network of any of the systems described herein and/or the flow of each droplet population and/or combined droplet mixture can be individually or separately controlled by one or more pressure sources, such as pumps, through a droplet generator or channel, such as a mixing channel. A pressure source can provide positive or negative pressure. In this manner, the size and/or other characteristics of the droplets generated can be varied and can result in mono-disperse or polydisperse emulsions. For example, one or more pumps can be used to flow a sample mixture comprising a positive or high concentration of fluorescent molecules through one droplet generator of the system, and one or more other pumps can be used to flow a sample mixture comprising a negative or low concentration of fluorescent molecules thorough another droplet generator of the system. The use of separate or distinct pumps to control the flow of each sample through the system can allow for creating droplets containing a partition of one sample at a different rate than the rate of the droplets formed from another sample controlled by another pump. In this manner, the concentration of droplets of one population of droplets can be lower, higher, or the same with respect to the concentration of droplets of another population of droplets in a droplet mixture.

Pumps can be peristaltic pumps, positive or negative pressure-driven pumps, conducting polymer pumps, electro-osmotic pumps, bubble pumps, piezo-electric driven pumps, or another type of pump suitable for pumping fluids through microfluidic chips. In some embodiments a pump can be a vacuum pump, such as a syringe pump. A pump may supply a positive pressure or a negative pressure. A pressure source, such as a pressurized gas, may be substituted for one or more of the pumps. Gravitational, centrifugal or other forces may also be used to provide fluid flow. In one embodiment pressure, such as positive or negative vacuum pressure can be used to flow samples, drops, droplet populations, and/or droplet mixtures through the system. In this manner, pressure can be used to push or pull samples, drops, droplet populations, and/or droplet mixtures through the system. Pressure can be created through the use of pumps, such as syringe pumps, and tubing or a mechanical tube guide. Pressure driven flow can be used for mixing droplets within the system, such as within a mixing channel. Pressure driven flow can be used to control the flow rate of liquids and droplets through the system, such as to increase or reduce the time of thermal exposure to a heating member. One advantage of a positive pressure system is that droplets can be immediately available for use from the collection reservoir, which is at ambient pressure and open to atmosphere. Thus, the drops can be used in real time as soon as they emerge from a mixing channel (described below).

A pump of any of the systems or methods described herein can be operable to flow the droplets through a channel, such as mixing channel of a mixing module at a flow rate from 1

µl/minute to 10000 µl/minute for example, a pump can be operable to flow the droplets at a flow rate from 1 µl/minute to 10000 µl/minute, 1 µl/minute to 5000 µl/minute, 1 µl/minute to 3000 µl/minute, 1 µl/minute to 1000 µl/minute, 1 µl/minute to 500 µl/minute, 1 µl/minute to 300 µl/minute, 1 µl/minute to 100 µl/minute, 1 µl/minute to 50 µl/minute, 1 µl/minute to 25 µl/minute, 1 µl/minute to 10 µl/minute, 1 µl/minute to 5 µl/minute, 5 µl/minute to 10000 µl/minute, 5 µl/minute to 5000 µl/minute, 5 µl/minute to 3000 µl/minute, 5 µl/minute to 1000 µl/minute, 5 µl/minute to 500 µl/minute, 5 µl/minute to 300 µl/minute, 5 µl/minute to 100 µl/minute, 5 µl/minute to 50 µl/minute, 5 µl/minute to 25 µl/minute, 5 µl/minute to 10 µl/minute, 10 µl/minute to 10000 µl/minute, 10 µl/minute to 5000 µl/minute, 10 µl/minute to 3000 µl/minute, 10 µl/minute to 1000 µl/minute, 10 µl/minute to 500 µl/minute, 10 µl/minute to 300 µl/minute, 10 µl/minute to 100 µl/minute, 10 µl/minute to 50 µl/minute, 10 µl/minute to 25 µl/minute, 25 µl/minute to 10000 µl/minute, 25 µl/minute to 5000 µl/minute, 25 µl/minute to 3000 µl/minute, 25 µl/minute to 1000 µl/minute, 25 µl/minute to 500 µl/minute, 25 µl/minute to 300 µl/minute, 25 µl/minute to 100 µl/minute, 25 µl/minute to 50 µl/minute, 50 µl/minute to 10000 µl/minute, 50 µl/minute to 5000 µl/minute, 50 µl/minute to 3000 µl/minute, 50 µl/minute to 1000 µl/minute, 50 µl/minute to 500 µl/minute, 50 µl/minute to 300 µl/minute, 50 µl/minute to 100 µl/minute, 100 µl/minute to 10000 µl/minute, 100 µl/minute to 5000 µl/minute, 100 µl/minute to 3000 µl/minute, 100 µl/minute to 1000 µl/minute, 100 µl/minute to 500 µl/minute, 100 µl/minute to 300 µl/minute, 300 µl/minute to 10000 µl/minute, 300 µl/minute to 5000 µl/minute, 300 µl/minute to 3000 µl/minute, 300 µl/minute to 1000 µl/minute, 300 µl/minute to 500 µl/minute, 500 µl/minute to 10000 µl/minute, 500 µl/minute to 5000 µl/minute, 500 µl/minute to 3000 µl/minute, 500 µl/minute to 1000 µl/minute, 1000 µl/minute to 10000 µl/minute, 1000 µl/minute to 5000 µl/minute, 1000 µl/minute to 3000 µl/minute, 3000 µl/minute to 10000 µl/minute, 3000 µl/minute to 5000 µl/minute, or 5000 µl/minute to 10000 µl/minute. In some embodiments, the flow rate is equal to [(droplets/time (minutes))*(average droplet volume (µl))].

The rate of droplet formation of one population of droplets can be lower, higher, or the same with respect to the rate of droplet formation of another population of droplets. For example, a pump can be used generate a flow rate for a first sample or first population of droplets that is 2, 3, 4, 5, 6, 7, 8, 9, 10, 11, 12, 13, 14, 15, 16, 17, 18, 19, 20 or more times the flow rate generated for a second sample or second population of droplets. As a non-limiting example, a pump used to control the flow of a first sample or first population of droplets that is set to flow at twice the flow rate of a second sample or second population of droplets can result in a droplet mixture comprising about twice as many droplets from the first population than the number or concentration of droplets of the second population of droplets. Thus, a mixture of droplets produced using any of the systems described herein can result in a droplet mixture comprising two or more droplet populations at any ratio. For example, the ratio of a first population of droplets to a second population of droplets can be 2:1, 3:1, 4:1, 5:1, 6:1, 7:1, 8:1, 9:1, 10:1, 11:1, 12:1, 13:1, 14:1, 15:1, 16:1, 17:1, 18:1, 19:1, or 20:1, or higher.

In some embodiments, the same pump can be used to flow the samples or droplets through the two or more droplet generators or a microfluidic network. One or more pumps can also be used to flow the immiscible solution through the two or more droplet generators. One pump can be used to flow the immiscible solution through one droplet generator at one flow rate, and another pump can be used to flow the immiscible solution through another droplet generator at another flow rate. In some embodiments, the same pump can be used to flow the immiscible solution through the two or more droplet generators. In some embodiments, electrowetting is not used to flow the droplets.

Mixing Module

Droplets and/or droplet populations can be very difficult to precisely mix by pipetting, and a combined droplet mixture of two or more droplet populations can be difficult to mix without shearing or coalescing droplets undesirably. It is an object of the current system to provide an accurate and precise solution to the difficulty in generating accurate, reproducible, and precise simulated concentrations of reagents within droplets, concentrations of droplet populations within a droplet mixture, and to produce homogenous mixtures and/or substantially uniform droplet mixtures without undesired coalescence, shearing, damage, and/or breakage of the droplets in the mixture.

In some embodiments, a mixing module can be a vessel suitable for containing droplets. For example, a mixing module can be used for off-line mixing of droplets. Mixing can be accomplished by moving, shaking, rotating, or vibrating a mixing module. In some embodiments, mixing can be accomplished by moving, rotating, shaking, or vibrating a mixing module containing droplets by an automated method.

In some embodiments, a mixing module of the systems and methods described herein can comprise a mixing channel. The mixing channel of the systems described herein can be useful for mixing multiple droplet populations, which can be combined with tubing unions shortly after emerging from the chip and optionally before stabilizing the droplets by applying energy, such as heat. Mixing multiple droplet populations not only increases throughput, but can also allow for thoroughly mixed samples with various "positive" and "negative" populations for simulating concentrations of DNA or for checking color calibration and/or compensation. As the droplets emerge from a mixing channel, which can optionally be heated, they can be collected in one or more collection vessels for subsequent storage and/or use.

A mixing channel can be of various shapes to allow for mixing of multiple droplet populations after the droplet populations produced from two or more droplet generators are combined. The mixing channel can be of various geometric configurations that afford mixing of droplet populations. For example, a mixing channel of the system can be linear or non-linear. A non-linear mixing channel can a turn or can have a serpentine, zig-zag, loop, roll, spiral, basketweave, braided, partial circle, figure eight knot, or loosely knotted geometry or shape.

A serpentine mixing channel can refer to a channel that has a total length that is greater than the linear distance between the end points of the channel. A serpentine channel may be oriented entirely vertically or horizontally. Alternatively, portions of a serpentine channel can be oriented vertically and portions can be oriented horizontally.

Any of the systems described herein can include one or more mixing channels. For example, the system can include 1, 2, 3, 4, 5, 6, 7, 8, 9, 10, 11, 12, 13, 14, 15, 16, 17, 18, 19, or 20 or more mixing channels. In some embodiments, one or more of the mixing channels can share a stabilization module, such as a heating element. In some embodiments, one or more of the mixing channels can have independent stabilization modules.

The one or more mixing channels can be arranged in any orientation relative to each other, such as side-by-side, or stacked mixing channels. The mixing channels can include one or more tube exit points as shown in FIG. 3. For example, the mixing channels can include 1, 2, 3, 4, 5, 6, 7, 8, 9, 10, 11, 12, 13, 14, 15, 16, 17, 18, 19, or 20 or more tube exit points. Multiple exit points can allow for shorter or longer exposure to a stabilization module, such as for applying energy for temperature control of droplets.

A mixing channel, such as a serpentine mixing channel, can have any number of turns. For example, a mixing channel can have 1, 2, 3, 4, 5, 6, 7, 8, 9, 10, 11, 12, 13, 14, 15, 16, 17, 18, 19, or 20 or more turns. As used herein, a turn or a corner, when referring to channel geometry, can refer to a channel having a flow direction change of at least about 15°. In some embodiments a turn can include an abrupt channel flow direction change. In some embodiments, a turn can be a curved or arced channel turn. In some embodiments, turns or corners can be at least about 45°. In some embodiments, turns or corners can be greater than 90°. In some embodiments, turns or corners can be greater than about 150°. For example, a turn or corner in a channel can be at least about 20°, 25°, 30°, 35°, 40°, 45°, 50°, 55°, 60°, 65°, 70°, 75°, 80°, 85°, 90°, 95°, 100°, 105°, 110°, 115°, 120°, 125°, 130°, 135°, 140°, 145°, or 150°. In some embodiments, a mixing channel can be a channel with 1, 2, 3, 4, 5, 6, 7, 8, 9, 10, 11, 12, 13, 14, 15, 16, 17, 18, 19, or 20 or more turns that are as large as 180°.

Liquid flow in microfluidic channels typically occurs at low Reynolds numbers, such that the flow is purely laminar. As a consequence, two or more streams of miscible fluids flowing side-by-side only mix by diffusion and such mixing can be slow. It is an object of the present invention to mix droplets in a combined droplet population by flowing the droplet mixture through the flow channel such that one droplet passes another droplet, such as in the direction of the flow or an angle other than the direction of the flow. The flow through the mixing channel can be laminar or turbulent or a combination thereof.

Any mixing channel described herein can have a diameter and or geometry that allows for a first droplet in a droplet mixture to pass a second droplet in the droplet mixture, thereby promoting mixing of the droplet in the droplet mixture. For example, the diameter of the mixing channel can allow for the mixing of droplets along the direction of the flow, an angle perpendicular to the flow direction, or an angle not in the direction of flow, as opposed to flowing two or more droplets sequentially through a mixing channel. For example, if droplet B is flowing behind droplet A, the mixing channel may permit droplet B to pass droplet A within the channel. The mixing channel may also permit mixing along the axis perpendicular to the flow of the droplets. For example, at one point in time, an axis perpendicular to the flow of droplets may contain droplets A and B; and then, after mixing, A and B may no longer occupy the same axis perpendicular to the flow of droplets. In some cases, droplets A and B occupy the same axis perpendicular to the flow of droplets; but after mixing of the droplets, droplet A and droplet C (rather than droplet B) occupy the same axis perpendicular to the flow of droplets. Droplets within the mixing channel can be succumbed to laminar flow or turbulent flow, such as flow that creates turbulent eddies to mix droplets.

A mixing channel that can allow for a first droplet in a droplet mixture to pass a second droplet in the droplet mixture to promote mixing of droplets as they are flowed through the channel can be described as having a larger cross-sectional distance than the diameter of a droplet in the droplet mixture. For example, for a droplet with a diameter of about 1 μm, a mixing channel can have a diameter of more than 1 μm. In one embodiment, a mixing channel can have a diameter that is larger than the diameter of a droplet with the largest diameter of droplets within a droplet mixture. For example, for a droplet with the largest diameter of droplets within a droplet mixture with a diameter of about 1 μm, a mixing channel can have a diameter of more than 1 μm. In one embodiment, a mixing channel can have a diameter that is at least about the sum of the diameters of any two droplets in a droplet mixture. In one embodiment, a mixing channel can have a diameter that is at least about the sum of the diameters of two or more droplets in a droplet mixture. For example, a mixing channel can have a diameter that is at least about the sum of the diameters of 3, 4, 5, 6, 7, 8, 9, 10, 15, 20, 50, 100, 500, 1000 or more droplets in a droplet mixture. In one embodiment, a mixing channel can have a diameter that is at least about the sum of the diameters of two droplets with the largest diameters of droplets within a droplet mixture.

In one embodiment, any mixing channel described herein can have a diameter and or geometry that allows for axial or turbulent mixing of droplets. For example, the diameter of the mixing channel can allow for the mixing of droplets along the direction of flow (as opposed to mixing between parallel layers of fluid as in laminar flow), such as mixing two or more droplets flowing sequentially through the mixing channel.

In one embodiment, a mixing channel can have a length that affords mixing of droplets in the droplet mixture when flowed through the mixing channel due to buoyancy mismatch between droplets and a continuous phase or a carrier fluid around the droplets.

Multiple parallel grooves or guides, or obstacles can be implemented into a mixing channel and can be used to scale-up the production of droplet mixtures, be used to mix different droplet population types, or a combination thereof.

In some embodiments, mixing can be from laminar flow, transitional flow, or turbulent flow, such as by chaotic mixing. In one embodiment, mixing comprises mixing with a force other than diffusion alone. In some embodiments, the mixing can be active mixing. Active mixing can provide more mixing of the droplets compared to mixing by passive diffusion alone. In some embodiments, active mixing can result from flow of droplets or fluids driven by pressure, buoyancy, capillary action, gravity, or any combination thereof. In some embodiments, mixing can be from advection, or advection and diffusion, for example, convection. Convection can be the sum of transport of fluid and/or droplets by diffusion and advection.

Stabilization Module/Skin Formation

The droplets or droplet mixtures generated using the systems and methods described herein can be stabilized, such as by a stabilization module, to improve droplet stability and uniformity, before, during, or after manipulation steps. In some embodiments, droplets of a first population and/or droplets of a second population can be stabilized before being combined into a droplet mixture. In some embodiments, droplets of a first population and/or droplets of a second population can be stabilized after being combined into a droplet mixture. In some embodiments, droplets of a first population, droplets of a second population, and/or droplets in a droplet mixture can be stabilized before mixing. In some embodiments, droplets in a droplet mixture can be stabilized during mixing of the droplets, such as during flow of the droplet mixture through a mixing module, such as a mixing channel. In some embodiments, droplets of a first population, droplets of a second population, and/or droplets in a droplet mixture can be stabilized after mixing. In this way, complex samples may be converted into a plurality of simpler, more easily analyzed samples, with concomitant reductions in background and assay times. The stabilized droplet populations or mixture thereof produced by the systems and methods described herein can be resistant to handling-induced and/or transferring-induced variability, such as pipette-induced variability, and can be used for instrument qualification after heating. The systems and methods described herein can be used to produce a large batch of uniform droplet mixtures that are more robust than typical pre-PCR droplets because they have been stabilized. Thus, variability in droplet size, sample partitioning in droplets, concentration of reagents, and other characteristics described above, can be avoided. Stabilization can prevent droplet coalescence, damage, shearing and/or breaking due to packing, mixing, flowing within a channel, transporting, and/or during manipulation by a user.

In some embodiments, the systems described herein comprise a heating module or member that can transfer energy to an individual droplet to form a skin around the droplet, such as described in U.S. application Ser. No. 12/976,816. In some cases, the system transfers energy to an individual droplet or an emulsion having the droplet in order to avoid or mitigate deterioration of temperature sensitive reagents. Temperature control in some cases can aid in regulating one or more properties of an individual droplet or emulsion, such as the viscosity of a droplet and/or emulsion, or the density of a droplet and/or emulsion. Upon exposure to energy, such as heat, the droplets can become encapsulated by a skin. The skin-encapsulated droplets, or capsules, can be resistant to coalescence, aggregation, damage, shearing, and/or breakage over a wide range of thermal and mechanical processing conditions. The capsules can be used to provide more stable and uniform droplet mixtures; encapsulation of samples or analytes, such as nucleic acids, proteins, or cells; and can be used in a wide range of biomedical applications, such as assays, drug delivery, vaccine delivery, housing biomolecular libraries, and clinical imaging applications.

A stabilization module can be operable to stabilize droplets by providing energy to the droplets in a first or second population of droplets, or in a droplet mixture, or any combination thereof. In some embodiments, providing energy stabilizes the droplets by inducing an increase in temperature to droplets. The energy can be thermal, electromagnetic, electrical, chemical, or mechanical energy, or any combination thereof. For example, the electromagnetic energy can be gamma rays, x-rays, ultraviolet rays, visible light, infrared rays, microwaves, radio waves, or any combination thereof. For example, the thermal energy can be heat, conduction, convection, radiation, or a combination thereof.

In some embodiments, the stabilizing module does not induce significant amplification of a signal within the droplets. In some embodiments, 90% or less of any of the droplets in the droplet mixture coalesce after being stabilized by the stabilizing module. For example 80%, 75%, 70%, 65%, 60%, 55%, 50%, 45%, 40%, 35%, 30%, 25%, 20%, 15%, 10%, 5%, 1% or less of any of the droplets in the droplet mixture coalesce after being stabilized by the stabilizing module. In a preferred embodiment, 50% or less of any of the droplets in the droplet mixture coalesce after being stabilized by the stabilizing module.

Stabilization can be implemented with the aid of a heating element, convective heating device, radiative heating device, resistive heating element, thermoelectric device, heating block, lamp, light source, microwave, radiation source, water bath, or any combination thereof, and/or any suitable device known in the art. In an example, heat is applied with the aid of a resistive heating element in thermal communication with a droplet channel, droplet intersection, mixing module, or any combination thereof. In another example, heat is applied with the aid of an IR light source in optical communication with a droplet channel, droplet intersection, mixing module, or any combination thereof. In another example, heat is applied through the employment of a water bath, for example, wherein the water is directly or indirectly in contact with the mixing channel.

A stabilization module can comprise a heating element such as a resistive heating element, in some cases comprising one or more elemental metals, such as Cu, Ta, Ti, W, Mo, Fe, Ag, Au, Pt, or any other suitable metal. The stabilization module can have a composition and dimension that is selected to provide a desired heating rate (power) to droplets flowing through the fluid flow path, including the intersection, at least a portion of the droplet channel, and/or a droplet reservoir for holding droplets. In some cases, the stabilization module is thermally coupled to fluid flow path with the aid of a heat conductor, such as, for example, a foil comprising copper or a copper alloy. In some embodiments, the stabilization module includes one or more thermoelectric devices thermally coupled to the fluid flow path. The thermoelectric device can be selected to provide a desired heating rate to droplets flowing through the fluid flow path.

The stabilizing module can comprise one or more stabilizing elements, such as energy providing elements, for example, heating elements. In such embodiments, energy can comprise a first energy provided by a first heating element and second energy provided by a second heating element, thereby allowing for temperature cycling. The first energy can provide the stabilization and the second energy can initiate a reaction within the droplets. In some cases, such as a droplet mixture flows through the mixing module, the temperature of the droplets can be cycled to induce nucleic acid amplification by employing two or more means of stabilization, such as two or more energy sources, for example, two or more light sources. In some embodiments, this can advantageously enable in-line or off-line induction of a reaction, such as nucleic acid amplification, PCR, RT-PCR, isothermal amplification, in vitro translation, and any other suitable reaction known in the art prior. In some cases, prior to temperature cycling, the droplets or droplet mixtures can be heated to induce skin formation around the droplet.

In some cases, droplets or droplet mixtures are exposed to a sequence of temperatures to enable a PCR reaction (e.g., a denaturation temperature, an annealing temperature, and an extension temperature). The temperatures may be optimized for a particular assay. Exemplary denaturation temperatures may be 94-96° C. Exemplary annealing temperatures may be 37-75° C. Exemplary extension temperatures may be 60-72°. In some cases, the droplets are exposed to temperature to enable hot-start of an enzyme, such as a polymerase. An exemplary temperature for enabling hot-start is about 95° C. In some cases, the droplets are not subjected to heat. In some cases, the droplets are not subjected to conditions to induce skin formation.

In some cases, a skin is formed around a droplet by providing energy to the carrier fluid and/or sample prior to droplet formation. The carrier fluid and/or the sample can be heated with the aid of a resistive heating element, for example, an IR light source that is in optical communication with the carrier fluid reservoir and/or the sample reservoir.

In some embodiments, a skin is formed around a droplet by heating oil in the carrier fluid reservoir. In some embodiments, any of the droplets or droplet populations or droplet mixtures can have a Reynolds number of 1, 5, 10, 25, 50, 75, 100, 200, 300, 400, 500, 600, 700, 800, 900, 1000, 1200, 1400, 1600, 1800, 2000, 2100 or less. In some embodiments, any of the droplets or droplet populations or droplet mixtures can have a Reynolds number of 2100 or less when the flow through the mixing module is laminar. In some embodiments, any of the droplets or droplet populations or droplet mixtures can have a Reynolds number of 2100 or more. In some embodiments, any of the droplets or droplet populations or droplet mixtures can have a Reynolds number of 2100 or more when the flow through the mixing module is turbulent. In some embodiments, any of the droplets or droplet populations or droplet mixtures produced herein can have a Weber number of 1, 0.9, 0.8, 0.7, 0.6, 0.5, 0.4, 0.3, 0.2, 01, or less. In some embodiments, any of the droplets or droplet populations or droplet mixtures can have a Weber number of 1 or more.

The aqueous phase of the droplets can include one or more skin forming components. A skin-forming component is any substance that promotes formation of a skin near or at the droplet boundary, for example, by serving as a structural element of the skin. Each skin-forming component can have any suitable distribution with respect to each droplet prior to skin formation. The skin-forming component can be localized selectively near or at the droplet interface, to form an interface layer, or can be distributed more uniformly throughout the aqueous phase. If distributed more uniformly, the skin-forming component can be recruited to the interface during skin formation.

The skin-forming components can include at least one skin-forming protein. The protein can be present at an effective concentration, which is an amount sufficient for detectable skin formation under the appropriate conditions (e.g., heating). Exemplary effective concentrations include at least about 0.01% or 0.03%, 0.03% to 3%, 0.05% to 2%, 0.1% to 1%, or about 0.1% by weight, among others. The protein can be described as a "non-specific blocking" or "non-specific binding" protein. The phrase "non-specific blocking" or "non-specific binding" as used herein refers generally to a capability to non-specifically bind to surfaces, that is, hydrophobic and/or hydrophilic surfaces, sometimes with the aid of heating. Non-specific blocking/binding proteins are typically water-soluble proteins, can be relatively large serum or milk proteins (among others), and/or may not interact with any of the other components of the aqueous phase in a specific binding fashion. Exemplary non-specific blocking/binding proteins that can be suitable as skin forming proteins include albumins (such as a serum albumin (e.g., from bovine (BSA), human, rabbit, goat, sheep or horse, among others)), globulins (e.g., beta-lactoglobulin), casein, and gelatin (e.g., bovine skin gelatin type B), among others.

A Young's modulus (e.g., tensile modulus or elastic modulus) can be a measure of the stiffness of the skin of a droplet. It can be the ratio of the uniaxial stress over the uniaxial strain in the range of stress in which Hooke's Law holds. The Young's modulus can be determined experimentally from the slope of a stress-strain curve created during tensile tests conducted on the skin. In some embodiments, a plurality of droplets with a skin, such as those in a droplet mixture produced using a system described herein, can have a Young's modulus of at least about 1.5 Pa ($N/m^2$ or $kg/(m \cdot s^2)$). For example, the droplets can have a Young's modulus of at least about 3, 5, 10, 15, 25, 50, 75, 100, 125, 150, 175, 200, 225, or 250 Pa ($N/m^2$ or $kg/(m \cdot s^2)$)

In some embodiments, a plurality of droplets with a skin, such as those in a droplet mixture produced using a system described herein, can have an area compressibility modulus from 0.01 mN/m to 10000 mN/m at a temperature of 25° C. For example, the area compressibility modulus can be from 0.01 mN/m to 5000 mN/m, 0.01 mN/m to 1000 mN/m, 0.01 mN/m to 500 mN/m, 0.01 mN/m to 100 mN/m, 0.01 mN/m to 10 mN/m, 0.01 mN/m to 1 mN/m, 0.01 mN/m to 0.1 mN/m, 0.1 mN/m to 10000 mN/m, 0.1 mN/m to 5000 mN/m, 0.1 mN/m to 1000 mN/m, 0.1 mN/m to 500 mN/m, 0.1 mN/m to 100 mN/m, 0.1 mN/m to 10 mN/m, 0.1 mN/m to 1 mN/m, 1 mN/m to 10000 mN/m, 1 mN/m to 5000 mN/m, 1 mN/m to 1000 mN/m, 1 mN/m to 500 mN/m, 1 mN/m to 100 mN/m, 1 mN/m to 10 mN/m, 10 mN/m to 10000 mN/m, 10 mN/m to 5000 mN/m, 10 mN/m to 1000 mN/m, 10 mN/m to 500 mN/m, 10 mN/m to 100 mN/m, 100 mN/m to 10000 mN/m, 100 mN/m to 5000 mN/m, 100 mN/m to 1000 mN/m, 100 mN/m to 500 mN/m, 500 mN/m to 10000 mN/m, 500 mN/m to 5000 mN/m, 500 mN/m to 1000 mN/m, 1000 mN/m to 10000 mN/m, 1000 mN/m to 5000 mN/m, or 5000 mN/m to 10000 mN/m at a temperature of 25° C.

A signal detected from a plurality of droplets with a skin can have a reduction in the frequency of off-amplitude events associated with the emission of the signal compared to signal detected from a substantially similar plurality of droplets without a skin, such as a droplet that has not been heat treated. In some embodiments, the frequency of off-amplitude events associated with the emission of a detectable signal from a plurality of droplets with a skin, such as a plurality of heat treated droplets, can be 50% or less. For example, the frequency of off-amplitude events associated with the emission of a detectable signal from a plurality of droplets with a skin can be 45%, 40%, 35%, 30%, 25%, 20%, 19%, 18%, 17%, 16%, 15%, 14%, 13%, 12%, 11%, 10%, 9%, 8%, 7%, 6%, 5%, 4%, 3%, 2%, 1%, or less, or can be 0%.

Following formation, one or more droplets with samples or sample partitions flow along the droplet channel as an emulsion. The flow rate of the emulsion can be selected to facilitate skin formation. As described above the flow rate of the emulsion (including a drop in the emulsion) can be from 1 μl/minute to 10000 μl/minute.

A stabilizing module can include 2, 3, 4, 5, 6, 7, 8, 9, 10, 11, 12, 13, 14, 15, 16, 17, 18, 19, or 20, or more stabilizing members operable to transfer thermal energy to the droplets at any stage of flow through the system. A stabilizing member can be operable for contact energy transfer or noncontact energy transfer. A stabilizing member can include a thin film heating element, a heating lamp, a metal heating block, a ceramic heating block, a laser, a water bath, a thermal cycler, a custom mechanical thermal block, or any combination thereof. In some embodiments, a heating member can use IR radiation, use hot air cycling, use microwave irradiation, or any combination thereof.

A stabilizing module of any system described herein can be used to heat the droplets and can include any stabilizing member operable to transfer thermal energy to the droplets that can cause skin formation. A stabilizing member can be in thermal communication with at least a portion of any fluid flow path of the systems described herein. For example, stabilizing member can be in thermal communication with at least a portion of a first droplet flow path, a second droplet flow path, an intersection, a droplet combining module, a mixing flow path, or any combination thereof. A stabilizing module can comprise one or more stabilizing members operable to transfer thermal energy to the droplets at any stage of flow through the system. For example, a stabilizing member can be operable to transfer thermal energy to the droplets as they flow through the system. For example, a stabilizing member can be operable to transfer thermal energy to droplets as they are formed from a droplet generator, as they flow through a droplet channel, as they flow through an intersection, as they flow through a combining member as they flow through a mixing channel, as they are collected in a collection vessel, or any combination thereof. In some embodiments, the stabilizing member can be operable to transfer thermal energy to a droplet mixture after collection of the droplet mixture in a collection vessel.

Temperature control of a stabilizing member can be designed for isothermal or gradient mode control of heat disbursement within the system, such as isothermal or gradient mode control of heat disbursement across a mixing channel. For example, the temperature in one portion of a mixing channel can be the same as an upstream or downstream portion of the mixing channel, the temperature in one portion of a mixing channel can be higher than an upstream portion of the mixing channel, the temperature in one portion of a mixing channel can be lower than an upstream portion of the mixing channel, the temperature in one portion of a mixing channel can be lower than a downstream portion of the mixing channel, the temperature in one portion of a mixing channel can be higher than a downstream portion of the mixing channel, or any combination thereof. For example, during skin formation the droplets can be heated along a temperature gradient. The temperature gradient can have a first temperature at a first portion of the droplet channel and a second temperature at a second portion of the droplet channel downstream of the first portion.

The temperature gradient can have temperatures from about 4° C. and 98° C., such as 55° C. and 98° C. In an example, the temperature at the first portion is 55° C. and the temperature at the second portion is 75° C., and the temperature from the first portion to the second portion is increased (e.g., gradually increased) from 55° C. to 75° C.

Alternatively, the droplet can be stabilized at a constant or variable temperature for a time sufficient to induce skin formation. In an example, the droplet is heated at a temperature from 4° C. to 98° C. for a time period of 0.01 seconds or more. For example, droplets can be heated at a temperature from 4° C. to 99° C. for 0.01 or more seconds, from 30° C. to 98° C. for 5 or more seconds, from 50° C. to 65° C. for 5 or more seconds, from 30° C. to 75° C. for from 5 seconds to 2 hours, or from 75° C. to 95° C. for from 5 seconds to 30 minutes.

Collection Module

A collection module of the systems described herein can be operable to collect droplet mixtures as the mixtures exit from the outlets of one or more mixing channels. Droplet mixtures can be collected into one or more similar or different vessels, such as a single tube or multiple wells of a plate, or any vessel known in the art. The collection vessels of the collection module can include one or more containers suitable for droplet mixture or sample collection. For example, collection vessels can include bottles, jars, vials, boxes, tubes, drums, dishes, bags, multiwell plates (e.g. 96-well or 384-well plates), microplates, or the like.

Droplet mixture collection can be aided through the use of a manifold or multiport design to distribute droplet mixtures. A manifold for droplet mixture distribution can be implemented into the system downstream of the one or more mixing channels after droplet generation, mixing, and optionally, thermal processing but before droplet mixture collection. In some embodiments, the manifold for droplet distribution can be operable to distribute droplet mixtures into various collection vessels or containers. In some embodiments, the manifold for droplet distribution can be operable to distribute various volumes of droplet mixtures into the various collection vessels or containers.

Shipping and Storage of Droplets

In some embodiments, after collection of droplets, such as a mixed droplet population, it is desirable to store and or transport the droplets for later use, for example for shipping to a customer. Care should be taken when transporting and/or storing droplets because the droplets may become damaged upon manipulation of the droplets for or during storage and/or transporting. In some embodiments, droplets can be collected and an assay can be performed on the droplets at a later time or at a different location from where the droplets were generated, combined, mixed, and/or collected. Any of the droplets or populations of droplets described herein can be prepared for transport and/or storage. In one embodiment, droplets can be prepared in a vessel, such as a well, tube, bag, or plate, for shipping and/or storage. Droplets can be shipped by any method know in the art, for example, by driving, flying, boating, mail, or any combination thereof. The vessel used for preparation of the droplets for transport can be any suitable vessel with any suitable volume capable of holding the droplets, for example, a well, plate, tube, or multi-well plate. In some embodiments, the vessel can comprise a lid, for example a sealable lid.

In some embodiments, the volume of oil, in relation to the volume of the vessel used in the preparation of the droplets for shipping and/or storage, is important. In one embodiment, a preferred range of oil volume is from 0-6% of the volume of the vessel, such as from 0%-1%, 0%-2%, 0%-3%, 0%-4%, 0%-5%, 1%-2%, 1%-3%, 1%-4%, 1%-5%, 1%-6%, 2%-3%, 2%-4%, 2%-5%, 2%-6%, 3%-4%, 3%-5%, 3%-6%, 4%-5%, 4%-6%, or 5%-6% of the volume of the vessel. For example, for a vessel of 250 µL, a preferred range of oil volume is from 0-15 µl.

In some embodiments, the volume of droplets, in relation to the volume of the vessel used in the preparation of the droplets for shipping and/or storage, is important. In one embodiment, a preferred range of droplet volumes is from 11.2%-100% of the volume of the vessel, such as from 11.2%-90%, 11.2%-80%, 11.2%-70%, 11.2%-60%, 11.2%-50%, 11.2%-40%, 11.2%-30%, 11.2%-20%, 20-100%, 30-100%, 40-100%, 50-100%, 60-100%, 70-100%, 80-100%, 90-100%, 20-90%, 20-80%, 20-70%, 20-60%, 20-50%, 20-40%, 20-30%, 30-80%, 30-70%, 30-60%, 30-50%, 30-40%, 40-90%, 40-80%, 40-70%, 40-60%, 40-50%, 50-90%, 50-80%, 50-70%, 50-60%, 60-90%, 60-80%, 60-70%, 70-90%, 70-80%, or 80-90%, of the volume of the vessel. For example, for a vessel of 250 µL, a preferred range of droplet volume is from 28-250 µl.

In some embodiments, the volume of head space in a vessel, in relation to the volume of the vessel used in the preparation of the droplets for shipping and/or storage, is important. The head space can be the volume of air or empty volume in the vessel, for example, the volume not included in the volume of droplets and oil. In one embodiment, a preferred range of head space volumes is from 0-88.8% of the volume of the vessel, such as from 0%-80%, 0%-70%, 0%-60%, 0%-50%, 0%-40%, 0%-30%, 0%-20%, 0%-10%, 10%-88.8%, 10%-80%, 10%-70%, 10%-60%, 10%-50%, 10%-40%, 10%-30%, 10%-20%, 20-88.8%, 20%-80%, 20%-70%, 20%-60%, 20%-50%, 20%-40%, 20%-30%, 30-88.8%, 30%-80%, 30%-70%, 30%-60%, 30%-50%, 30%-40%, 40-88.8%, 40%-80%, 40%-70%, 40%-60%, 40%-50%, 50-88.8%, 50%-80%, 50%-70%, 50%-60%, 60-88.8%, 60%-80%, 60%-70%, 70-88.8%, 70%-80%, or 80%-88.8% of the volume of the vessel. For example, for a vessel of 250 µL, a preferred range of head space volume is from 0-222 µl.

In some embodiments, to increase droplet recovery in vessels with greater than 10% head space volume, preferred oil volume can be from 4-6% of the vessel volume, such as 4%-5%, or 5%-6% of the vessel volume. For example, for a vessel of 250 µL, to increase droplet recovery in vessels with greater than 10% head space volume, preferred oil volume can be from 10 µL to 15 µL. Such volumes of oil can ensure significant numbers of droplets can be picked up and read in an assay upon use.

In some embodiments, preferred volume fractions of droplets and oil was found to minimize droplet losses or damage and, for example, maintain a high number of stable, high quality droplets. In some embodiments, preferred volume fractions of droplets and oil to minimize droplet losses or damage can be 90% or more of the vessel volume. For example, volume fractions of droplets and oil to minimize droplet losses or damage can be 95%, 97%, 98%, 99% or more, or 100% of the vessel volume. For example, for a vessel of 250 µL, preferred volume fractions of droplets and oil to minimize droplet losses or damage can be 210 µL droplets and 15 µL oil.

Preparation of droplets for shipping can allow for droplets to remain stable. For example, preparation of droplets for shipping can allow for droplets to maintain original dispersity, such as monodispersity of droplet size, to have a reduced ability to coalescence, to have a reduced susceptibility to breakage, to be less susceptible to shearing, and/or to be less susceptible to damage. For example, droplets can be prepared for shipping such that after shipping over a distance of greater than 0.5 km, the droplets remain stable, maintain original dispersity, have a reduced ability to coalescence, have a reduced susceptibility to breakage, have a reduced susceptibility to shearing, and/or have a reduced susceptibility to damage. For example, droplets can be prepared for shipping such that after shipping over a distance of greater than 1, 2, 3, 4, 5, 6, 7, 8, 9, 10, 25, 50, 75, 100, 250, 500, 750, 1000, 2000, 3000, 4000, or 5000 km, the droplets remain stable, maintain original dispersity, have a reduced ability to coalescence, have a reduced susceptibility to breakage, have a reduced susceptibility to shearing, and/or have a reduced susceptibility to damage. Droplets can be prepared for shipping such that after shipping over a distance of greater than 0.5 km, the droplets remain stable, maintain original dispersity, have a reduced ability to coalescence, have a reduced susceptibility to breakage, have a reduced susceptibility to shearing, and/or have a reduced susceptibility to damage, such that a detectable signal and/or the data quality of the droplets degrades 50% or less. For example, droplets can be prepared for shipping such that after shipping over a distance of greater than 0.5 km, the droplets remain stable such that a detectable signal and/or the data quality of the droplets degrades 45%, 40%, 35%, 30%, 25%, 20%, 15%, 10%, 5%, 1%, or less. For example, droplets can be prepared for shipping such that after shipping over a distance of greater than 1, 2, 3, 4, 5, 6, 7, 8, 9, 10, 25, 50, 75, 100, 250, 500, 750, 1000, 2000, 3000, 4000, or 5000 km, the droplets remain stable, maintain original dispersity, have a reduced ability to coalescence, have a reduced susceptibility to breakage, have a reduced susceptibility to shearing, and/or have a reduced susceptibility to damage, such that a detectable signal and/or the data quality of the droplets degrades 45%, 40%, 35%, 30%, 25%, 20%, 15%, 10%, 5%, 1%, or less. In some embodiments, droplets can be prepared for shipping such that after shipping over a distance of greater than 1, 2, 3, 4, 5, 6, 7, 8, 9, 10, 25, 50, 75, 100, 250, 500, 750, 1000, 2000, 3000, 4000, or 5000 km, the droplets remain stable, maintain original dispersity, have a reduced ability to coalescence, have a reduced susceptibility to breakage, have a reduced susceptibility to shearing, and/or have a reduced susceptibility to damage. such that a detectable signal can be detected in 10% or more of the total number of droplets. For example, droplets can be prepared for shipping such that after shipping over a distance of greater than 0.5, 1, 2, 3, 4, 5, 6, 7, 8, 9, 10, 25, 50, 75, 100, 250, 500, 750, 1000, 2000, 3000, 4000, or 5000 km, the droplets remain stable, maintain original dispersity, have a reduced ability to coalescence, have a reduced susceptibility to breakage, have a reduced susceptibility to shearing, and/or have a reduced susceptibility to damage, such that a detectable signal can be detected in 15%, 20%, 25%, 30%, 35%, 40%, 45%, 50%, 55%, 60%, 65%, 70%, 75%, 80%, 85%, 90%, 95%, 99%, or more of the total number of droplets. In some embodiments, droplets can be prepared for shipping such that after shipping over a distance of greater than 0.5, 1, 2, 3, 4, 5, 6, 7, 8, 9, 10, 25, 50, 75, 100, 250, 500, 750, 1000, 2000, 3000, 4000, or 5000 km, the droplets remain stable, maintain original dispersity, have a reduced ability to coalescence, have a reduced susceptibility to breakage, have a reduced susceptibility to shearing, and/or have a reduced susceptibility to damage, such that a frequency of off-amplitude events associated with the emission of a detectable signal from the droplets is 50%, 45%, 40%, 35%, 30%, 25%, 20%, 15%, 10%, 5%, 1%, or less. Instability, coalescence, shearing, breakage or damage to droplets can also impact the signals from droplets in other ways that can lead to a reduction in the quality of data obtained from the shipped droplets.

Preparation of droplets for storage can allow for droplets to remain stable. For example, droplets can be prepared for storage such that after storage for a time of greater than 0.5 hr, the droplets remain stable. For example, droplets can be prepared for storage such that after storage for a time of greater than 0.5, 1, 2, 3, 4, 5, 6, 7, 8, 9, 10, 12, 15, 18, 21, or 24 hrs, or 2, 3, 4, 5, 6 or seven days, or 2, 3, or 4 weeks, or 1, 2, 3, 4, 5, 6, 7, 8, 9, 10, 11, or 12 months, or 2, 3, 4, 5, 6, 7, 8, 9, or 10 years, the droplets remain stable, maintain original dispersity, have a reduced ability to coalescence, have a reduced susceptibility to breakage, have a reduced susceptibility to shearing, and/or have a reduced susceptibility to damage. Droplets can be prepared for storage such that after storage for a time of greater than 0.5 hr, the droplets remain stable, maintain original dispersity, have a reduced ability to coalescence, have a reduced susceptibility to breakage, have a reduced susceptibility to shearing, and/or have a reduced susceptibility to damage, such that a detectable signal and/or the data quality of the droplets degrades 50% or less. For example, droplets can be prepared for storage such that after storage for a time of greater than 0.5 hr, the droplets remain stable, maintain original dispersity, have a reduced ability to coalescence, have a reduced susceptibility to breakage, have a reduced susceptibility to shearing, and/or have a reduced susceptibility to damage, such that a detectable signal and/or the data quality of the droplets degrades 45%, 40%, 35%, 30%, 25%, 20%, 15%, 10%, 5%, 1%, or less. For example, droplets can be prepared for storage such that after storage for a time of greater than 1, 2, 3, 4, 5, 6, 7, 8, 9, 10, 12, 15, 18, 21, or 24 hrs, or 2, 3, 4, 5, 6 or seven days, or 2, 3, or 4 weeks, or 1, 2, 3, 4, 5, 6, 7, 8, 9, 10, 11, or 12 months, or 2, 3, 4, 5, 6, 7, 8, 9, or 10 years, the droplets remain stable, maintain original dispersity, have a reduced ability to coalescence, have a reduced susceptibility to breakage, have a reduced susceptibility to shearing, and/or have a reduced susceptibility to damage, such that a detectable signal and/or the data quality of the droplets degrades 45%, 40%, 35%, 30%, 25%, 20%, 15%, 10%, 5%, 1%, or less. In some embodiments, droplets can be prepared for storage such that after storage for a time of greater 0.5, 1, 2, 3, 4, 5, 6, 7, 8, 9, 10, 12, 15, 18, 21, or 24 hrs, or 2, 3, 4, 5, 6 or seven days, or 2, 3, or 4 weeks, or 1, 2, 3, 4, 5, 6, 7, 8, 9, 10, 11, or 12 months, or 2, 3, 4, 5, 6, 7, 8, 9, or 10 years, the droplets remain stable, maintain original dispersity, have a reduced ability to coalescence, have a reduced susceptibility to breakage, have a reduced susceptibility to shearing, and/or have a reduced susceptibility to damage, such that a detectable signal can be detected in 10% or more of the total number of droplets. For example, droplets can be prepared for storage such that after storage for a time of greater 0.5, 1, 2, 3, 4, 5, 6, 7, 8, 9, 10, 12, 15, 18, 21, or 24 hrs, or 2, 3, 4, 5, 6 or seven days, or 2, 3, or 4 weeks, or 1, 2, 3, 4, 5, 6, 7, 8, 9, 10, 11, or 12 months, or 2, 3, 4, 5, 6, 7, 8, 9, or 10 years, the droplets remain stable, maintain original dispersity, have a reduced ability to coalescence, have a reduced susceptibility to breakage, have a reduced susceptibility to shearing, and/or have a reduced susceptibility to damage, such that a detectable signal can be detected in 15%, 20%, 25%, 30%, 35%, 40%, 45%, 50%, 55%, 60%, 65%, 70%, 75%, 80%, 85%, 90%, 95%, 99%, or more of the total number of droplets. In some embodiments, droplets can be prepared for storage such that after storage for a time of greater 0.5, 1, 2, 3, 4, 5, 6, 7, 8, 9, 10, 12, 15, 18, 21, or 24 hrs, or 2, 3, 4, 5, 6 or seven days, or 2, 3, or 4 weeks, or 1, 2, 3, 4, 5, 6, 7, 8, 9, 10, 11, or 12 months, or 2, 3, 4, 5, 6, 7, 8, 9, or 10 years, the droplets remain stable, maintain original dispersity, have a reduced ability to coalescence, have a reduced susceptibility to breakage, have a reduced susceptibility to shearing, and/or have a reduced susceptibility to damage, such that a frequency of off-amplitude events associated with the emission of a detectable signal from the droplets is 50%, 45%, 40%, 35%, 30%, 25%, 20%, 15%, 10%, 5%, 1%, or less. Instability, coalescence, shearing, breakage or damage to droplets can also impact the signals from droplets in other ways that can lead to a reduction in the quality of data obtained from the stored droplets.

Figure 7A:
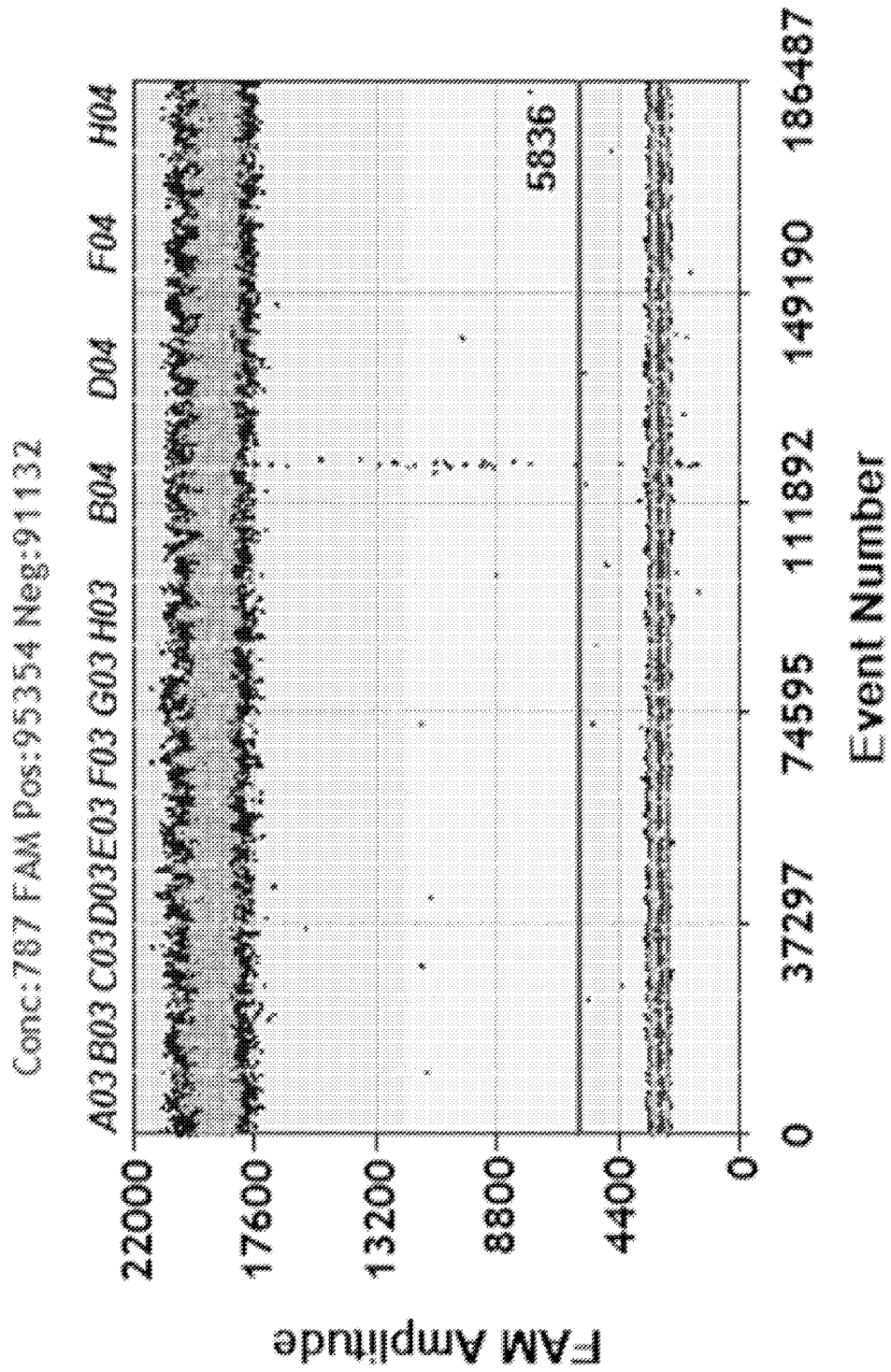
FIG. 7A provides a droplet reader amplitude plot of 6-carboxyfluorescein (FAM) amplitude determined by detecting fluorescence emission from freshly prepared droplets with good droplet quality before storage or transport of the droplets.
Figure 7B:
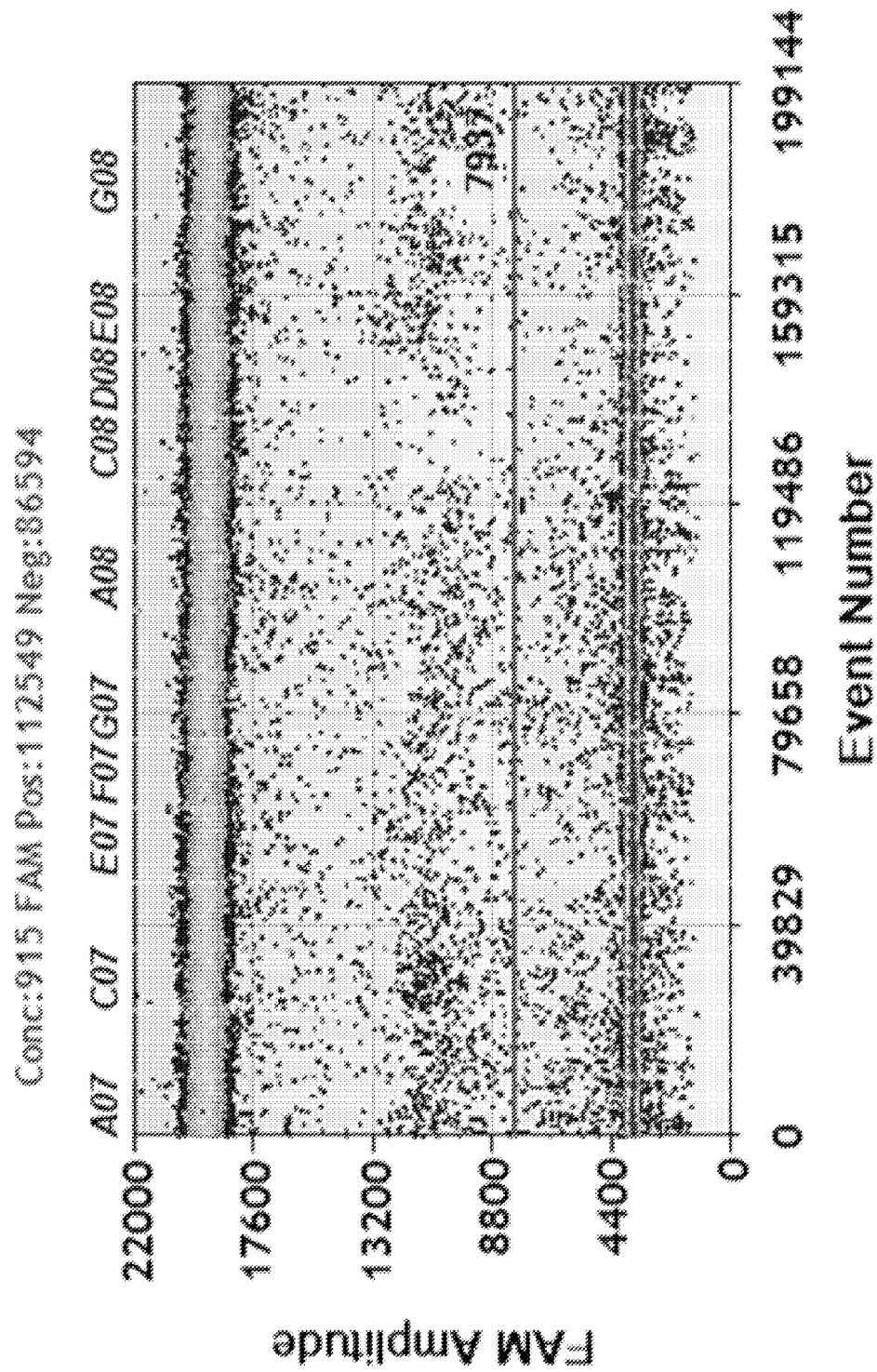
FIG. 7B provides a droplet reader amplitude plot of 6-carboxyfluorescein (FAM) amplitude determined by detecting fluorescence emission from droplets with poor droplet quality after storage or transport of the droplets under non-preferred conditions.
Figure 7C:
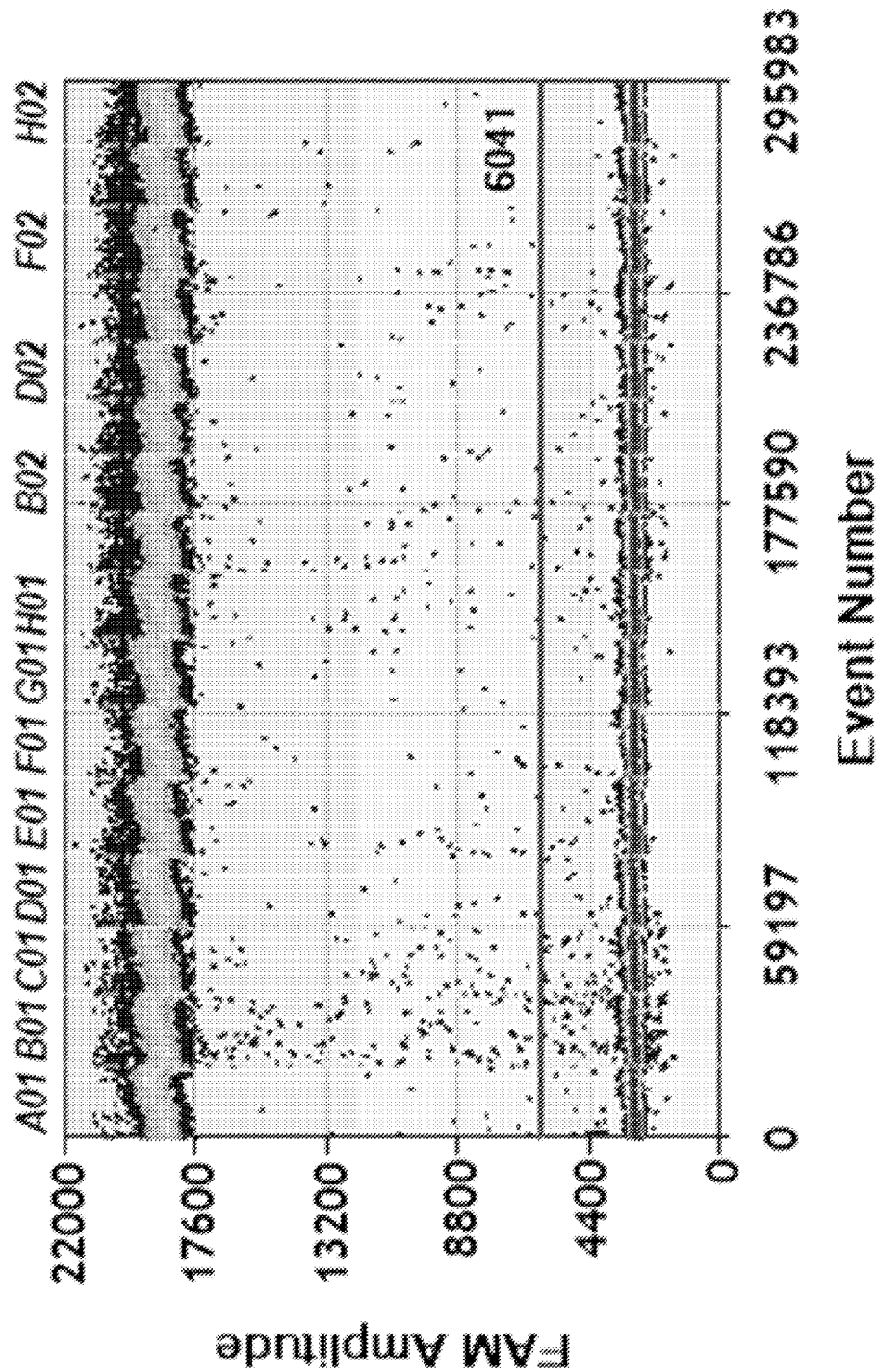
FIG. 7C provides a droplet read amplitude plot of simulated 6-carboxyfluorescein (FAM) amplitude determined by detecting fluorescence emission from droplets after storage or transport of the droplets under preferred conditions.

Droplets can be pipetted into 96-well plates (well volume=250 ul), and sealed with a heat sealer and pierceable metal foil. The total volume fraction of drops in each well and the corresponding fraction of continuous phase oil in the well with the drops can be varied prior to sealing the plate. An aliquot of droplets from a bulk generation batch can run on a droplet reader, such as a Bio-Rad QX100 or QX200 Droplet Reader, and can serve as a positive control for droplet quality. Once plates are filled and sealed, they can be packaged with support, for example by foam cushioning in cardboard shipping boxes. The boxes can be sealed and sent to another location, for example to a user or collaborator. Droplets can shipped back to the original location from which they were shipped or any other location without opening the box. Upon receipt of the droplets, vessels can be removed from the box and assayed, for example immediately run on a QX100 Droplet Reader. Data quality can then be assessed, for example, using QuantaSoft and QuantaGalaxy software (Bio-Rad). Example 2 describes one example of preparation of droplets for maintaining droplet stability during shipping. FIG. 7A-C show graphical depictions of 6-carboxyfluorescein (FAM) concentrations determined by detecting fluorescence emission from droplets before or after storage or transport of the droplets under preferred and non-preferred conditions.

Droplet Mixtures for Use as Calibration Controls

The present disclosure provides a system, including methods and apparatus, for generating calibration control samples, for example, droplet mixtures for droplet-based tests of nucleic acid amplification, which can be used to qualify or calibrate instruments used to detect signals from droplets, or those described in U.S. application Ser. No. 13/245,575. Droplet readers can be qualified by isolating a reader step (analysis) from droplet generation, removing variables from the droplet generator, the consumable chip, thermocycling, and user pipetting. In the case of FAM drops, the thermal cycling step is also eliminated, which may reduce variation that arises during thermocycling, such as errors caused by air-droplet interfaces. The droplet mixtures can be generated and then collected and stored until subsequent analysis, such as using a reader or detection system, or any analysis system known in the art.

Digital PCR samples may be simulated by volumetrically mixing simulated positive (high fluorescence amplitude) and negative (low fluorescence amplitude) droplets, or different colored droplets in a uniform manner over time. Such simulated samples can be repeatable, precise and accurate as measured by a droplet reader.

At least a subset or all of the droplets in the droplet mixtures generated by using the system and methods described herein can include a partition of one or more samples to be tested and can be capable of amplification of at least one test nucleic acid target, if present, in the partition. In some embodiments, the droplets can be capable of amplification of a test nucleic acid target and a control nucleic acid target. The droplets in the droplet mixtures collectively or each can include a dye, or at least a first dye and a second dye, for example, such that the two dyes are the same or different color. In some embodiments, the droplets in the droplet mixtures can be of at least two types, such as two or more types of test droplets, test droplets and calibration droplets, or test droplets and control droplets, among others. In some embodiments, the two or more types of droplets can be distinguishable based on distinct temporal positions of the droplet types in a flow stream (or distinct times of exit from the flow stream, e.g., distinct times at which the droplets are collected in one or more detection chambers for imaging), the presence of respective distinct dyes in the droplet types, distinguishable signal intensities of the same dye (or different dyes), or a combination thereof, among others.

Signals, such as fluorescence signals, can be detected from the droplets in the droplet mixtures. The signals can include test signals, calibration signals, control signals, reference signals, or any combination thereof. Calibration signals can be signals of low, high, negative, or positive signal, such as fluorescent signal amplitude. In some embodiments, test signals and control signals can indicate respectively whether amplification of a test nucleic acid target and a control nucleic acid target occurred in individual droplets. In some embodiments, detection can include exciting first and second dyes with a same wavelength of excitation light and detecting emitted light from the first and second dyes at least substantially independently from one another in respective first and second detector channels.

The signals detected can be analyzed to determine a test result related to a presence, number, or concentration of a test nucleic acid target in the sample. In some embodiments, analysis can include transforming test signals based on reference signals to reduce variation in the test signals. The test signals and the reference signals can be detected in respective distinct detector channels or in the same detector channel. In some embodiments, the reference signals can be provided by a second dye that is not coupled to an amplification reaction and thus can serve as a passive reference. In some embodiments, the reference signals of the droplets in the droplet mixtures can be provided by control signals detected from a control amplification reaction performed after generation and collection of droplet mixtures. The control amplification reaction can measure amplification of an exogenous or endogenous template. In some embodiments, analysis can include comparing test signals, or a transformed set of the test signals, to a signal threshold to assign individual droplets as positive or negative for a test nucleic acid target, and estimating a number of molecules of the test nucleic acid target in the sample based on the comparison. In some embodiments, analysis can include analyzing control signals to determine a control value corresponding to a number and/or fraction of the droplets that are amplification-positive for a control nucleic acid target, and interpreting a test result, such as determining its validity, based on the control value. In some embodiments, analysis of test signals and/or control signals can include clustering one or more populations of the test signals and/or control signals from droplets into separate populations, or clusters, of droplets in one or two dimensions. In some embodiments, analysis can include using algorithms, such as clustering algorithms. Algorithms can be used to identify clusters of droplets in one or two dimensions. For example, clustering algorithms can be used to identify 1, 2, 3, 4, 5, 6, 7, 8, 9, 10, or more clusters of droplets in one or two dimensions. Detector optics, particularly excitation sources and optical filters, may be selected to optimize the separation of clusters. For example, two clusters might be substantially overlapping (hard to separate) at a first wavelength condition but substantially nonoverlapping at a second wavelength condition. Detectors with spectrophotometer gratings or exchangeable filter sets could provide greater flexibility in wavelength selection.

The systems disclosed herein can generate droplet mixtures that offer improved and high throughput instrument qualification, calibration and/or substantial improvements in the accuracy and/or reliability of droplet-based amplification tests. Exemplary capabilities can include any combination of correcting or minimizing variations in the fluorescence signal to increase the accuracy of droplet PCR results; providing an internal indicator of whether nucleic acid amplification failed (e.g., PCR inhibition from interfering components in the sample, incorrect sample and reagent mixing, incorrect thermal cycling, incorrect droplet formation); providing measurement of droplet volumes without having to add additional hardware components; providing measurement of changes in the baseline fluorescence signal (i.e., baseline drift); providing calibration of a droplet detector before and/or during a run; monitoring the performance of quantitative droplet PCR measurements and data processing algorithms before and/or during a run; verification of droplet integrity (e.g., absence of coalescence); obtaining information on droplet generation and detection frequency (spatially and temporally) using an in-line detector; measuring variations and comparing them to predefined tolerances; processing of raw droplet PCR data to correct for variations and increase test accuracy and performance; incorporating control assays preferably using a single excitation source; calibrating or testing fluid routines; calibrating or testing tubing volumes; or quantifying more than one species of genetic target by amplifying and detecting more than one species of genetic target in individual droplets.

Any of the samples and/or reagents disclosed herein can be stored and/or supplied in pre-formed droplet mixtures. Droplet mixtures can, for example, be pre-formed using the systems and methods described herein. Pre-formed droplets can be mixed with droplets formed by droplet generators of the systems described herein before being subjected to analysis by a detection instrument.

Test reagents can be any reagents used to test for amplification of one or more targets, such as one or more primary targets, in partitions of a sample. Primary targets can comprise any targets that are of primary interest in a test. Primary targets can be present at an unknown level in a sample, prior to performing tests on the sample. Test reagents can include one or more sets of target reagents conferring specificity for amplification of one or more particular nucleic acid targets to be tested in a sample. Thus, the test reagents can include at least one pair (or two or more pairs) of primers capable of priming amplification of at least one (or two or more) nucleic acid target(s). The test reagents also can comprise at least one reporter to facilitate detecting amplification of each test target, a polymerase (e.g., a heat stable polymerase), dNTPs, and/or the like. The test reagents can enable detection of test signals from droplets.

Control reagents can be any reagents used to control for test signal variation (generally, variation other than that produced by differences in amplification) and/or to interpret results obtained with the test reagents (such as a reliability and/or validity of the results). The control reagents can permit control signals and/or reference signals to be detected from droplets, either the same or different droplets from the test signals. Control reagents can be mixed with test reagents prior to droplet formation and control droplets containing control reagents can be produced separately from the test droplets and introduced independently of the sample.

The control reagents can provide instrument controls, that is, controls for variation introduced by the system, its environment, or a combination thereof. Thus, instrument controls can control for variation in droplet volume, droplet detection efficiency, detector drift, and the like. Reference signals can be detected from droplets containing control reagents that function as instrument controls.

The control reagents can provide amplification controls, such as controls that test for secondary or control amplification in droplets. The control reagents thus can include reagents used to test for amplification of at least one secondary or control target in droplets. The secondary or control target can be of secondary interest in a test, and/or can be present at a known or expected level in the sample, among others. The control reagents can include one or more sets of target reagents conferring specificity for amplification of one or more control nucleic acid targets to be tested in droplets. The control reagents can include at least one pair of primers capable of priming amplification of at least one control nucleic acid target. The control reagents also can comprise at least one reporter to facilitate detecting amplification of each control target, a polymerase, such as a heat stable polymerase, dNTPs, or any suitable combination of these control reagents can be supplied by the test reagents. Control signals can be detected from control reagents that function as amplification controls.

Calibration reagents can be any reagents used to calibrate system operation and response. Droplet mixtures containing a calibration reagent, such as calibration droplets, can be introduced into a flow stream of a detection instrument, for the purpose of calibrating the system, such as calibrating flow rates, excitation power, optical alignment, detector voltage, amplifier gain, droplet size, droplet spacing, signal compensation between channels, color compensation between channels, signal correction between channels, color correction between channels, or any combination thereof. Calibration droplets can be introduced into a flow stream of a detection instrument before, during, and/or after introduction of test droplets into the flow stream. In some embodiments, the level of a dye within control droplets can be used to calibrate and validate a detector instrument response, such as by using a pair of dye concentrations providing calibration signals that bracket an intended measuring range and that are disposed near upper and lower ends of the measuring range. For example, droplets of known size and containing one or more known dye concentrations can be prepared by the system. In some embodiments, calibration droplets can comprise fluorescent particles such as dyes, quantum dots, or polymer beads.

The droplets of a droplet mixture can be introduced into a flow stream upstream of a detector. All of the droplets can be introduced into the flow stream at the same position or the droplets, particularly droplets of different mixtures, can be introduced at two or more distinct positions. The droplets mixtures can be subjected to conditions that facilitate amplification. For example, the droplet mixtures can be heated and/or can be heated and cooled repeatedly (thermally cycled). Signals can be detected from the droplets in the droplet mixtures. The signals can include test signals, control signals, reference signals, calibration signals, or any combination thereof. The signals can be analyzed. Analysis can include transforming test signals. Analysis also or alternatively can include comparing test signals or transformed test signals to a signal threshold to assign individual droplets as being positive or negative for amplification of a nucleic acid target. A number or fraction of target-positive droplets can be determined based on results of the comparison. Analysis further can include estimating a presence of a nucleic acid target in the sample. The estimated presence can be no target in the sample. Estimation of the presence can be performed using Poisson statistics.

Two or more amplification mixtures can be applied to the droplet generators of the system. The amplification mixtures can incorporate samples, target reagents including a first dye, and a second dye. The second dye and the target reagents can be mixed with one another before introduction into system or can be mixed within the system. Target reagents can provide primers for amplification of a nucleic acid target, and the first dye can enable detection of whether amplification occurred. The first and second dyes can be fluorescent dyes that are distinguishable optically. The second dye can be a passive reference or instrument control. In other words, the second dye can provide a detectable signal having an intensity that is at least substantially independent of the extent of amplification, if any, of any nucleic acid target.

Target reagents can include a reporter, such as a probe, and target-specific forward and reverse primers. Probes can be energy transfer probes, such as a TAQMAN probe, including nucleic acids, such as oligonucleotides, that bind to amplified targets, and energy transfer pairs connected to strands. The energy transfer pairs can, for example, be formed by dyes and quenchers.

Control reagents can include second dyes. The second dyes can be connected to nucleic acids, such as oligonucleotides. Connection to the oligonucleotides can be covalent and/or through a binding interaction. Connection of the second dyes to oligonucleotides or other water-soluble molecules can improve retention of the second dyes in the aqueous phase of droplets and/or can facilitate distribution of the dyes throughout the aqueous phase, among others.

Test signal variation can introduce errors in data processing. As a result, some of the test signals can be erroneously classified as positives or negatives. Variation of the test signals can be mirrored by variation of the reference signals detected from the same droplets. Accordingly, the test signals can be transformed based on the reference signals to correct for variation in the test signals. The test signals can be transformed by any suitable operation or set of operation involving the reference signals. For example, the test signals can be transformed through dividing test signals by reference signals, such as dividing each test signal by its corresponding reference signal, which can be described as normalizing the test signals. Alternatively, the test signals can be transformed based on the reference signals by, for example, baseline subtraction, distance from the regression line, or the like. A transformation can compensate for variations in the test channel. This compensation or correction can make the test signals, such as negative test signals and positive test signals, more uniform in value or more Gaussian. The transformation also or alternatively can reduce the frequency of outliers and/or the overlap of the distributions of positive and negative signals.

Calibration droplets and test droplets in a droplet mixture generated using the systems and methods of the present disclosure can be separated temporally in a detector instrument flow stream, such that each type of droplet is identifiable based on its time of arrival at the detection station. Thus, the calibration and test droplets can be distinguishable based on signal intensity, but can be distinguishable temporally. In particular, the test and calibration droplets in a droplet mixture can be separated by a spatial gap, which can identify a transition between droplet types.

Calibration droplets can include two or more types of droplets, which can be introduced as a droplet mix. For example, a set of stronger calibration signals followed by a set of weaker calibration signals produced by distinct types of calibration droplets within a droplet mixture can be obtained. Stronger and weaker calibration signals can correspond in intensity to respective positive test signals and negative test signals. In other embodiments, only one type or two or three or more types of calibration droplets within a droplet mixture can be used, and can be configured respectively to provide one or two or three or more intensities of calibration signals.

Calibration and sample testing can be performed with calibration and test droplets within a droplet mixture and thus not distinguishable temporally. Intermixed calibration and test droplets can be distinguishable by incorporating distinguishable dyes into the respective droplet types and, optionally, by detection of the distinguishable dyes at respective distinct wavelengths. Alternatively, or in addition, calibration droplets and test droplets can be distinguishable according to signal intensity detected at the same wavelength and optionally from the same dye. In particular, calibration droplets can be designed to have one or more signal intensities outside the signal range of test droplets (i.e., the signal range provided by the collective distribution of signal intensities from negative and positive test droplets). Thus, calibration droplets in a mixture of droplets can be identified based on their calibration signals having signal intensities above or below the signal range of test droplets, which can be in the same droplet mixture.

The reference droplets can be formed with the same, or two or more discrete amounts of dye. Accordingly, without signal variation generated by the system, the reference droplets can produce reference signals of the same intensity. Variation in reference signal intensity can be mirrored by corresponding changes in the intensity of test signals. For example, the intensity of reference signals and negative test signals can show a gradual increase with respect to time. As a result, test signals from amplification-negative droplets can produce false positives.

Variation in test signals can be reduced by transforming the test signals based on reference signals to produce normalized test signals. Transformation can, for example, be performed by transforming each test signal based on one or more reference signals temporally proximate to the test signal, a weighted average of reference signals temporally proximate to the test signal, a sliding window of averaged reference signals that overlaps the test signal, or the like. Transformation before comparing test signals to a threshold can reduce the incidence of false positives, the incidence of false negatives, or both.

The droplet mixtures described herein can also be used for testing amplification of at least a pair of nucleic acid targets in the droplets. Any combination of the droplet populations containing any combination of samples, test reagents, control reagents, and control templates can be mixed with one another within the systems described herein. Test reagents and control reagents can provide primers for respective amplification of at least one test target and at least one control target. Amplification of the test and control targets can, for example, be detected via a first dye and a second dye, respectively, which can be included in respective first and second reporters, such as first and second probes. Signals from the first and second dyes can be detected in a detection instrument in distinct (e.g., at least substantially nonoverlapping) first and second channels (for example, a test channel and a control channel) as test signals and control signals, respectively.

Control templates can comprise exogenous molecules of the control target. In contrast, the sample can be tested for a presence of endogenous molecules of the test target. The control template can be present in any suitable amount to provide any suitable average number of control template molecules per droplet, to generate a desired fraction of droplets positive for the control template. For example, the number of template molecules provided by a template can be substantially less than an average of one per droplet, such as an average of about 0.1, 0.05, 0.02, or 0.01 molecule per droplet. In some cases, the number of template molecules is on average less than 1, less than 2, less than 3, less than 4, or less than 5 template molecules per droplet. In some cases, the number of template molecules is on average less than 6, less than 7, less than 8, less than 9, or less than 10 template molecules per droplet The frequency of amplification of the control target can be determined by performing an analysis. In some embodiments, this frequency can be compared with one or more previously determined frequencies of amplification for the control target and can be compared with an expected value for the frequency provided by a manufacturer. In any event, a control value can be determined, with the control value corresponding to a number and/or fraction of the droplets that are amplification-positive for the control nucleic acid target.

Control signals acquired can be used to measure and verify the quantitative accuracy of a run and the measurement precision of a detection instrument during two or more runs. The control signals can be used to interpret a test result, such as the quality of test data measured from a sample, for example, to verify the quantitative accuracy of the test data or to determine the validity or reliability of the test data. The test result can be interpreted based on control values determined. For example, the test result can be determined as being invalid if the control value is less than a threshold value. Furthermore, data acquired from the control channel, such as signals from amplification-negative control droplets, can provide reference signals. In other words, test signals can be transformed using control signals that functions as reference signals, to normalize the test signals.

Control reagents can amplify a control target that is known or expected to be present in a sample and/or that has a known or expected representation with respect to a bulk nucleic acid population present in the sample, such as total DNA, total genomic DNA, genomic DNA from a particular species of organism, total RNA, and total mRNA. In contrast, target reagents can amplify a test target that has an unknown presence in the sample or an unknown presence in with respect to the bulk nucleic acid population. In any event, amplification of the control target can be used to determine the quality of test data measured from a sample, such as to verify the quantitative accuracy of the test data and/or to determine the reliability of the test data. Furthermore, an amount of control target determined to be present in the sample can provide a standard against which an amount of test target determined to be present in the sample can be compared and/or normalized. In some embodiments, a control target is selected that is rare in the sample, such as a target representing a particular gene mutation. By selecting a rare control target, amplification of the control target can indicate the limit of detection of a test target or whether amplification of a low-abundance test target can occur. In some embodiments, the control target can be replaced by a second test target with an unknown presence in the sample before testing.

Control target reagents can be similar in general structure to the test target reagents, but different with respect to the nucleic acid sequences of the primers and probes, to provide test target and control target specificity, respectively. Also, the test and control probes can include distinct dyes and/or distinct energy transfer partners, such as distinct quenchers suitable for the respective dyes. In other embodiments, at least one of the probes can be replaced by a reporter or other signal including an intercalating dye, such as ethidium bromide, SYBR GREEN™, SYBR GOLD™, and EVAGREEN™.

Successful amplification of a control target can, for example, verify or measure aspects of a thermal cycler or a detection instrument, the quality of the reagents, fraction of amplification-positive droplets, or any combination thereof.

Dyes used as reagents for generation of droplets and droplet mixtures can have substantially overlapping absorption spectra, such that the same wavelength of light can be utilized to excite both dyes. In contrast, dyes can exhibit Stokes shifts (the difference in wavelength or frequency units between the maxima of the absorption and emission spectra of different magnitudes). For example, one dye can exhibit a smaller Stokes shift and a second dye can exhibit a larger Stokes shift, or vice versa. Accordingly, the emission spectra of the dyes can be substantially shifted with respect to one another. As a result, emission from the two dyes can be detected at least substantially independently of one another in different detector channels of a detection instrument, such as a detector channel that detects light of a first wavelength or wavelength range and another detector channel that detects light of a second wavelength or wavelength range.

A detection instrument can include a light source for exciting the fluorescent dyes in the droplets in the droplet mixtures and at least one detector for detecting light emitted from the droplets. A light source can, for example, include an LED or laser that emits at least substantially a single wavelength of excitation light. Alternatively, or in addition, the light source can include at least one excitation optical filter that excludes other wavelengths of light emanating from the light source. A detector can be equipped with detection optics, such as beamsplitters, emission optical filters, and separate detectors that permit emitted light from the dyes to be detected separately. In some embodiments, a detection instrument can include a camera for acquiring images of droplets, such as droplets arrayed on a two dimensional or three dimensional array. In some embodiments, images of droplets can be acquired from one or multiple channels, for example, when two or more dyes are utilized. For example, images of droplets can be acquired using a camera with a detector channel that detects light of a first wavelength or wavelength range and another detector channel that detects light of a second wavelength or wavelength range.

Any number of reagents can be added to samples to enable calibration with the droplets of the droplet mixtures. A reagent can be a compound, set of compounds, or composition that can be combined with a sample for generation of droplets within in droplet mixture in order to calibrate a particular test on the sample.

A reagent can include a binding partner, probe, primer, label, or reporter. A reagent can be a target-specific reagent, which is any reagent composition that confers specificity for detection of a particular target or analyte in a test. A reagent optionally can include a chemical reactant and/or a binding partner for the test. A reagent can, for example, include at least one nucleic acid, protein (e.g., an enzyme), cell, virus, organelle, macromolecular assembly, potential drug, lipid, carbohydrate, inorganic substance, or any combination thereof, and can be an aqueous composition, among others. In exemplary embodiments, the reagent can be an amplification reagent, which can include at least one primer or at least one pair of primers for amplification of a nucleic acid target, at least one probe and/or dye to enable detection of amplification, a polymerase, nucleotides, divalent magnesium ions, potassium chloride, buffer, or any combination thereof, among others.

A nucleic acid can be a compound comprising a chain of nucleotide monomers. A nucleic acid can be single-stranded or double-stranded. The chain of a nucleic acid can be composed of any suitable number of monomers, such as at least about ten or one hundred, among others. Generally, the length of a nucleic acid chain corresponds to its source, with synthetic nucleic acids, such as primers and probes, typically being shorter, and biologically or enzymatically generated nucleic acids, such as nucleic acid analytes, typically being longer.

A nucleic acid can have a natural or artificial structure, or a combination thereof. Nucleic acids with a natural structure, namely, deoxyribonucleic acid (DNA) and ribonucleic acid (RNA), generally have a backbone of alternating pentose sugar groups and phosphate groups. Each pentose group is linked to a nucleobase (e.g., a purine (such as adenine (A) or guanine (T)) or a pyrimidine (such as cytosine (C), thymine (T), or uracil (U))). Nucleic acids with an artificial structure are analogs of natural nucleic acids and can, for example, be created by changes to the pentose and/or phosphate groups of the natural backbone. Exemplary artificial nucleic acids include glycol nucleic acids (GNA), peptide nucleic acids (PNA), locked nucleic acid (LNA), threose nucleic acids (TNA), and the like.

The sequence of a nucleic acid can be defined by the order in which nucleobases are arranged along the backbone. This sequence generally determines the ability of the nucleic acid to bind specifically to a partner chain (or to form an intramolecular duplex) by hydrogen bonding. In particular, adenine pairs with thymine (or uracil) and guanine pairs with cytosine. A nucleic acid that can bind to another nucleic acid in an antiparallel fashion by forming a consecutive string of such base pairs with the other nucleic acid is termed "complementary."

Replication can be a process forming a copy (i.e., a direct copy and/or a complementary copy) of a nucleic acid or a segment thereof. Replication generally involves an enzyme, such as a polymerase and/or a ligase, among others. The nucleic acid and/or segment replicated can be a template (and/or a target) for replication.

Amplification can be a reaction in which replication occurs repeatedly over time to form multiple copies of at least one segment of a template molecule. Amplification can generate an exponential or linear increase in the number of copies as amplification proceeds. Typical amplifications produce a greater than 1,000-fold increase in copy number and/or signal. Exemplary amplification reactions for the droplet-based assays disclosed herein can include the polymerase chain reaction (PCR) or ligase chain reaction, each of which is driven by thermal cycling. The droplet mixtures can also be used for calibration of other amplification reactions, which can be performed isothermally, such as branched-probe DNA assays, cascade-RCA, helicase-dependent amplification, loop-mediated isothermal amplification (LAMP), nucleic acid based amplification (NASBA), nicking enzyme amplification reaction (NEAR), PAN-AC, Q-beta replicase amplification, rolling circle replication (RCA), self-sustaining sequence replication, strand-displacement amplification, and the like. Amplification can utilize a linear or circular template.

Amplification can be performed with any suitable reagents. Amplification can be performed, or tested for its occurrence, in an amplification mixture, which is any composition capable of generating multiple copies of a nucleic acid target molecule, if present, in the composition. An amplification mixture can include any combination of at least one primer or primer pair, at least one probe, at least one replication enzyme (e.g., at least one polymerase, such as at least one DNA and/or RNA polymerase), and deoxynucleotide (and/or nucleotide) triphosphates (dNTPs and/or NTPs), among others.

PCR nucleic acid amplification relies on alternating cycles of heating and cooling (e.g., thermal cycling) to achieve successive rounds of replication. PCR can be performed by thermal cycling between two or more temperature set points, such as a higher melting (denaturation) temperature and a lower annealing/extension temperature, or among three or more temperature set points, such as a higher melting temperature, a lower annealing temperature, and an intermediate extension temperature, among others. PCR can be performed with a thermostable polymerase, such as Taq DNA polymerase (e.g., wild-type enzyme, a Stoffel fragment, FastStart polymerase, etc.), Pfu DNA polymerase, S-Tbr polymerase, Tth polymerase, Vent polymerase, or a combination thereof, among others. PCR generally produces an exponential increase in the amount of a product amplicon over successive cycles.

Any suitable PCR methodology or combination of methodologies can be calibrated utilizing the droplet mixtures disclosed herein, such as allele-specific PCR, assembly PCR, asymmetric PCR, digital PCR, endpoint PCR, hot-start PCR, in situ PCR, intersequence-specific PCR, inverse PCR, linear after exponential PCR, ligation-mediated PCR, methylation specific PCR, miniprimer PCR, multiplex ligation-dependent probe amplification, multiplex PCR, nested PCR, overlapextension PCR, polymerase cycling assembly, qualitative PCR, quantitative PCR, real-time PCR, RT-PCR, single-cell PCR, solid-phase PCR, thermal asymmetric interlaced PCR, touchdown PCR, or universal fast walking PCR, among others. Digital PCR (e.g., droplet digital PCR) can refer to PCR performed on portions of a sample to determine the presence, absence, concentration, or copy number of a nucleic acid target in the sample, based on how many of the sample portions indicate amplification of the target. Digital PCR can be performed as endpoint PCR. In some cases, digital PCR can be performed as real-time PCR for each of the partitions.

PCR usually results in an amplification of a nucleic acid sequence from a sample. By measuring the number of amplification cycles required to achieve a threshold level of amplification, one can often calculate the starting concentration of nucleic acid. Often, PCR results in exponential amplification. In digital PCR, individual nucleic acid molecules are separated from the initial sample into partitions, then amplified to detectable levels. Each partition then provides digital information on the presence or absence of each individual nucleic acid molecule within each partition. When enough partitions are measured using this technique, the digital information can be consolidated to make a statistically relevant measure of starting concentration for the nucleic acid target (analyte) in the sample. Often, for digital PCR methods provided herein, a sample (e.g., a population of nucleic acids) is partitioned into multiple partitions have on average less than 1, less than 2, less than 3, less than 4, less than 5, less than 6, less than 7, less than 8, less than 9, or less than 10 copies of target nucleic acid per partition.

The concept of digital PCR may be extended to other types of analytes, besides nucleic acids. In particular, a signal amplification reaction may be utilized to permit detection of a single copy of a molecule of the analyte in individual droplets, to permit data analysis of droplet signals for other analytes. Exemplary signal amplification reactions that permit detection of single copies of other types of analytes in droplets include enzyme reactions.

A primer can be a nucleic acid capable of, and/or used for, priming replication of a nucleic acid template. Thus, a primer is a shorter nucleic acid that is complementary to a longer template. During replication, the primer is extended, based on the template sequence, to produce a longer nucleic acid that is a complimentary copy of the template. A primer may be DNA, RNA, an analog thereof (i.e., an artificial nucleic acid), or any combination thereof. A primer may have any suitable length, such as at least about 10, 15, 20, or 30 nucleotides. Exemplary primers are synthesized chemically. Primers may be supplied as at least one pair of primers for amplification of at least one nucleic acid target. A pair of primers may be a sense primer and an antisense primer that collectively define the opposing ends (and thus the length) of a resulting amplicon.

A probe can be a nucleic acid connected to at least one label, such as at least one dye. A probe may be a sequence specific binding partner for a nucleic acid target and/or amplicon. The probe may be designed to enable detection of target amplification based on fluorescence resonance energy transfer (FRET). An exemplary probe for the nucleic acid assays disclosed herein includes one or more nucleic acids connected to a pair of dyes that collectively exhibit fluorescence resonance energy transfer (FRET) when proximate one another. The pair of dyes may provide first and second emitters, or an emitter and a quencher, among others. Fluorescence emission from the pair of dyes changes when the dyes are separated from one another, such as by cleavage of the probe during primer extension (e.g., a 5' nuclease assay, such as with a TAQMAN probe), or when the probe hybridizes to an amplicon (e.g., a molecular beacon probe). The nucleic acid portion of the probe may have any suitable structure or origin, for example, the portion may be a locked nucleic acid, a member of a universal probe library, or the like. In other cases, a probe and one of the primers of a primer pair may be combined in the same molecule (e.g., AMPLIFLUOR primers or SCORPION primers). As an example, the primer-probe molecule may include a primer sequence at its 3' end and a molecular beacon-style probe at its 5' end. With this arrangement, related primer-probe molecules labeled with different dyes can be used in a multiplexed assay with the same reverse primer to quantify target sequences differing by a single nucleotide (single nucleotide polymorphisms (SNPs)). Another exemplary probe for droplet-based nucleic acid assays is a Plexor primer.

A label can be an identifying and/or distinguishing marker or identifier connected to or incorporated into any entity, such as a compound, biological particle (e.g., a cell, bacteria, spore, virus, or organelle), or droplet. A label may, for example, be a dye that renders an entity optically detectable and/or optically distinguishable. Exemplary dyes used for labeling are fluorescent dyes (fluorophores) and fluorescence quenchers.

A reporter can be a compound or set of compounds that reports a condition, such as the extent of a reaction. Exemplary reporters comprise at least one dye, such as a fluorescent dye or an energy transfer pair, and/or at least one oligonucleotide. Exemplary reporters for nucleic acid amplification assays may include a probe and/or an intercalating dye (e.g., SYBR GREEN™, SYBR GOLD™, EVAGREEN™, ethidium bromide, etc.).

A binding partner can be a member of a pair of members that bind to one another. Each member may be a compound or biological particle (e.g., a cell, bacteria, spore, virus, organelle, or the like), among others. Binding partners may bind specifically to one another. Specific binding may be characterized by a dissociation constant of less than about $10^{-4}$, $10^{-6}$, $10^{-8}$, or $10^{-°}$ M. Exemplary specific binding partners include biotin and avidin/streptavidin, a sense nucleic acid and a complementary antisense nucleic acid (e.g., a probe and an amplicon), a primer and its target, an antibody and a corresponding antigen, a receptor and its ligand, and the like.

EXAMPLES

Example 1

Preparing Large, Uniform, Stabilized Batches of Simulated Assay Droplets

Basic Reagents:
2× Buffer control stock solution
FAM (dye only) or FAM-conjugated oligo 10 uM stock solution
ddPCR Droplet Generation Oil
Bio-Rad part numbers:
Droplet Generation oil: 186-3005
Droplet Reader oil: 186-3004
Buffer control: 186-3052
96-well plate pierceable, heat-activated foil seals: AB-0757 (ABI part number)
PCR plates: 951020362 (Eppendorf semi-skirted, Eppendorf part number)
DG8 cartridges: 186-3008
Dye solutions were mixed at 40 nM (simulated negative) and 350 nM (simulated positive) by diluting 2× buffer control in nuclease-free water and adding the appropriate amount of 10 uM FAM-oligo solution.

40 nM and 350 nM drops were generated simultaneously at the same rate using syringes of each dye solution connected to a separate droplet generation cartridge (As in FIG. 1, schamtic 101) or separate channels of the same cartridge. Oil was pumped into the cartridge at 65 ul/min (or 130 ul/min if oil is split to supply both generation crosses) and sample was injected at 30 ul/min per syringe. The droplets were combined immediately following generation by directing droplets to a Y-junction fitting. The combined stream was directed or flowed to a serpentine mixing loop and heat was applied to the serpentine module at 95 degrees C. The duration of heating for any given droplet as it flowed through the serpentine mixing module was approximately 10 minutes.

Figure 6A:
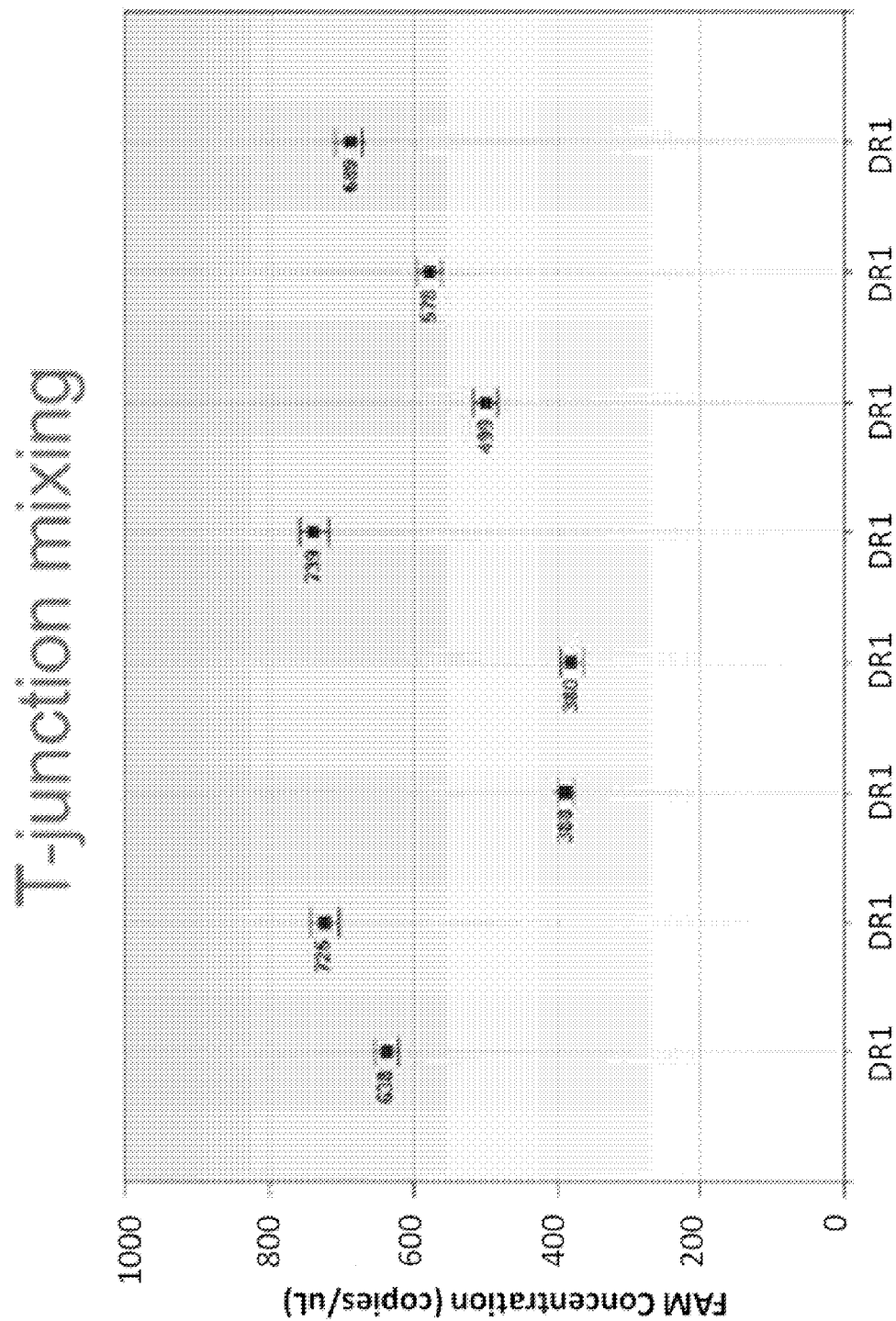
FIG. 6A provides a graphical depiction of simulated 6-carboxyfluorescein (FAM) concentrations determined by counting positive and negative droplets (prepared with known FAM concentrations) and converting to FAM concentration using a Poisson equation. Fluorescence emission was detected from droplets within the same droplet population flowed through a T-junction channel arrangement.
Figure 6C:
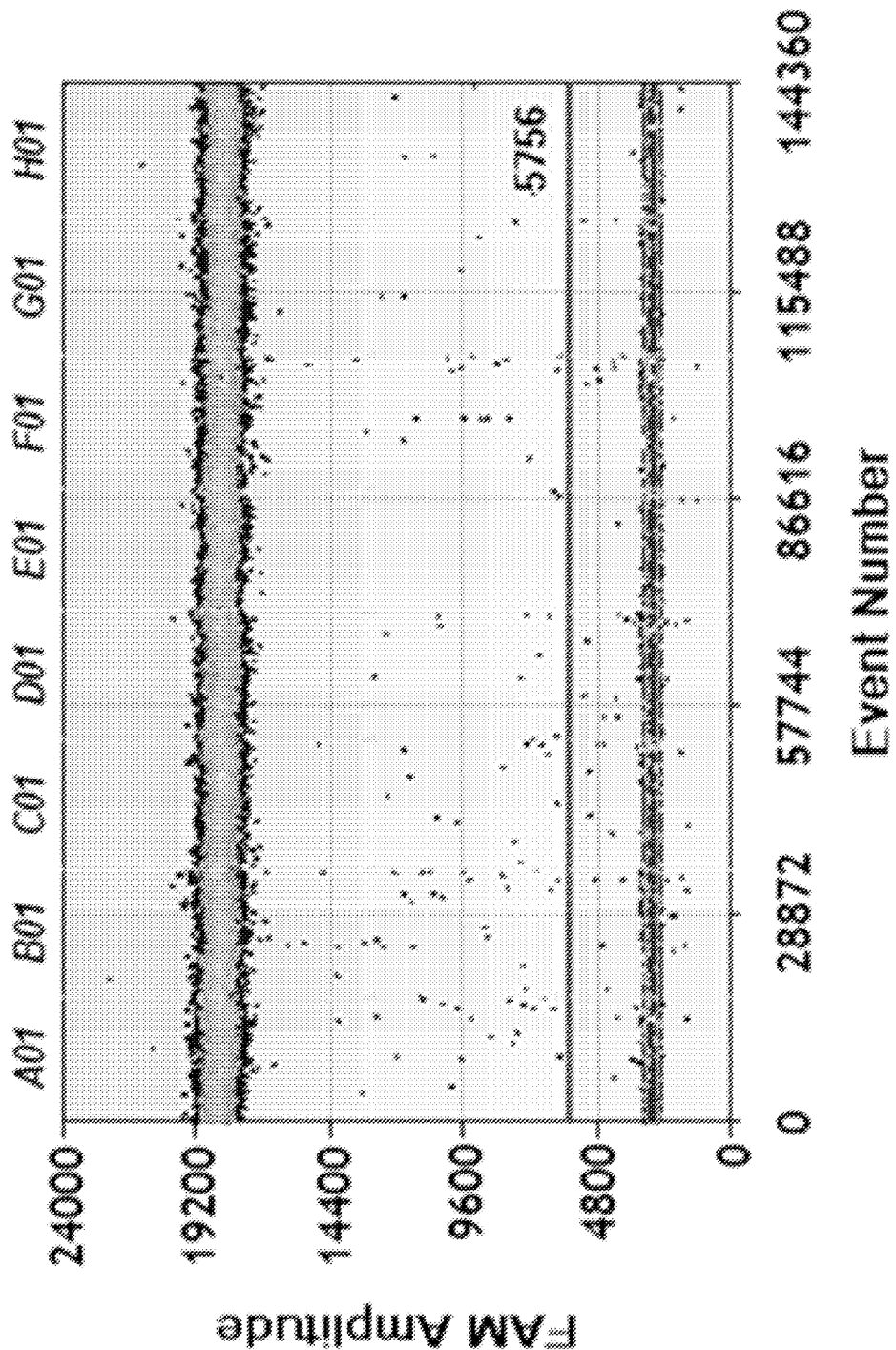
FIG. 6C provides a droplet reader amplitude plot of 6-carboxyfluorescein (FAM) amplitude determined by detecting fluorescence emission from simulated positive and negative droplets (prepared with known FAM concentrations). The droplets of each sample assayed were within the same mixed droplet population mixed using an in-line serpentine mixing channel arrangement according to the present disclosure. Eight replicate samples are represented. Droplets were flowed through a T-junction channel arrangement followed by flow through a serpentine channel arrangement.

Droplets were collected in an outlet reservoir after exiting the heated, serpentine mixing loop. After all droplets were generated, combined and flowed through the heated serpentine mixing module, the droplets were collected into a single reservoir. The excess oil was removed from underneath the volume of droplets, and the droplets were aliquotted by electronic or manual pipet into 96-well PCR plates at approximately 28 µL droplets per well with approximately 0-10 µL of droplet generation oil remaining at the bottom of each well. By this method, each well contained equal numbers of simulated negative (40 nM FAM) and simulated positive (350 nM FAM) droplets. In this example, the plate(s) were heat sealed with foil seals and stored (e.g., at 4 degrees C. or at room temperature) prior to use or shipment for use at another location. FIG. 6B shows a graph of simulated FAM concentrations determined by counting the positive and negative droplets (high-FAM and low-FAM droplets) and converting to concentration using a Poisson equation). FIG. 6C shows a droplet reader amplitude plot, using QuantaSoft to assess the data quality, showing FAM amplitude from eight wells containing combined droplet mixtures.

Example 2

Additional Methods for Preparing Storable and/or Transportable Droplets

Droplets were prepared using the in-line serpentine mixing module method with simulated assay (FAM dye) as previously described in above Example 1. Droplets were pipetted into Eppendorf Twin-tec semi-skirted 96-well plates (well volume=250 ul), and sealed with an Eppendorf heat sealer and pierceable metal foil. The total volume fraction of droplets in each well and the corresponding fraction of continuous phase oil in the well with the droplets was varied prior to sealing the plate. Droplet volume ranged from 28 µL to 250 µL (250 µL=completely full well) and oil volume ranged from 0 µL to 10 ul. An aliquot of droplets from the bulk generation batch was run on a Bio-Rad QX100 Droplet Reader to serve as a positive control for droplet quality (FIG. 7A, 16 wells). Once plates were filled and sealed, they were packaged with support by foam cushioning in cardboard shipping boxes. The boxes were sealed and sent to a collaborator in Mississippi via FedEx next day Air or FedEx ground. Droplets were then shipped back to Bio-Rad by the collaborator without opening the box. Upon receipt at Bio-Rad, plates were removed from the box and immediately run on a QX100 Droplet Reader. Data quality was assessed using QuantaSoft and QuantaGalaxy software (Bio-Rad) FIG. 7B depicts a non-ideal sample with a 28 µL volume and FIG. 7C depicts a well full of sample (250 µL) representing an ideal condition.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure.

When the word 'or' is used in reference to a list of two or more items, that word covers all of the following interpretations of the word: any of the items in the list, all of the items in the list and any combination of the items in the list.

The above description of illustrated embodiments of the systems and methods is not intended to be exhaustive or to limit the systems and methods to the precise form disclosed. While specific embodiments of, and examples for, the systems and methods are described herein for illustrative purposes, various equivalent modifications are possible within the scope of the systems and methods, as those skilled in the relevant art will recognize. The teachings of the systems and methods provided herein can be applied to other processing systems and methods, not only for the systems and methods described above.

The elements and acts of the various embodiments described above can be combined to provide further embodiments. These and other changes can be made to the systems and methods in light of the above detailed description.

In general, in the following claims, the terms used should not be construed to limit the systems and methods to the specific embodiments disclosed in the specification and the claims, but should be construed to include all processing systems that operate under the claims. Accordingly, the systems and methods are not limited by the disclosure, but instead the scope of the systems and methods is to be determined entirely by the claims.

While certain aspects of the systems and methods are presented below in certain claim forms, the inventors contemplate the various aspects of the systems and methods in any number of claim forms. Accordingly, the inventors reserve the right to add additional claims after filing the application to pursue such additional claim forms for other aspects of the systems and methods.

What is claimed is:

1. A method comprising the steps of:
   (a) combining a first droplet population with a second droplet population to form a combined droplet population;
   (b) mixing the combined droplet population in a mixing module to produce a mixture in which each of the first droplet population and the second droplet population remains substantially intact;
   (c) stabilizing droplets of the first droplet population and droplets of the second droplet population by heating that forms a droplet skin including a skin-forming protein; and
   (d) shipping at least a portion of the combined droplet population at least one kilometer after the steps of mixing and stabilizing.

2. The method of claim 1, wherein the step of mixing the combined droplet population includes a step of flowing the combined droplet population through the mixing module using a pressure source to drive flow of the combined droplet population.

3. The method of claim 2, wherein the step of flowing the combined droplet population includes a step of flowing the combined droplet population through a mixing channel of the mixing module.

4. The method of claim 3, wherein the mixing channel has a nonlinear configuration including at least one turn.

5. The method of claim 1, wherein the step of combining a first droplet population with a second droplet population occurs in the mixing module.

6. The method of claim 1, further comprising a step of detecting a signal from the combined droplet population.

7. The method of claim 6, wherein droplets of the combined droplet population have been stored at least 24 hours before the step of detecting a signal.

8. The method of claim 6, wherein the step of detecting a signal includes a step of detecting a relatively high fluorescence emission from droplets of the first droplet population and a relatively low fluorescence emission from droplets of the second droplet population.

9. The method of claim 1, further comprising a step of partitioning a sample with a first droplet generator to produce the first droplet population and a step of partitioning a sample with a second droplet generator to produce the second droplet population, wherein the first droplet generator is different from the second droplet generator.

10. The method of claim 1, wherein, during the step of combining a first droplet population with a second droplet population, at least a portion of the first droplet population is present in a first channel and at least a portion of the second droplet population is present in a second channel that is different from the first channel.

11. The method of claim 10, wherein the first channel and the second channel intersect one another.

12. The method of claim 10, wherein the first channel and the second channel are in fluid communication with the mixing module during the step of combining a first droplet population with a second droplet population.

* * * * *